United States Patent
Azhir et al.

(10) Patent No.: US 12,233,086 B2
(45) Date of Patent: Feb. 25, 2025

(54) BIOMARKERS FOR NEUROGENERATIVE DISEASE

(71) Applicants: Neuvivo, Inc., Palo Alto, CA (US); The Regents of the University of California, Oakland, CA (US)

(72) Inventors: Arasteh Azhir, Los Altos, NY (US); Michael S. McGrath, Meadow Vista, CA (US); Bruce D. Forrest, Nyack, NY (US)

(73) Assignees: NEUVIVO, INC., Palo Alto, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/319,355

(22) Filed: May 17, 2023

(65) Prior Publication Data
US 2023/0390331 A1    Dec. 7, 2023

Related U.S. Application Data

(60) Provisional application No. 63/484,678, filed on Feb. 13, 2023, provisional application No. 63/410,724, filed on Sep. 28, 2022, provisional application No. 63/392,237, filed on Jul. 26, 2022, provisional application No. 63/343,568, filed on May 19, 2022.

(51) Int. Cl.
*A61K 33/20* (2006.01)
*A61P 25/28* (2006.01)
*G01N 33/68* (2006.01)

(52) U.S. Cl.
CPC .............. *A61K 33/20* (2013.01); *A61P 25/28* (2018.01); *G01N 33/6863* (2013.01); *G01N 33/6896* (2013.01); *G01N 2333/495* (2013.01); *G01N 2800/2835* (2013.01); *G01N 2800/52* (2013.01)

(58) Field of Classification Search
CPC .............. A61K 33/20; G01N 33/6863; G01N 33/6896; G01N 2800/52; G01N 2800/2835; G01N 2333/495; A61P 25/28
See application file for complete search history.

(56) References Cited

U.S. PATENT DOCUMENTS

| | | |
|---|---|---|
| 7,105,183 B2 | 9/2006 | McGrath |
| 8,029,826 B2 | 10/2011 | McGrath |
| 8,231,856 B2 | 7/2012 | Boulanger et al. |
| 8,501,244 B2 | 8/2013 | Boulanger et al. |
| 9,266,734 B2 | 2/2016 | Boulanger et al. |
| 9,364,501 B2 | 6/2016 | McGrath |
| 9,579,346 B2 | 2/2017 | McGrath et al. |
| 9,839,650 B2 | 12/2017 | Boulanger et al. |
| 2011/0086894 A1 | 4/2011 | Bowser |
| 2012/0134929 A1 | 5/2012 | McGrath et al. |
| 2017/0006563 A1 | 1/2017 | Lindoff et al. |
| 2017/0065634 A1* | 3/2017 | McGrath ................ A61P 31/00 |
| 2023/0172974 A1 | 6/2023 | Norviel et al. |
| 2023/0181629 A1 | 6/2023 | Norviel et al. |
| 2023/0190789 A1 | 6/2023 | Norviel et al. |
| 2023/0190790 A1 | 6/2023 | Azhir et al. |
| 2023/0218662 A1 | 7/2023 | Norviel et al. |

FOREIGN PATENT DOCUMENTS

| | | |
|---|---|---|
| WO | WO-2013093891 A1 | 6/2013 |
| WO | WO-2015175974 A1 | 11/2015 |
| WO | WO 2017079161  *  | 5/2017 |
| WO | WO-2017079161 A2 | 5/2017 |
| WO | WO-2022005875 A1 | 1/2022 |

OTHER PUBLICATIONS

Xu et al. (Neurofliiaments Biomarkers and ALS (Oct. 12, 2016 p. 1-18).*
Cao et al. (BMC Neurology (2022)22:216 p. 1-12).*
Kashima et al. (Acta Biocheim Biophys Sin (shanghai) Jan. 2018. 50(1): 106-120).*
Cieślak et al. Epidermal growth factor in human cerebrospinal fluid: reduced levels in amyotrophic lateral sclerosis. J Neurol 233(6):376-377 (1986).
Kagel et al. Considerations in the development of a sensitive HPLC assay for human epidermal growth factors in human plasma. J Pharm Biomed Anal 13(10):1205-1213 (1995).
PCT/US2023/022598 International Search Report and Written Opinion dated Oct. 4, 2023.
Zhang et al. Macrophage-Targeted Sodium Chlorite (NP001) Slows Progression of Amyotrophic Lateral Sclerosis (ALS) through Regulation of Microbial Translocation. Biomedicines 10(11):2907 (2022).
Caraci et al. Caraci et al. Neurobiological links between depression and AD: The role of TGF-β1 signaling as a new pharmacological target. Pharmacol Res. 130:374-384 (2018).
Galbiati et al. Multiple Roles of Transforming Growth Factor Beta in Amytotrophic Lateral Sclerosis/ Int J Mol Sci 21(12):4291 (2020).
Meroni et al. Transforming growth factor beta 1 signaling is altered in the spinal cord and muscle of amyotrophic lateral sclerosis mice and patients. Neurobiol Aging 82:48-59 (2019).
Miller et al., NP001 regulation of macrophage activation markers in ALS: A phase I clinical and biomaker study. Amyotrophic Lateral Sclerosis and Frontotemporal Degeneration 15:601-609 (2014).
Miller et al. Phase 2B randomized controlled trial of NP001 in amyotrophic lateral sclerosis: Pre-specified and post hoc analyses. Muscle Nerve. 66(1):39-49 (2022).
Miller et al., Randomized phase 2 trial of NP001-a novel immune regulator: Safety and early efficacy in ALS. Neurol Neuroimmunol Neuroinflamm 2:e100 (2015).
PCT/US2023/022598 International Invitation to Pay Additional Fees dated Jul. 27, 2023.
Ramirez et al. The Role of TGFβ Signaling in Wound Epithelialization. Adv Wound Care (New Rochelle) 3(7):482-491 (2014).
Wyatt et al. Hypochlorite-induced structural modifications enhance the chaperone activity of human α2-macroglobulin. PNAS USA 111(20):E2081 (2014).

(Continued)

*Primary Examiner* — Shirley V Gembeh
(74) *Attorney, Agent, or Firm* — WILSON SONSINI GOODRICH & ROSATI

(57) ABSTRACT

Described herein are methods of monitoring and treating a subject with ALS based on biomarkers.

18 Claims, 28 Drawing Sheets

(56) References Cited

OTHER PUBLICATIONS

Zhang et al. Circulating endotoxin and systemic immune activation in sporadic Amyotrophic Lateral Sclerosis. J Neuroimmunol 206(1-2):121-142 (2009).

* cited by examiner

A) Phrenic Nerve axon Inflammation modulated

Phase 2A/2B NP001 change from baseline Vital Capacity (CRP > 1.13 mg/L, age 40-65)

B) Systemic inflammation and microbial translocation reversed

Phase 2A/2B "responders": 0 loss of ALSFRS-R score over 6 months; (baseline CRP > 3 mg/L, age 40-65)

CRP: C-reactive protein; measure of inflammation

*: stable defined as 0 loss of ALSFRS-R score over 6 months

BIOMARKERS FOR NEUROGENERATIVE DISEASE

CROSS-REFERENCE TO RELATED APPLICATIONS

This application claims the benefit of U.S. Provisional Patent Application No. 63/343,568, filed on May 19, 2022, and U.S. Provisional Patent Application No. 63/392,237, filed on Jul. 26, 2022, and U.S. Provisional Patent Application No. 63/410,724, filed on Sep. 28, 2022, and U.S. Provisional Patent Application No. 63/484,678, filed on Feb. 13, 2023, which are each incorporated by reference herein in their entireties.

BACKGROUND

Amyotrophic lateral sclerosis (ALS) is a progressive neurodegenerative disease that destroys motor neurons in the brain and spinal cord. ALS eventually leads to muscle paralysis and death, often within 2-4 years of diagnosis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Described herein are methods of monitoring and treating a subject with ALS based on biomarkers.

In some embodiments, the method comprises: (a) identifying that a subject has a ratio of LPS:EGF associated with ALS; and (b) based on the identifying that the subject has the ratio of LPS:EGF associated with ALS, determining that the subject is eligible for sodium chlorite therapy for the ALS. In some embodiments, the method comprises: (a) identifying that a subject has a level of TGFB1 associated with ALS; and (b) based on the identifying that the subject has the level of TGFB1 associated with ALS, determining that the subject is eligible for sodium chlorite therapy for the ALS. In some embodiments, the method comprises: (a) identifying that a subject has a level of LBP associated with ALS; and (b) based on the identifying that the subject has the level of LBP associated with ALS, determining that the subject is eligible for sodium chlorite therapy for the ALS.

In some embodiments, the method comprises treating ALS in a subject in need thereof, the method comprising: (a) identifying that a subject has a ratio of LPS:EGF associated with ALS; and (b) based on the identifying that the subject has the ratio of LPS:EGF associated with ALS, administering to the subject an amount of sodium chlorite that is therapeutically-effective for ALS. In some embodiments, the method comprises treating ALS in a subject in need thereof, the method comprising: (a) identifying that a subject has a level of TGFB1 associated with ALS; and (b) based on the identifying that the subject has the level of TGFB1 associated with ALS, administering to the subject an amount of sodium chlorite that is therapeutically-effective for ALS. In some embodiments, the method comprises treating ALS in a subject in need thereof, the method comprising: (a) identifying that a subject has a level of LBP associated with ALS; and (b) based on the identifying that the subject has the level of LBP associated with ALS, administering to the subject an amount of sodium chlorite that is therapeutically-effective for ALS.

In some embodiments, the method comprises: (a) determining a ratio of LPS:EGF in a subject that has ALS, wherein the subject is undergoing a treatment for the ALS, wherein the treatment is a therapeutic regimen of sodium chlorite; and (b) determining based on the ratio of LPS:EGF whether to continue the therapeutic regimen of sodium chlorite. In some embodiments, the method comprises: (a) determining a level of TGFB1 in a subject that has ALS, wherein the subject is undergoing a treatment for the ALS, wherein the treatment is a therapeutic regimen of sodium chlorite; and (b) determining based on the level of TGFB1 whether to continue the therapeutic regimen of sodium chlorite. In some embodiments, the method comprises: (a) determining a level of LBP in a subject that has ALS, wherein the subject is undergoing a treatment for the ALS, wherein the treatment is a therapeutic regimen of sodium chlorite; and (b) determining based on the level of LBP whether to continue the therapeutic regimen of sodium chlorite.

In some embodiments, the method comprises: (a) obtaining a first level of inflammatory macrophages in a gut epithelium of a subject who has ALS, wherein the first level of inflammatory macrophages in the gut epithelium of the subject who has ALS is based on a blood assay; (b) based at least in part on the first level of inflammatory macrophages in the gut epithelium of the subject, starting the subject on a regimen of sodium chlorite administration for a time period of about six months; (c) after the time period, obtaining a second level of inflammatory macrophages in the gut epithelium of the subject; (d) determining that the second level of inflammatory macrophages in the gut epithelium of the subject is lower than the first level of inflammatory macrophages in the gut epithelium of the subject by a predetermined threshold amount; and (e) based at least in part on the determining that the second level of inflammatory macrophages in the gut epithelium of the subject is lower than the first level of inflammatory macrophages in the gut epithelium of the subject by the predetermined threshold amount, recommending that the subject continue the regimen of sodium chlorite administration.

In some embodiments, the method comprises: (a) obtaining a first level of LBP of a subject who has ALS, wherein the first level of LBP of the subject who has ALS is based on a blood assay; (b) based at least in part on the first level of LBP of the subject, starting the subject on a regimen of sodium chlorite administration for a time period of at least about six months; (c) after the time period, obtaining a second level of LBP of the subject; (d) determining that the second level of LBP is lower than the first level of LBP of the subject by a predetermined threshold amount; and (e) based at least in part on the determining that the second level of LBP of the subject is lower than the first level of LBP of the subject by the predetermined threshold amount, recommending that the subject continue the regimen of sodium chlorite administration.

In some embodiments, the method comprises: (a) obtaining a first level of TGFB1 of a subject who has ALS, wherein the first level of TGFB1 of the subject who has ALS is based on a blood assay; (b) based at least in part on the first level of TGFB1 of the subject, starting the subject on a regimen of sodium chlorite administration for a time period of at least about six months; (c) after the time period, obtaining a second level of TGFB1 of the subject; (d) determining that the second level of TGFB1 is higher than the first level of TGFB1 of the subject by a predetermined threshold amount; and (e) based at least in part on the determining that the second level TGFB1 of the subject is higher than the first level of TGFB1 of the subject by the predetermined threshold amount, recommending that the subject continue the regimen of sodium chlorite administration.

In some embodiments, the method comprises: (a) obtaining a first plasma neurofilament light chain level of a subject who has ALS, wherein the first plasma neurofilament light chain level of the subject who has ALS is based on a blood assay; (b) based at least in part on the first plasma neurofilament light chain level of the subject, starting the subject on a regimen of sodium chlorite administration for a time period of about six months; (c) after the time period, obtaining a second plasma neurofilament light chain level of the subject; (d) determining that the second plasma neurofilament light chain level of the subject is a decrease of at least a predetermined threshold amount in comparison to the first plasma neurofilament light chain level of the subject; and (e) based at least in part on the determining that the second plasma neurofilament light chain level of the subject is a decrease of at least the predetermined threshold amount in comparison to the first plasma neurofilament light chain level of the subject, recommending that the subject continue the regimen of sodium chlorite administration.

In some embodiments, the method comprises a method of treating ALS in a subject in need thereof, the method comprising: (a) obtaining a first level of a first biomarker in the subject; (b) obtaining a first level of the second biomarker in the subject; (c) after obtaining the first level of the first biomarker in the subject and obtaining the first level of the second biomarker in the subject, starting the subject on a regimen of sodium chlorite administration for a time period of at least about six months; (d) after the time period, obtaining a second level of the first biomarker in the subject; (e) after the time period, obtaining a second level of the second biomarker in the subject; (f) determining that the first level of the first biomarker in the subject is greater than the second level of the first biomarker in the subject; (g) determining that the first level of the second biomarker in the subject is lesser than the second level of the second biomarker in the subject; and (h) based at least in part on the determining that the first level of the first biomarker in the subject is greater than the second level of the first biomarker in the subject and the determining that the first level of the second biomarker in the subject is lesser than the second level of the second biomarker in the subject, recommending that the subject continue the regimen of sodium chlorite administration.

DETAILED DESCRIPTION OF THE INVENTION

Figure 1:
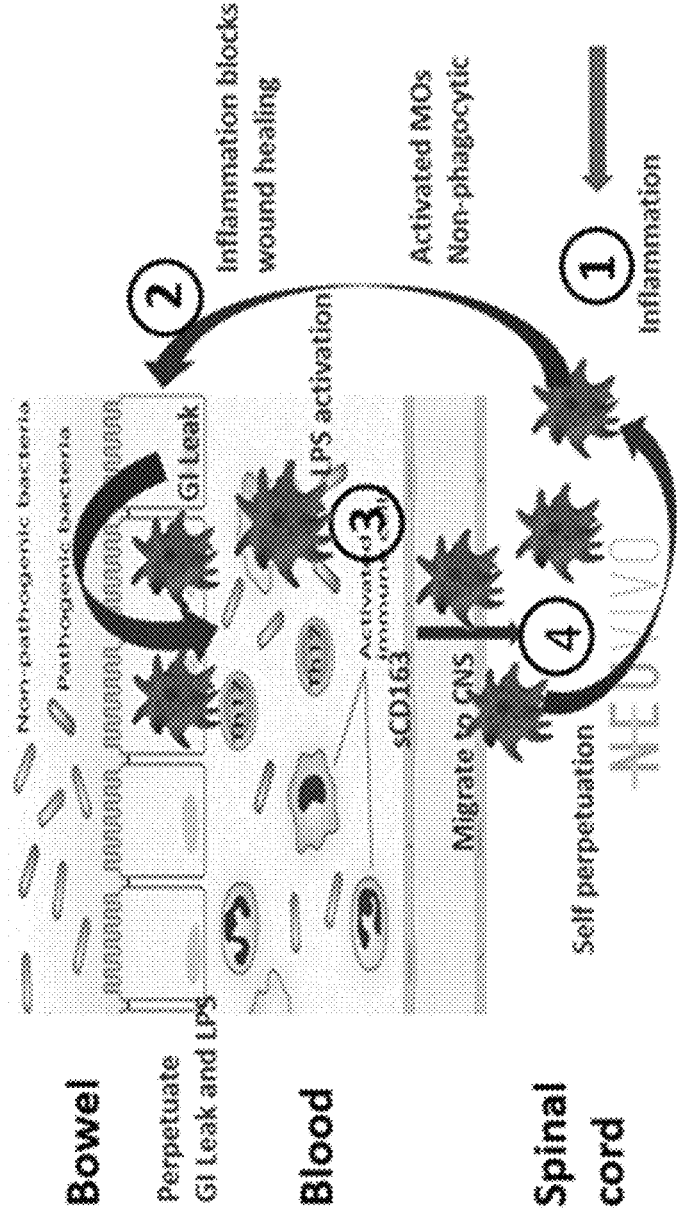
FIG. 1 shows ALS pathogenesis.

Amyotrophic lateral sclerosis (ALS), also known as Lou Gehrig's disease, is a fatal neurodegenerative disease associated with inappropriate immune system dysfunction involving NF-kB activation, proinflammatory factor production, and progressive changes in motor neuron function. Factors elaborated by spinal cord microglia both damage and inhibit repair of neurons injured by the accumulation of misfolded proteins. Inflammation and immune system dysregulation are involved in the progression of ALS, including the presence of activated macrophages in ALS patients. Compounds that can reduce inflammation and immune system dysregulation, possibly by returning macrophages to their inactivated state, can be effective in treating ALS or other disorders with immune system dysfunction.

Macrophages are white blood cells produced by the division of monocytes, which play a role in innate immunity (non-specific immune defenses) and help to initiate adaptive immunity (specific defense mechanisms). The cells phagocytose (i.e., engulf and then digest) cellular debris and pathogens either as stationary or as mobile cells. When activated by pathogens or other mechanisms, macrophages stimulate and recruit lymphocytes and other immune cells to respond. Activated macrophages are involved in the progression of several diseases and disorders, including amyotrophic lateral sclerosis (ALS). Activated macrophages elicit massive leukocyte infiltration and flood surrounding tissue with inflammatory mediators, pro-apoptotic factors, and matrix degrading proteases. These actions can result in inflammation that can dismantle tissues to the point of inflicting serious injury. Tissue destruction perpetrated by macrophage-induced inflammation, a form of immune system dysregulation, can be associated with the progression of the degenerative disease ALS.

ALS patients can be defined by four generalized patient groups: slowly progressive, fast progressive, early disease presentation, and late disease presentation. Of the four categories, only the slowly progressive patient group includes inflammation as a significant aspect of ALS disease pathology. The slowly progressive subset's association with inflammation is inferred upon study of ALS in association with C-reactive protein (CRP) levels over time from diagnosis. The longer an ALS patient lives after diagnosis, the higher the plasma CRP. A large subgroup of ALS patients is evidence for ongoing, and potentially growing, inflammation associated with a slower rate of progression. Methods of identifying ALS patients with inflammation are needed to treat such ALS patients with targeted immune regulating therapies.

ALS can also be distinguished by ALS symptoms, genetic cause, lack of clear genetic association, or combinations thereof. In comes embodiments, subjects with ALS can be categorized as sporadic or inherited ALS. Sporadic ALS pathology occurs in subjects with no genetic or family history of ALS, while inherited ALS pathology occurs in subjects with a genetic or family history of ALS. As many as 90% to 95% of ALS cases can be sporadic and occur in subjects with no genetic or family history of ALS.

Mutations to one or more genes can be associated with subjects experiencing either an inherited or sporadic ALS pathology. For instance, 60% of individuals with familial ALS can have an identified genetic mutation to one or more genes associated with the condition. In some embodiments, subjects experiencing either an inherited ALS pathology have inherited mutations to one or more of the genes listed in TABLE 1. Mutations in the C9orf72 gene account for 30% to 40% of inherited ALS in the United States and Europe; worldwide SOD1 gene mutations cause 15% to 20% of inherited ALS; and TARDBP and FUS gene mutations each account for about 5% of cases of inherited ALS.

In some embodiments, mutations to one or more genes listed in TABLE 1 can be important to the normal functioning of motor neurons and other cells, and mutations to one or more of these genes can contribute to the decline in function or death of motor neurons in ALS patients. In some embodiments, mutations to one or more genes of TABLE 1 can contribute to a decline in motor neutron function or neuron death as a result of buildup of protein aggregates in motor neurons, a slowing in the transport of materials needed for the proper function of axons in motor neurons, an accumulation of toxic substances in the motor neurons, or combinations thereof.

TABLE 1

Gene Associated with ALS

Figure 4:
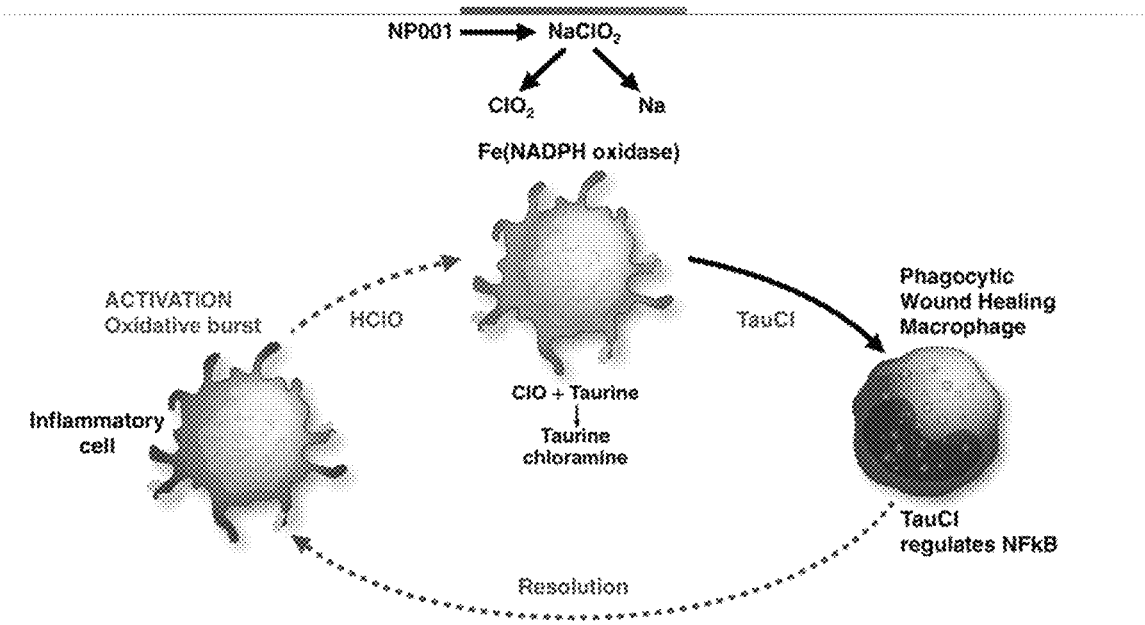
FIG. 4 shows the innate immune activation cycle that occurs in response to exposure of the immune system to infections or tissue damage.

| | |
|---|---|
| 1 | SOD1 |
| 2 | ALS2 |
| 3 | Chromosome 18 |
| 4 | SEXT |
| 5 | SPG11 |
| 6 | FUS |
| 7 | Chromosome 20 |
| 8 | VAPB |
| 9 | ANG |
| 10 | TARDBP/TDP-43 |
| 11 | FIG4 |
| 12 | OPTN |
| 13 | ATXN2 |
| 14 | VCP |
| 15 | UBQLN2 |
| 16 | SIGMAR1 |
| 17 | CHMP2B |
| 18 | PFN1 |
| 19 | ERBB4 |
| 20 | HNRNPA1 |
| 21 | MATR3 |
| 22 | TUBA4A |
| 23 | ANXA11 |
| 24 | NEK1 |
| 25 | C9orf72 |
| 26 | CHCHD10 |
| 27 | SQSTM1 |
| 28 | TARDBP |
| 29 | SETX |
| 30 | TAF15 |
| 31 | EWSR1 |
| 32 | hnRNPA2B1 |
| 33 | ELP3 |
| 34 | TBK1 |
| 35 | DCTN1 |
| 36 | NEFH |
| 37 | PRPH |
| 38 | C19ORF12 |
| 39 | SS18L1 |
| 40 | PNPLA6 |
| 41 | PON1-3 |
| 42 | DAO |
| 43 | CHRNA3, 4, B4 |
| 44 | ALS3 |
| 45 | ALS7 |
| 46 | ALS6-21 |
| 47 | ALS-FTD |

Initial events of ALS pathogenesis occur at the neuromuscular junction where neuron axonal processes interact with muscle out-side the central nervous system. This reaction is inflammatory and is mediated by components of the innate immune system including acute phase reactant proteins and blood derived granulocytes and macrophages. The triggering events can be linked to the presence of abnormally folded or aggregated proteins associated with ALS such as TDP43 and SOD-1, recognized by the innate immune system within the neuromuscular junction. Normally, the acute phase reaction is followed closely by immune signals that turn off that reaction to have the immune system remain in balance. Therefore, the plasma based or humoral innate immune system provides feedback on activated macrophages, the cellular drivers of inflammation and balance the inflammatory with anti-inflammatory immune signals. Proteins associated with the acute phase innate immune response can be measured in the blood and one, C-reactive protein (CRP), allows quantitative determination of the degree of inflammation associated with disease.

Plasma CRP levels are acutely elevated more than 30-fold in an acute phase reaction, but rapidly fall as the initiator of the inflammation becomes controlled. Two categories of insult cause the synthesis of CRP predominantly from the liver: infection and tissue damage. Infections can trigger both the innate and the adaptive response so that blood levels of factors produced by both immune reactions are present in the plasma. Although CRP rapidly appears after an insult and is viewed as a marker for inflammation severity, the general function is to facilitate phagocytic cell clearance of foreign material. In addition, CRP down regulates other proinflammatory components of the innate immune response to turn down the production of inflammatory by-products. Therefore, if CRP levels are chronically elevated, then ongoing infectious or tissue damaging processes are possibly driving the persistent CRP response. Continued tissue damage absent the persistence of an acute phase process suggests uncoupling of the innate immune response to signals that normally drive that reaction.

Other plasma factors involved in innate immune response include serum amyloid A (SAA), levels of which increase in parallel with CRP. SAA binds to and clears bacterial byproducts such as lipopolysaccharide (LPS). Alpha 2 macroglobulin (A2M) becomes activated when the acute phase reaction is initiated and clears by-products of damaged cells, specifically proteases. When further activated by hypochlorite, a byproduct of the oxidative burst reaction initiated by phagocyte (granulocytes, macrophages) activation, A2M forms a dimer, releases preformed TGFB1, and binds to and removes misfolded proteins and aggregates.

The innate immune system responds rapidly to infection and/or tissue damage. Within minutes, the acute phase reactants CRP and serum amyloid A (SAA) increase more than 30-fold in plasma. When an inflammatory response is initiated, byproducts of that response need to be removed or neutralized to avoid significant tissue damage. CRP facilitates the clearance of dead cells and protein aggregates. SAA binds to and removes products of bacterial clearance mediated by activated phagocytes such as LPS.

TGFB1 is a potent regulator of inflammation and down regulates inflammatory drive. Together, CRP, SAA, and A2M represent major humoral components of the innate immune system and coordinate to regulate the degree of inflammatory reactions associated with the activated cellular components of the response (macrophages, granulocytes).

NP001 can augment the innate immune activation cycle in ALS patients with elevated baseline plasma CRP. The innate immune activation cycle is a self-regulated process that occurs after the immune system is exposed to infection or tissue damage. The initiator of immune system activation can be the presence of misfolded or aggregated proteins, including TDP43.

In response to immune system activation, blood derived macrophages undergo oxidative burst and release hypochlorous acid as a byproduct. The acute phase response involves elevation of CRP and SAA. CRP facilitates clearance of damaged cells and tissues. SAA binds to and clears bacterial byproducts, including LPS. A2M is activated to remove damaged cell products, including proteases. Hypochlorous acid stimulates the production of taurine chloramine (TauCl) and promotes dimerization of A2M. A2M dimers clear misfolded proteins and release pre-synthesized TGFB1 to feedback on proinflammatory cells and turn off NFkB. NP001 is converted in vivo to HClO and stimulates dimerization of A2M and subsequent release of pre-synthesized TGFB1.

Methods

Disclosed herein are methods of identifying a subject with ALS that can be responsive to immune regulating therapies. In some embodiments, disclosed herein is a method of treating a subject with slowly progressive ALS with a pharmaceutical composition comprising sodium chlorite. In some embodiments, disclosed herein is a pharmaceutical composition for use in treating a condition, for example, ALS, Parkinson's disease, Alzheimer's disease, chronic obstructive pulmonary disease (COPD), or colitis.

Disclosed herein are compositions and methods for treating neurodegenerative diseases. Non-limiting examples of neurodegenerative diseases include amyotrophic lateral sclerosis (ALS, or Lou Gehrig's disease), Alzheimer's disease, vascular dementia, Parkinson's disease, multiple sclerosis, and primary progressive multiple sclerosis. In some embodiments, the neurodegenerative disease is ALS. In some embodiments, the neurodegenerative disease is Alzheimer's disease. In some embodiments, the neurodegenerative disease is Parkinson's disease. Treatments can include, for example, a formulation of sodium chlorite.

Disclosed herein are methods comprising identifying a subject has a level or ratio of one or more biomarkers associated with ALS; and based on the identifying that the subject has a level or ratio of one or more biomarkers associated with ALS, determining that the subject is eligible for sodium chlorite therapy for the ALS.

In some embodiments, the method comprises: (a) identifying that a subject has a ratio of LPS:EGF associated with ALS; and (b) based on the identifying that the subject has the ratio of LPS:EGF associated with ALS, determining that the subject is eligible for sodium chlorite therapy for the ALS.

In some embodiments, the method comprises: (a) identifying that a subject has a level of TGFB1 associated with ALS; and (b) based on the identifying that the subject has the level of TGFB1 associated with ALS, determining that the subject is eligible for sodium chlorite therapy for the ALS.

In some embodiments, the method comprises: (a) identifying that a subject has a level of LBP associated with ALS; and (b) based on the identifying that the subject has the level of LBP associated with ALS, determining that the subject is eligible for sodium chlorite therapy for the ALS.

In some embodiments, the method further comprises recommending that the subject undergo the sodium chlorite therapy for the ALS based on the determining that the subject is eligible for sodium chlorite therapy for the ALS.

Disclosed herein are methods of treating ALS in a subject in need thereof comprising identifying that the subject has a level or ratio of one or more biomarkers associated with ALS; and based on the identifying that the subject has a level or ratio of one or more biomarkers associated with ALS, administering to the subject an amount of sodium chlorite that is therapeutically-effective for ALS.

In some embodiments, the method comprises treating ALS in a subject in need thereof, the method comprising: (a) identifying that a subject has a ratio of LPS:EGF associated with ALS; and (b) based on the identifying that the subject has the ratio of LPS:EGF associated with ALS, administering to the subject an amount of sodium chlorite that is therapeutically-effective for ALS.

In some embodiments, the method comprises treating ALS in a subject in need thereof, the method comprising: (a) identifying that a subject has a level of TGFB1 associated with ALS; and (b) based on the identifying that the subject has the level of TGFB1 associated with ALS, administering to the subject an amount of sodium chlorite that is therapeutically-effective for ALS.

In some embodiments, the method comprises treating ALS in a subject in need thereof, the method comprising: (a) identifying that a subject has a level of LBP associated with ALS; and (b) based on the identifying that the subject has the level of LBP associated with ALS, administering to the subject an amount of sodium chlorite that is therapeutically-effective for ALS.

Disclosed herein are methods comprising determining a level or ratio of one or more biomarkers in a subject that has ALS, wherein the subject is undergoing a treatment for the ALS, wherein the treatment is a therapeutic regimen of sodium chlorite; and determining based on the level or ratio of one or more biomarkers whether to continue the therapeutic regimen of sodium chlorite.

In some embodiments, the method comprises: (a) determining a ratio of LPS:EGF in a subject that has ALS, wherein the subject is undergoing a treatment for the ALS, wherein the treatment is a therapeutic regimen of sodium chlorite; and (b) determining based on the ratio of LPS:EGF whether to continue the therapeutic regimen of sodium chlorite.

In some embodiments, the method comprises: (a) determining a level of TGFB1 in a subject that has ALS, wherein the subject is undergoing a treatment for the ALS, wherein the treatment is a therapeutic regimen of sodium chlorite; and (b) determining based on the level of TGFB1 whether to continue the therapeutic regimen of sodium chlorite.

In some embodiments, the method comprises: (a) determining a level of LBP in a subject that has ALS, wherein the subject is undergoing a treatment for the ALS, wherein the treatment is a therapeutic regimen of sodium chlorite; and (b) determining based on the level of LBP whether to continue the therapeutic regimen of sodium chlorite.

In some embodiments, the method further comprises determining to discontinue the regimen of sodium chlorite. In some embodiments, the method further comprises determining to continue the regimen of sodium chlorite.

Disclosed herein are methods comprising: (a) obtaining a first level of one or more biomarkers of a subject who has ALS, wherein the first level of first level of one or more biomarkers of the subject who has ALS is based on a blood assay; (b) based at least in part on the first level of one or more biomarkers of the subject, starting the subject on a regimen of sodium chlorite administration for a time period of about six months; (c) after the time period, obtaining a second level of one or more biomarkers of the subject; (d) determining that the second level of one or more biomarkers in the subject is lower than the first level of one or more biomarkers in the subject by a predetermined threshold amount; and (e) based at least in part on the determining that the second level of one or more biomarkers in the subject is lower than the first level of one or more biomarkers in the subject by the predetermined threshold amount, recommending that the subject continue the regimen of sodium chlorite administration.

In some embodiments, the method comprises: (a) obtaining a first level of inflammatory macrophages in a gut epithelium of a subject who has ALS, wherein the first level of inflammatory macrophages in the gut epithelium of the subject who has ALS is based on a blood assay; (b) based at least in part on the first level of inflammatory macrophages in the gut epithelium of the subject, starting the subject on a regimen of sodium chlorite administration for a time period of about six months; (c) after the time period, obtaining a second level of inflammatory macrophages in the gut epithelium of the subject; (d) determining that the second level of inflammatory macrophages in the gut epithelium of the subject is lower than the first level of inflammatory macrophages in the gut epithelium of the subject by a predetermined threshold amount; and (e) based at least in part on the determining that the second level of inflammatory macrophages in the gut epithelium of the subject is lower than the first level of inflammatory macrophages in the gut epithelium of the subject by the predetermined threshold amount, recommending that the subject continue the regimen of sodium chlorite administration.

In some embodiments, the method comprises: (a) obtaining a first level of LBP of a subject who has ALS, wherein the first level of LBP of the subject who has ALS is based on a blood assay; (b) based at least in part on the first level of LBP of the subject, starting the subject on a regimen of sodium chlorite administration for a time period of at least about six months; (c) after the time period, obtaining a second level of LBP of the subject; (d) determining that the second level of LBP is lower than the first level of LBP of the subject by a predetermined threshold amount; and (e) based at least in part on the determining that the second level of LBP of the subject is lower than the first level of LBP of the subject by the predetermined threshold amount, recommending that the subject continue the regimen of sodium chlorite administration.

Disclosed herein are methods comprising: (a) obtaining a first level of one or more biomarkers of a subject who has ALS, wherein the first level of first level of one or more biomarkers of the subject who has ALS is based on a blood assay; (b) based at least in part on the first level of one or more biomarkers of the subject, starting the subject on a regimen of sodium chlorite administration for a time period of about six months; (c) after the time period, obtaining a second level of one or more biomarkers of the subject; (d) determining that the second level of one or more biomarkers in the subject is lower than the first level of one or more biomarkers in the subject by a predetermined threshold amount; and (e) based at least in part on the determining that the second level of one or more biomarkers in the subject is higher than the first level of one or more biomarkers in the subject by the predetermined threshold amount, recommending that the subject continue the regimen of sodium chlorite administration.

In some embodiments, the method comprises: (a) obtaining a first level of TGFB1 of a subject who has ALS, wherein the first level of TGFB1 of the subject who has ALS is based on a blood assay; (b) based at least in part on the first level of TGFB1 of the subject, starting the subject on a regimen of sodium chlorite administration for a time period of at least about six months; (c) after the time period, obtaining a second level of TGFB1 of the subject; (d) determining that the second level of TGFB1 is higher than the first level of TGFB1 of the subject by a predetermined threshold amount; and (e) based at least in part on the determining that the second level TGFB1 of the subject is higher than the first level of TGFB1 of the subject by the predetermined threshold amount, recommending that the subject continue the regimen of sodium chlorite administration.

Disclosed herein are methods comprising obtaining a first level of one or more biomarkers in a subject who has ALS, wherein the first level of first level of one or more biomarkers of the subject who has ALS is based on a blood assay; (b) based at least in part on the first level of one or more biomarkers of the subject, starting the subject on a regimen of sodium chlorite administration for a time period of about six months; (c) after the time period, obtaining a second level of one or more biomarkers of the subject; (d) determining that the second level of one or more biomarkers in the subject is a decrease of at least a predetermined threshold amount in comparison to the first level of one or more biomarkers in the subject by a predetermined threshold amount; and (e) based at least in part on the determining that the second level of one or more biomarkers in the subject is a decrease of at least a predetermined threshold amount in comparison to the first level of one or more biomarkers in the subject by the predetermined threshold amount, recommending that the subject continue the regimen of sodium chlorite administration.

In some embodiments, the method comprises: (a) obtaining a first plasma neurofilament light chain level of a subject who has ALS, wherein the first plasma neurofilament light chain level of the subject who has ALS is based on a blood assay; (b) based at least in part on the first plasma neurofilament light chain level of the subject, starting the subject on a regimen of sodium chlorite administration for a time period of about six months; (c) after the time period, obtaining a second plasma neurofilament light chain level of the subject; (d) determining that the second plasma neurofilament light chain level of the subject is a decrease of at least a predetermined threshold amount in comparison to the first plasma neurofilament light chain level of the subject; and (e) based at least in part on the determining that the second plasma neurofilament light chain level of the subject is a decrease of at least the predetermined threshold amount in comparison to the first plasma neurofilament light chain level of the subject, recommending that the subject continue the regimen of sodium chlorite administration.

In some embodiments, the method comprises a method of treating ALS in a subject in need thereof, the method comprising: (a) obtaining a first level of a first biomarker in the subject; (b) obtaining a first level of the second biomarker in the subject; (c) after obtaining the first level of the first biomarker in the subject and obtaining the first level of the second biomarker in the subject, starting the subject on a regimen of sodium chlorite administration for a time period of at least about six months; (d) after the time period, obtaining a second level of the first biomarker in the subject; (e) after the time period, obtaining a second level of the second biomarker in the subject; (f) determining that the first level of the first biomarker in the subject is greater than the second level of the first biomarker in the subject; (g) determining that the first level of the second biomarker in the subject is lesser than the second level of the second biomarker in the subject; and (h) based at least in part on the determining that the first level of the first biomarker in the subject is greater than the second level of the first biomarker in the subject and the determining that the first level of the second biomarker in the subject is lesser than the second level of the second biomarker in the subject, recommending that the subject continue the regimen of sodium chlorite administration.

In some embodiments, the determining that the first level of the first biomarker in the subject is greater than the second level of the first biomarker is done by obtaining a result from an assay of the subject.

In some embodiments, the determining that the first level of the second biomarker in the subject is lesser than the second level of the second biomarker is done by obtaining a result from an assay of the subject.

In some embodiments, the determining the ratio of LPS:EGF in the subject is done by obtaining a result from an assay of the subject.

In some embodiments, the identifying that the subject has the ratio of LPS:EGF associated with ALS is done by obtaining a result from an assay of the subject. In some embodiments, the identifying that the subject has the level of TGFB1 associated with ALS is done by obtaining a result from an assay of the subject. In some embodiments, the identifying that the subject has the level of LBP associated with ALS is done by obtaining a result from an assay of the subject.

In some embodiments, the method further comprises performing the assay of the subject to obtain the result. In some embodiments, the assay is a blood assay.

In some embodiments, the assay is a quantification of LPS and EGF in blood of the subject by high performance liquid chromatography. In some embodiments, the assay is a quantification of TGFB1 in blood of the subject by high performance liquid chromatography. In some embodiments, the assay is a quantification of LBP in blood of the subject by high performance liquid chromatography. In some embodiments, the assay is a quantification of the first biomarker and the second biomarker in blood of the subject by high performance liquid chromatography.

In some embodiments, the blood assay is a quantification of LPS and EGF in blood of the subject by high performance liquid chromatography. In some embodiments, the blood assay is a quantification of TGFB1 in blood of the subject by high performance liquid chromatography. In some embodiments, the blood assay is a quantification of LBP in blood of the subject by high performance liquid chromatography. In some embodiments, the blood assay is a quantification of neurofilament light chain levels in blood of the subject by high performance liquid chromatography.

In some embodiments, the biomarker is selected from A2M, CRP, LPS, EGF, IL-10, IL-18, HGF, HLA-DR, LBP, NFkB, SAA, SOD1, sCD163, TauCl, TDP43, TGFB1, and a combination thereof. In some embodiments, the biomarker is selected from A2M, CRP, LPS, EGF, TGFB1, LBP, and a combination thereof. In some embodiments, the biomarker is selected from LPS, EGF, TGFB1, LBP, and a combination thereof. In some embodiments, the biomarker is selected from LPS and EGF. In some embodiments, the biomarker is LPS. In some embodiments, the biomarker is EGF. In some embodiments, the biomarker is TGFB1. In some embodiments, the biomarker is LBP. In some embodiments, the biomarker is CRP.

In some embodiments, the first biomarker is LPS.

In some embodiments, the second biomarker is EGF.

In some embodiments, the ratio of LPS:EGF associated with ALS is no greater than 50. In some embodiments, the ratio of LPS:EGF associated with ALS is no greater than 45. In some embodiments, the ratio of LPS:EGF associated with ALS is no greater than 40.

A subject for a therapy herein can be of any suitable age, for example, at least 30 years old, at least 35 years old, at least 40 years old, at least 45 years old, at least 50 years old, at least years old, at least 60 years old, 40 to 80 years old, 40 to 75 years old, 40 to 70 years old, 40 to years old, 40 to 60 years old, 40 to 55 years old, 40 to 50 years old, no greater than 80 years old, no greater than 75 years old, no greater than 70 years old, no greater than 65 years old, or no greater than 80 years old.

A subject described herein can be of any suitable age. In some embodiments, the subject is at least age 40, at least age 41, at least age 42, at least age 43, at least age 44, at least age 45, at least age 46, at least age 47, at least age 48, at least age 49, at least age 50, at least age 51, at least age 52, at least age 53, at least age 54, at least age 55, at least age 56, at least age 57, at least age 58, at least age 59, at least age 60, at least age 61, at least age 62, at least age 63, at least age 64, or at least age 65. In some embodiments, the subject is at least age 40, at least age 41, at least age 42, at least age 43, at least age 44, at least age 45, at least age 46, at least age 47, at least age 48, at least age 49, or at least age 50. In some embodiments, the subject is at least age 51, at least age 52, at least age 53, at least age 54, at least age 55, at least age 56, at least age 57, at least age 58, at least age 59, at least age 60, at least age 61, at least age 62, at least age 63, at least age 64, or at least age 65. In some embodiments, the subject is at least age 40. In some embodiments, the subject is at least age 41. In some embodiments, the subject is at least age 42. In some embodiments, the subject is at least age 43. In some embodiments, the subject is at least age 44. In some embodiments, the subject is at least age 44. In some embodiments, the subject is at least age 45. In some embodiments, the subject is at least age 46. In some embodiments, the subject is at least age 47. In some embodiments, the subject is at least age 48. In some embodiments, the subject is at least age 49. In some embodiments, the subject is at least age 50. In some embodiments, the subject is at least age 51. In some embodiments, the subject is at least age 52. In some embodiments, the subject is at least age 53. In some embodiments, the subject is at least age 54. In some embodiments, the subject is at least age 55. In some embodiments, the subject is at least age 56. In some embodiments, the subject is at least age 57. In some embodiments, the subject is at least age 58. In some embodiments, the subject is at least age 59. In some embodiments, the subject is at least age 60. In some embodiments, the subject is at least age 61. In some embodiments, the subject is at least age 62. In some embodiments, the subject is at least age 63. In some embodiments, the subject is at least age 64. In some embodiments, the subject is at least age 65.

In some embodiments, the subject is no greater than age 40, no greater than age 41, no greater than age 42, no greater than age 43, no greater than age 44, no greater than age 45, no greater than age 46, no greater than age 47, no greater than age 48, no greater than age 49, no greater than age 50, no greater than age 51, no greater than age 52, no greater than age 53, no greater than age 54, no greater than age 55, no greater than age 56, no greater than age 57, no greater than age 58, no greater than age 59, no greater than age 60, no greater than age 61, no greater than age 62, no greater than age 63, no greater than age 64, or no greater than age 65. In some embodiments, the subject is no greater than age 41, no greater than age 42, no greater than age 43, no greater than age 44, no greater than age 45, no greater than age 46, no greater than age 47, no greater than age 48, no greater than age 49, or no greater than age 50. In some embodiments, the subject is no greater than age 51, no greater than age 52, no greater than age 53, no greater than age 54, no greater than age 55, no greater than age 56, no greater than age 57, no greater than age 58, no greater than age 59, no greater than age 60, no greater than age 61, no greater than age 62, no greater than age 63, no greater than age 64, or no greater than age 65. In some embodiments, the subject is no greater than age 40. In some embodiments, the subject is no greater than age 41. In some embodiments, the subject is no greater than age 42. In some embodiments, the subject is no greater than age 43. In some embodiments, the subject is no greater than age 44. In some embodiments, the subject is no greater than age 44. In some embodiments, the subject is no greater than age 45. In some embodiments, the subject is no greater than age 46. In some embodiments, the subject is no greater than age 47. In some embodiments, the subject is no greater than age 48. In some embodiments, the subject is no greater than age 49. In some embodiments, the subject is no greater than age 50. In some embodiments, the subject is no greater than age 51. In some embodiments, the subject is no greater than age 52. In some embodiments, the subject is no greater than age 53. In some embodiments, the subject is no greater than age 54. In some embodiments, the subject is no greater than age 55. In some embodiments, the subject is no greater than age 56. In some embodiments, the subject is no greater than age 57. In some embodiments, the subject is no greater than age 58. In some embodiments, the subject is no greater than age 59. In some embodiments, the subject is no greater than age 60. In some embodiments, the subject is no greater than age 61. In some embodiments, the subject is no greater than age 62. In some embodiments, the subject is no greater than age 63. In some embodiments, the subject is no greater than age 64. In some embodiments, the subject is no greater than age 65.

In some embodiments, the subject is about age 40, about age 41, about age 42, about age 43, about age 44, about age 45, about age 46, about age 47, about age 48, about age 49, about age 50, about age 51, about age 52, about age 53, about age 54, about age 55, about age 56, about age 57, about age 58, about age 59, about age 60, about age 61, about age 62, about age 63, about age 64, or about age 65. In some embodiments, the subject is about age 40, about age 41, about age 42, about age 43, about age 44, about age 45, about age 46, about age 47, about age 48, about age 49, or about age 50. In some embodiments, the subject is about age 51, about age 52, about age 53, about age 54, about age 55, about age 56, about age 57, about age 58, about age 59, about age 60, about age 61, about age 62, about age 63, about age 64, or about age 65. In some embodiments, the subject is about age 40. In some embodiments, the subject is about age 41. In some embodiments, the subject is about age 42. In some embodiments, the subject is about age 43. In some embodiments, the subject is about age 44. In some embodiments, the subject is about age 44. In some embodiments, the subject is about age 45. In some embodiments, the subject is about age 46. In some embodiments, the subject is about age 47. In some embodiments, the subject is about age 48. In some embodiments, the subject is about age 49. In some embodiments, the subject is about age 50. In some embodiments, the subject is about age 51. In some embodiments, the subject is about age 52. In some embodiments, the subject is about age 53. In some embodiments, the subject is about age 54. In some embodiments, the subject is about age 55. In some embodiments, the subject is about age 56. In some embodiments, the subject is about age 57. In some embodiments, the subject is about age 58. In some embodiments, the subject is about age 59. In some embodiments, the subject is about age 60. In some embodiments, the subject is about age 61. In some embodiments, the subject is about age 62. In some embodiments, the subject is about age 63. In some embodiments, the subject is about age 64. In some embodiments, the subject is about age 65.

In some embodiments, the subject has a neurodegenerative disease. In some embodiments, the subject has ALS. In some embodiments, the subject has Alzheimer's disease. In some embodiments, the subject has Parkinson's disease.

In some embodiments, the subject possesses a CRP level greater than 1.13 mg/L as determined by a blood assay. In some embodiments, the subject possesses a CRP level greater than 1.15 mg/L as determined by a blood assay. In some embodiments, the subject possesses a CRP level greater than 1.17 mg/L as determined by a blood assay. In some embodiments, the subject possesses a CRP level greater than 1.2 mg/L as determined by a blood assay. In some embodiments, the subject possesses a CRP level greater than 1.5 mg/L as determined by a blood assay. In some embodiments, the subject possesses a CRP level greater than 2 mg/L as determined by a blood assay. In some embodiments, the subject possesses a CRP level greater than 2.5 mg/L as determined by a blood assay. In some embodiments, the subject possesses a CRP level greater than 3 mg/L as determined by a blood assay. In some embodiments, the subject possesses a CRP level greater than 3.5 mg/L as determined by a blood assay. In some embodiments, the subject possesses a CRP level greater than 4 mg/L as determined by a blood assay.

In some embodiments, the subject is administered an amount of sodium chlorite. In some embodiments, the subject is administered an amount of sodium chlorite that is therapeutically effective for ALS.

In some embodiments, the amount is about 0.2 mg/kg/day to about 3.5 mg/kg/day. In some embodiments, the amount is about 0.5 mg/kg/day to about 3.5 mg/kg/day. In some embodiments, the amount is about 1.0 mg/kg/day to about 3.5 mg/kg/day. In some embodiments, the amount is about 1.5 mg/kg/day to about 3.5 mg/kg/day. In some embodiments, the amount is about 2.0 mg/kg/day to about 3.5 mg/kg/day. In some embodiments, the amount is about 2.5 mg/kg/day to about 3.5 mg/kg/day.

In some embodiments, the amount is about 1.0 mg/kg/day to about 10 mg/kg/day. In some embodiments, the amount is about 2.0 mg/kg/day to about 10 mg/kg/day. In some embodiments, the amount is about 3.0 mg/kg/day to about 10 mg/kg/day. In some embodiments, the amount is about 4.0 mg/kg/day to about 10 mg/kg/day. In some embodiments, the amount is about 5.0 mg/kg/day to about 10 mg/kg/day.

In some embodiments, the amount is about 0.2 mg/kg/day. In some embodiments, the amount is about 0.5 mg/kg/day. In some embodiments, the amount is about 1.0 mg/kg/day. In some embodiments, the amount is about 1.2 mg/kg/day. In some embodiments, the amount is about 1.4 mg/kg/day. In some embodiments, the amount is about 1.6 mg/kg/day. In some embodiments, the amount is about 1.8 mg/kg/day. In some embodiments, the amount is about 2.0 mg/kg/day. In some embodiments, the amount is about 2.2 mg/kg/day. In some embodiments, the amount is about 2.4 mg/kg/day. In some embodiments, the amount is about 2.6 mg/kg/day. In some embodiments, the amount is about 2.8 mg/kg/day. In some embodiments, the amount is about 3.0 mg/kg/day. In some embodiments, the amount is about 3.2 mg/kg/day. In some embodiments, the amount is about 3.5 mg/kg/day.

In some embodiments, the amount is about 4.0 mg/kg/day. In some embodiments, the amount is about 5.0 mg/kg/day. In some embodiments, the amount is about 6.0 mg/kg/day. In some embodiments, the amount is about 7.0 mg/kg/day. In some embodiments, the amount is about 8.0 mg/kg/day. In some embodiments, the amount is about 9.0 mg/kg/day. In some embodiments, the amount is about 10.0 mg/kg/day.

In some embodiments, the administering is oral. In some embodiments, the administering is parenteral. In some embodiments, the administering is intravenous.

In some embodiments, the subject is on a regimen of sodium chlorite. In some embodiments, the regimen of sodium chlorite is about 0.2 mg/kg/day to about 3.5 mg/kg/day. In some embodiments, the regimen of sodium chlorite is about 0.2 mg/kg/day to about 3.5 mg/kg/day. In some embodiments, the regimen of sodium chlorite is about 0.5 mg/kg/day to about 3.5 mg/kg/day. In some embodiments, the regimen of sodium chlorite is about 1.0 mg/kg/day to about 3.5 mg/kg/day. In some embodiments, the regimen of sodium chlorite is about 1.5 mg/kg/day to about 3.5 mg/kg/ day. In some embodiments, the regimen of sodium chlorite is about 2.0 mg/kg/day to about 3.5 mg/kg/day. In some embodiments, the regimen of sodium chlorite is about 2.5 mg/kg/day to about 3.5 mg/kg/day.

In some embodiments, the regimen of sodium chlorite is about 1.0 mg/kg/day to about mg/kg/day. In some embodiments, the regimen of sodium chlorite is about 2.0 mg/kg/day to about 10.0 mg/kg/day. In some embodiments, the regimen of sodium chlorite is about 3.0 mg/kg/day to about 10.0 mg/kg/day. In some embodiments, the regimen of sodium chlorite is about 4.0 mg/kg/day to about 10.0 mg/kg/day. In some embodiments, the regimen of sodium chlorite is about 5.0 mg/kg/day to about 10.0 mg/kg/day.

In some embodiments, the regimen of sodium chlorite is about 0.2 mg/kg/day. In some embodiments, the regimen of sodium chlorite is about 0.5 mg/kg/day. In some embodiments, the regimen of sodium chlorite is about 1.0 mg/kg/day. In some embodiments, the regimen of sodium chlorite is about 1.2 mg/kg/day. In some embodiments, the regimen of sodium chlorite is about 1.4 mg/kg/day. In some embodiments, the regimen of sodium chlorite is about 1.6 mg/kg/day. In some embodiments, the regimen of sodium chlorite is about 1.8 mg/kg/day. In some embodiments, the regimen of sodium chlorite is about 2.0 mg/kg/day. In some embodiments, the regimen of sodium chlorite is about 2.2 mg/kg/day. In some embodiments, the regimen of sodium chlorite is about 2.4 mg/kg/day. In some embodiments, the regimen of sodium chlorite is about 2.6 mg/kg/day. In some embodiments, the regimen of sodium chlorite is about 2.8 mg/kg/day. In some embodiments, the regimen of sodium chlorite is about 3.0 mg/kg/day. In some embodiments, the regimen of sodium chlorite is about 3.2 mg/kg/day. In some embodiments, the regimen of sodium chlorite is about 3.5 mg/kg/day.

In some embodiments, the regimen of sodium chlorite is about 4.0 mg/kg/day. In some embodiments, the regimen of sodium chlorite is about 5.0 mg/kg/day. In some embodiments, the regimen of sodium chlorite is about 6.0 mg/kg/day. In some embodiments, the regimen of sodium chlorite is about 7.0 mg/kg/day. In some embodiments, the regimen of sodium chlorite is about 8.0 mg/kg/day. In some embodiments, the regimen of sodium chlorite is about 9.0 mg/kg/day. In some embodiments, the regimen of sodium chlorite is about 10.0 mg/kg/day.

In some embodiments, the regimen of sodium chlorite is administered orally. In some embodiments, the regimen of sodium chlorite is administered parenterally. In some embodiments, the regimen of sodium chlorite is administered intravenously.

In some embodiments, the subject is undergoing a treatment for ALS, wherein the treatment is a therapeutic regimen of sodium chlorite. In some embodiments, the method further comprises determining to discontinue the therapeutic regimen of sodium chlorite. In some embodiments, the method further comprises determining to continue the therapeutic regimen of sodium chlorite.

In some embodiments, the therapeutic regimen of sodium chlorite is about 0.2 mg/kg/day to about 3.5 mg/kg/day. In some embodiments, the therapeutic regimen of sodium chlorite is about 0.2 mg/kg/day to about 3.5 mg/kg/day. In some embodiments, the therapeutic regimen of sodium chlorite is about 0.5 mg/kg/day to about 3.5 mg/kg/day. In some embodiments, the therapeutic regimen of sodium chlorite is about 1.0 mg/kg/day to about 3.5 mg/kg/day. In some embodiments, the therapeutic regimen of sodium chlorite is about 1.5 mg/kg/day to about 3.5 mg/kg/day. In some embodiments, the therapeutic regimen of sodium chlorite is about 2.0 mg/kg/day to about 3.5 mg/kg/day. In some embodiments, the therapeutic regimen of sodium chlorite is about 2.5 mg/kg/day to about 3.5 mg/kg/day.

In some embodiments, the therapeutic regimen of sodium chlorite is about 1.0 mg/kg/day to about 10.0 mg/kg/day. In some embodiments, the therapeutic regimen of sodium chlorite is about 2.0 mg/kg/day to about 10.0 mg/kg/day. In some embodiments, the therapeutic regimen of sodium chlorite is about 3.0 mg/kg/day to about 10.0 mg/kg/day. In some embodiments, the therapeutic regimen of sodium chlorite is about 4.0 mg/kg/day to about 10.0 mg/kg/day. In some embodiments, the therapeutic regimen of sodium chlorite is about 5.0 mg/kg/day to about 10.0 mg/kg/day.

In some embodiments, the therapeutic regimen of sodium chlorite is about 0.2 mg/kg/day. In some embodiments, the therapeutic regimen of sodium chlorite is about 0.5 mg/kg/day. In some embodiments, the therapeutic regimen of sodium chlorite is about 1.0 mg/kg/day. In some embodiments, the therapeutic regimen of sodium chlorite is about 1.2 mg/kg/day. In some embodiments, the therapeutic regimen of sodium chlorite is about 1.4 mg/kg/day. In some embodiments, the therapeutic regimen of sodium chlorite is about 1.6 mg/kg/day. In some embodiments, the therapeutic regimen of sodium chlorite is about 1.8 mg/kg/day. In some embodiments, the therapeutic regimen of sodium chlorite is about 2.0 mg/kg/day. In some embodiments, the therapeutic regimen of sodium chlorite is about 2.2 mg/kg/day. In some embodiments, the therapeutic regimen of sodium chlorite is about 2.4 mg/kg/day. In some embodiments, the therapeutic regimen of sodium chlorite is about 2.6 mg/kg/day. In some embodiments, the therapeutic regimen of sodium chlorite is about 2.8 mg/kg/day. In some embodiments, the therapeutic regimen of sodium chlorite is about 3.0 mg/kg/day. In some embodiments, the therapeutic regimen of sodium chlorite is about 3.2 mg/kg/day. In some embodiments, the therapeutic regimen of sodium chlorite is about 3.5 mg/kg/day.

In some embodiments, the therapeutic regimen of sodium chlorite is about 4.0 mg/kg/day. In some embodiments, the therapeutic regimen of sodium chlorite is about 5.0 mg/kg/day. In some embodiments, the therapeutic regimen of sodium chlorite is about 6.0 mg/kg/day. In some embodiments, the therapeutic regimen of sodium chlorite is about 7.0 mg/kg/day. In some embodiments, the therapeutic regimen of sodium chlorite is about 8.0 mg/kg/day. In some embodiments, the therapeutic regimen of sodium chlorite is about 9.0 mg/kg/day. In some embodiments, the therapeutic regimen of sodium chlorite is about 10.0 mg/kg/day.

In some embodiments, the therapeutic regimen of sodium chlorite is administered orally. In some embodiments, the therapeutic regimen of sodium chlorite is administered parenterally. In some embodiments, the therapeutic regimen of sodium chlorite is administered intravenously.

In some embodiments, the subject is undergoing sodium chlorite therapy. In some embodiments, the sodium chlorite therapy is about 0.2 mg/kg/day to about 3.5 mg/kg/day. In some embodiments, the sodium chlorite therapy is about 0.2 mg/kg/day to about 3.5 mg/kg/day. In some embodiments, the sodium chlorite therapy is about 0.2 mg/kg/day to about 3.5 mg/kg/day. In some embodiments, the sodium chlorite therapy is about 0.5 mg/kg/day to about 3.5 mg/kg/day. In some embodiments, the sodium chlorite therapy is about 1.0 mg/kg/day to about 3.5 mg/kg/day. In some embodiments, the sodium chlorite therapy is about 1.5 mg/kg/day to about 3.5 mg/kg/day. In some embodiments, the sodium chlorite therapy is about 2.0 mg/kg/day to about 3.5 mg/kg/day. In some embodiments, the sodium chlorite therapy is about 2.5 mg/kg/day to about 3.5 mg/kg/day.

In some embodiments, the sodium chlorite therapy is about 1.0 mg/kg/day to about 10.0 mg/kg/day. In some embodiments, the sodium chlorite therapy is about 2.0 mg/kg/day to about 10.0 mg/kg/day. In some embodiments, the sodium chlorite therapy is about 3.0 mg/kg/day to about 10.0 mg/kg/day. In some embodiments, the sodium chlorite therapy is about 4.0 mg/kg/day to about 10.0 mg/kg/day. In some embodiments, the sodium chlorite therapy is about 5.0 mg/kg/day to about 10.0 mg/kg/day.

In some embodiments, the sodium chlorite therapy is about 0.2 mg/kg/day. In some embodiments, the sodium chlorite therapy is about 0.5 mg/kg/day. In some embodiments, the sodium chlorite therapy is about 1.0 mg/kg/day. In some embodiments, the sodium chlorite therapy is about 1.2 mg/kg/day. In some embodiments, the sodium chlorite therapy is about 1.4 mg/kg/day. In some embodiments, the sodium chlorite therapy is about 1.6 mg/kg/day. In some embodiments, the sodium chlorite therapy is about 1.8 mg/kg/day. In some embodiments, the sodium chlorite therapy is about 2.0 mg/kg/day. In some embodiments, the sodium chlorite therapy is about 2.2 mg/kg/day. In some embodiments, the sodium chlorite therapy is about 2.4 mg/kg/day. In some embodiments, the sodium chlorite therapy is about 2.6 mg/kg/day. In some embodiments, the sodium chlorite therapy is about 2.8 mg/kg/day. In some embodiments, the sodium chlorite therapy is about 3.0 mg/kg/day. In some embodiments, the sodium chlorite therapy is about 3.2 mg/kg/day. In some embodiments, the sodium chlorite therapy is about 3.5 mg/kg/day.

In some embodiments, the sodium chlorite therapy is about 4.0 mg/kg/day. In some embodiments, the sodium chlorite therapy is about 5.0 mg/kg/day. In some embodiments, the sodium chlorite therapy is about 6.0 mg/kg/day. In some embodiments, the sodium chlorite therapy is about 7.0 mg/kg/day. In some embodiments, the sodium chlorite therapy is about 8.0 mg/kg/day. In some embodiments, the sodium chlorite therapy is about 9.0 mg/kg/day. In some embodiments, the sodium chlorite therapy is about 10.0 mg/kg/day.

In some embodiments, the method further comprises administering to the subject the sodium chlorite therapy. In some embodiments, the method further comprises orally administering to the subject the sodium chlorite therapy. In some embodiments, the method further comprises parenterally administering to the subject the sodium chlorite therapy. In some embodiments, the method further comprises intravenously administering to the subject the sodium chlorite therapy.

A subject can be monitored for biomarkers for a condition prior to, during, or after receiving therapy for the neurodegenerative disease. For example, a subject who received, is receiving, or is recommended to receive sodium chlorite therapy for ALS can be monitored for biomarkers associated with the condition and the therapy.

Non-limiting examples of biomarkers relevant to the therapies herein include liposaccharide (LPS) and wound healing epidermal growth factor (EGF). Monitoring the levels of these biomarkers in a subject, for example, by HPLC analysis of blood draws, can provide information useful for therapeutic decisions. For example, a decision to begin therapy, continue therapy, or end therapy can be based on monitoring the levels of biomarkers in a subject, and by evaluating the ratio of the levels of the biomarkers in the subject over time. A decreasing ratio of LPS:EGF over time can be associated with successful therapy.

In some embodiments, the biomarker is transforming growth factor beta 1 (TGFB1). In some embodiments, TGFB1 acts as a surrogate marker for alpha 2 macroglobulin (A2M) activation into a dimeric form. In some embodiments, the biomarker regulates the innate immune system.

Figure 2:
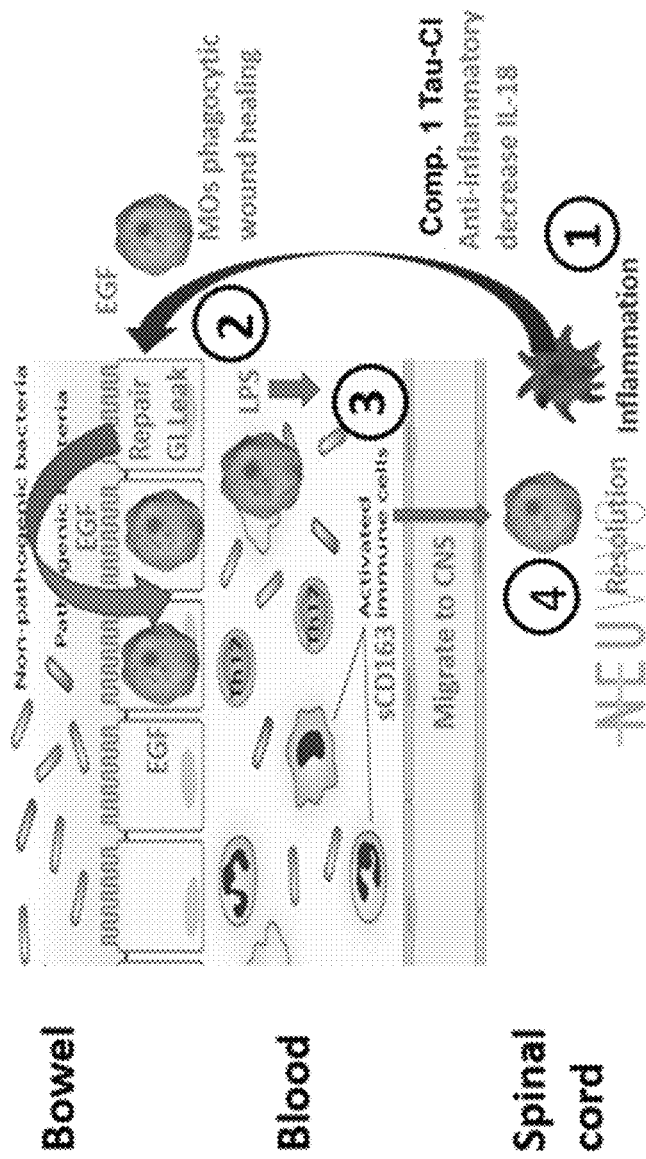
FIG. 2 shows ALS pathogenesis in the presence of NP001.

FIG. 1 illustrates pathogenesis of ALS. FIG. 2 illustrates the same pathway when treated with Compound 1 (sodium chlorite). The figure indicates where EGF and LPS participate in the pathway.

Compounds of the Disclosure

Disclosed herein are oxidative agents that can treat a condition with immune system dysregulation. In some embodiments, an oxidative agent of the disclosure can treat a condition with immune system dysregulation by inactivating macrophages. In some embodiments, the compound of the disclosure can be rapidly converted into a regulator of NFkB activation.

In some embodiments, the compound of the disclosure is chlorite ($ClO_2^-$) or a pharmaceutically-acceptable salt thereof. In some embodiments, the compound of the disclosure is sodium chlorite ($NaClO_2$). In some embodiments, the compound of the disclosure is potassium chlorite ($KClO_2$). In some embodiments, sodium chlorite can be converted from a prodrug to an intracellular form of taurine chloramine (TauCl) via a hyperchlorite intermediate. TauCl is a long-lived effector molecule within macrophages that down-regulates NF-kB expression and inhibits production of pro-inflammatory cytokines in part through activation of heme oxygenase-1 (HO-1).

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure. In some embodiments, a compound of the disclosure can be at least about 90% pure. In some embodiments, a compound of the disclosure can be at least about 95% pure. In some embodiments, a compound of the disclosure can be at least about 98% pure. In some embodiments, a compound of the disclosure can be at least about 99% pure. In some embodiments, a compound of the disclosure can be at least about 99.5% pure. In some embodiments, a compound of the disclosure can be at least about 99.8% pure.

Chlorite Compositions

In some embodiments, the sodium chlorite described herein is an aqueous pharmaceutical formulation. In some embodiments, the aqueous pharmaceutical formulation comprises sodium chlorite and a saline solution.

In various embodiments, the pH of the aqueous pharmaceutical formulation is about 7 to about 11. In some embodiments, the pH of the aqueous pharmaceutical formulation is about 7 to about 9.5. In some embodiments, the aqueous pharmaceutical formulation includes a buffer. Non-limiting examples of buffers include phosphate buffers, borate buffers, citrate buffers, and carbonate buffers. In some embodiments, the buffer is a phosphate buffer such as monosodium phosphate or disodium phosphate. In some embodiments, any of the formulations or pharmaceutical formulations described herein comprises a pH adjusting agent that consists essentially of a phosphate salt or a mixture of phosphate salts.

In some embodiments, the pH of a chlorite formulation for use with the present disclosure can be adjusted to between about 7 and about 11.5. In some embodiments, the pH of a chlorite formulation is lowered to between about 7 and about 11.5 using a pH adjusting compound that does not expose the formulation to high local acidity. In some embodiments, the pH adjusting compound is any one or more of monosodium phosphate, disodium phosphate, or acetic acid.

In some embodiments, the pH adjusting agent(s) or pH adjusting compound(s) are weak acids or weak bases having a pKa of about 4 to about 9, a pKa of about 5 to about 9, or a pKa of about 5 to about 8, or a pKa of about 6 to about 7.5. Examples include, but are not limited to a phosphate buffer having a pKa of about 4 to about 9, for example, monobasic phosphates, or monosodium phosphate and/or disodium phosphate and lower alkanoic acids, for example, acetic acid or propionic acid. In some embodiments, the pH of a formulation sensitive to acidity is lowered to between about 7 and about 11.5 using a pH adjusting compound that does not expose the formulation to acidity, including but not limited to a high local acidity in the area around the pH adjusting compound. In some embodiments, the pH of a formulation sensitive to acidity is lowered to between about 7 and about 10 using a pH adjusting compound that does not expose the formulation to acidity, including but not limited to a high local acidity in the area around the pH adjusting compound. In some embodiments, the pH of a formulation sensitive to acidity is lowered to between about 7 and about 9.5 using a pH adjusting compound that does not expose the formulation to acidity, including but not limited to a high local acidity in the area around the pH adjusting compound. In some embodiments, the pH of a formulation sensitive to acidity is lowered to between about 7 and about 9.0 using a pH adjusting compound that does not expose the formulation to acidity, including but not limited to a high local acidity in the area around the pH adjusting compound. In some embodiments, the pH of a formulation sensitive to acidity is lowered to between about 7 and about 8.5 using a pH adjusting compound that does not expose the formulation to acidity, including but not limited to a high local acidity in the area around the pH adjusting compound. In some embodiments, the pH of a formulation sensitive to acidity is lowered to between about 7.1 and about 7.7 using a pH adjusting compound that does not expose the formulation to acidity, including but not limited to a high local acidity in the area around the pH adjusting compound.

Injectable preparations, for example, sterile injectable aqueous or oleaginous suspensions can be formulated, for example, using suitable dispersing or wetting agents and suspending agents. An injectable preparation can be a sterile, injectable solution, suspension, or emulsion in a nontoxic, parenterally-acceptable diluent or solvent, for example, as a solution in 1,3-butanediol. Non-limiting examples of suitable vehicles and solvents include Water for Injection (WFI, USP), Sterile Water for Injection (SWFI, USP), Ringer's solution, USP, and isotonic solution, such as isotonic sodium chloride solution. In some embodiments, a sterile, fixed oil is used as a solvent or suspending medium. In some embodiments, a fatty acids such as oleic acid is formulated in an injectable.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use. In some embodiments, the injectable formulations are sterile, pyrogen free, and free of particulates according to USP-NF standards. In some embodiments, sterility, pyrogenicity, and particulates assays are conducted according to USP-NF protocols.

In some embodiments, the pharmaceutically acceptable chlorite salt is administered in an amount ranging from 0.1 to 10 mg/kg body mass. In some embodiments, the chlorite salt is administered more than once in a month, such as at least once per week for a period of at least one month. In some embodiments, the chlorite salt is administered for at least a year.

In some embodiments, the chlorite formulations for use with the present invention comprise low amounts of chlorate ion, sulfate ion, or chloride ion. In some embodiments, the composition is substantially free of sulfate ion.

In some embodiments, a formulation herein contains an amount of chloride ions than is less than about 1.9% of the chlorite ions by mass in the formulation, for example, less than about 1.8%; less than about 1.5%; less than about 1.0%; less than about 0.5%; less than about 0.3%; less than about 0.1%; less than about 0.05%; less than about 0.01%; less than about 0.001%; from about 0.001 to about 0.1%; from about 0.1 to about 0.5%; from about 0.5 to about 1.0%; from about 1.0 to about 1.5%; or from about 1.5 to about 1.8%.

In some embodiments, a formulation herein contains less than an amount of chlorate ions that is less than about 1.5% of chlorate ions by mass in the formulation, for example, less than about 1.4%, less than about 1.3%; less than about 1.0%; less than about 0.5%; less than about 0.3%; less than about 0.1%; less than about 0.01%; less than about 0.001%; from about to about 0.1%; from about 0.001 to about 0.01%; from about 0.01 to about 0.1%; from about 0.1 to about 0.5%; from about 0.5 to about 1.0%; or from about 1.0 to about 1.4% of chlorate ions. In some embodiments, a formulation herein is substantially free of chlorate ions. In some embodiments, a formulation herein contains less than about 0.5% of chlorate ions by mass in the formulation. In some embodiments, a formulation herein contains less than about 0.19% of chlorate ions by mass in the formulation. In some embodiments, a formulation herein contains less than about 0.1% of chlorate ions by mass in the formulation. In some embodiments, the level of chlorate ions is below the level of detection using HPLC.

In some embodiments, a formulation herein contains less than an amount of sulfate ions that is less than about 0.7% of sulfate ions by mass in the formulation, for example, less than about 0.65%, less than about 0.6%; less than about 0.5%; less than about 0.4%; less than about less than about 0.2%; less than about 0.1%; less than about 0.08%; less than about 0.07%; less than about 0.06%; less than about 0.05%; less than about 0.005%; less than about 0.0005%; from about 0.001 to about 0.1%; from about 0.01 to about 1%; from about 0.01 to about 0.5%; from about 0.06 to about 0.08%; or from about 0.5 to about 0.65%. In some embodiments, a formulation herein is substantially free of sulfate ions. In some embodiments, a formulation herein contains less than about 0.5% of sulfate ions by mass in the formulation. In some embodiments, a formulation herein contains less than about 0.08% of sulfate ions by mass in the formulation. In some embodiments, the level of sulfate ions is below the level of detection using HPLC.

In some embodiments, a formulation herein contains less than an amount of chloride ions that is less than about 0.5% of chloride ions by mass in the formulation, for example, less than about 0.24%, less than about 0.2%; or less than about 0.1%. In some embodiments, a formulation herein contains less than about 0.2% of chloride ions by mass in the formulation. In some embodiments, a formulation herein contains less than about 0.1% of chloride ions by mass in the formulation. In some embodiments, the level of chloride ions is below the level of detection using HPLC.

In some embodiments, the chlorite formulations described herein comprise no greater than about 10% by weight of by products or impurities present in commercially available technical grade chlorite. Non-limiting examples of by-products or impurities present in commercially available technical grade chlorite include chlorate, sulfate, chlorine dioxide, chloride, sodium bicarbonate, and sodium carbonate. In some embodiments, the chlorite formulations described herein comprise no greater than about any of 15%, about 12%, about 10%, about 9%, about 8%, about 7%, about 6%, about 5%, about 4%, about 3%, about 2%, about 1%, about 0.5%, about 0.3%, about 0.1%, between about 0.1 to about 5%; between about 5 to about 10%; or between about 10 to about 15% by weight of one or more degradation products or impurities present in commercially available technical grade sodium chlorite. In some embodiments, the chlorite formulations described herein comprise no greater than about 0.5% by weight of degradation products or impurities present in commercially available technical grade sodium chlorite. In some embodiments, the chlorite formulations described herein comprise no greater than about 5% by weight of degradation products or impurities present in commercially available technical grade sodium chlorite. In some embodiments, the sodium chlorite formulations described herein are substantially free of the degradation products or impurities present in commercially available technical grade sodium chlorite.

In some embodiments, the chlorite formulations described herein comprise purified sodium chlorite. In some embodiments, the chlorite formulations described herein comprise purified sodium chlorite, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5.

In some embodiments, the chlorite formulations described herein comprise purified sodium chlorite, wherein the purified sodium chlorite comprises no more than about 1.0% sodium chloride, wherein the purified sodium chlorite comprises no more than about 1.0% sodium chlorate, and wherein the chlorite composition comprises a buffer and has a pH between about 7 and about 8. In some embodiments, the chlorite formulations described herein comprise purified sodium chlorite, wherein the purified sodium chlorite comprises no more than about sodium chloride, wherein the purified sodium chlorite comprises no more than about 0.8% sodium chlorate, and wherein the chlorite composition comprises a buffer and has a pH between about 7 and about 8. In some embodiments, the chlorite formulations described herein comprise purified sodium chlorite, wherein the purified sodium chlorite comprises no more than about sodium chloride, wherein the purified sodium chlorite comprises no more than about 0.6% sodium chlorate, and wherein the chlorite composition comprises a buffer and has a pH between about 7 and about 8. In some embodiments, the chlorite formulations described herein comprise purified sodium chlorite, wherein the purified sodium chlorite comprises no more than about sodium chloride, wherein the purified sodium chlorite comprises no more than about 0.5% sodium chlorate, and wherein the chlorite composition comprises a buffer and has a pH between about 7 and about 8. In some embodiments, the chlorite formulations described herein comprise purified sodium chlorite, wherein the purified sodium chlorite comprises no more than about sodium chloride, wherein the purified sodium chlorite comprises no more than about 0.5% sodium chlorate, and wherein the chlorite composition comprises a buffer and has a pH between about 7.5 and about 7.7.

The regimen of administration can involve administration in an amount and at a frequency to provide a desired effect. For example, chlorite or a chlorite-containing agent can be administered for 2, 3, 4, 5, 6, 7, 8, 9, 10, or more consecutive days. Administration can be daily, for example, once a day. In some embodiments, sodium chlorite is administered daily.

In some embodiments, the pharmaceutical composition can be administered in a cycle. A non-limiting example of a cycle provides: a) a first period of time wherein the pharmaceutical composition is administered at a first dose for a first number of times; and b) a second period of time wherein the pharmaceutical composition is administered at a second dose for a second number of times. In some embodiments, the cycle is performed about 2-4 times.

In some embodiments, the dosing schedule provides periods of administration alternating with periods of non-administration. In some embodiments, sodium chlorite is administered in a four-week cycle. In some embodiments, sodium chlorite is administered in a three-week cycle. In some embodiments, the cycle could be repeated as necessary to achieve the desired result. In some embodiments, sodium chlorite is administered in a two-week cycle. In some embodiments, a total of 2-4 cycles are performed. In some embodiments, a total of about 4 cycles, about 5 cycles, about 6 cycles, about 7 cycles, about 8 cycles, about 9 cycles, about 10 cycles, about 11 cycles, about 12 cycles, about 13 cycles, or about 14 cycles are performed. In some embodiments, a total of about 6 cycles are performed. In some embodiments, a total of about 10 cycles are performed. In some embodiments, a total of about 12 cycles are performed.

In some embodiments, the chlorite formulation described herein is administered daily for a first number of days in a row in first month and administered daily for a second number of days in subsequent months. In some embodiments, the first number of days is about 2, about 3, about 4, about 5, about 6, or about 7. In some embodiments, the first number of days is about 2. In some embodiments, the first number of days is about 2. In some embodiments, the first number of days is about 3. In some embodiments, the first number of days is about 4. In some embodiments, the first number of days is about 5. In some embodiments, the first number of days is about 6. In some embodiments, the first number of days is about 7. In some embodiments, the second number of days is about 2. In some embodiments, the second number of days is about 2. In some embodiments, the second number of days is about 3. In some embodiments, the second number of days is about 4. In some embodiments, the second number of days is about 5. In some embodiments, the second number of days is about 6. In some embodiments, the second number of days is about 7.

In some embodiments, the chlorite formulation described herein is initially administered daily for 5 days in a row in the first month, and daily for 3 days in a row in subsequent months. In some embodiments, the chlorite formulation described herein is initially administered daily for 5 days in a row in the first month, and daily for 3 days in a row in subsequent months, wherein the chlorite formulation comprises purified sodium chlorite, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between about 7.5 and about 9.5. In some embodiments, the chlorite formulation described herein is initially administered daily for 5 days in a row in the first month, and daily for 3 days in a row in subsequent months, wherein the chlorite formulation comprises purified sodium chlorite, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between about 7.5 and about 8.5. In some embodiments, the chlorite formulation described herein is initially administered daily for 5 days in a row in the first month, and daily for 3 days in a row in subsequent months, wherein the chlorite formulation comprises purified sodium chlorite, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between about 7.5 and about 8.

Any compositions and pharmaceutical formulation described herein can be used in kits. In some embodiments, the kits are intended for administration of sodium chlorite or a sodium chlorite-containing agent, or pharmaceutical formulations comprising such agents. The kits can include a unit dosage amount of the agents or formulations as described herein. In some variations, the kits comprise suitable packaging. In some embodiments, the kits comprise instructions for use of the active agent in a neurodegenerative disease as described above. In some embodiments, the kit contains instructions for using sodium chlorite formulations to treat a neurodegenerative disease as described herein. In some embodiments, a kit contain suitable instructions for practicing any of the treatment methods described herein with a formulation described herein. In some embodiments, a kit is used to treat any one or more of the diseases or conditions described herein. A kit can comprise an aid to administration of the active agent formulation, such as a syringe for injection or pressure pack for oral forms.

Pharmaceutical Compositions

A pharmaceutical composition of the invention can be a combination of any compounds described herein with other chemical components, such as carriers, stabilizers, solubilizers, tonicity enhancing agents, buffers, preservatives, diluents, dispersing agents, suspending agents, thickening agents, and/or excipients. The pharmaceutical compositions can include at least one pharmaceutically-acceptable carrier, stabilizer, solubilizer, tonicity enhancing agent, buffer, preservative, diluent, dispersing agent, suspending agent, thickening agent, and/or excipients and a compound described herein as free-base or pharmaceutically-acceptable salt form. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

In some embodiments, a pharmaceutical composition can be formulated for oral administration. In some embodiments, a pharmaceutical composition formulated for oral administration can be formulated by combining one or more compounds of the disclosure with one or more pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

In some embodiments, a pharmaceutical composition can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

In some embodiments, a pharmaceutical composition can be formulated for topical administration. In some embodiments, a pharmaceutical composition can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers, and preservatives. In some embodiments, a pharmaceutical composition of the disclosure can be applied topically to the skin, or a body cavity, for example, oral, vaginal, bladder, cranial, spinal, thoracic, or pelvic cavity of a subject. In some embodiments, a compound or pharmaceutical composition of the disclosure can be applied to an accessible body cavity.

In practicing the methods of treatment or use provided herein, therapeutically-effective amounts of the compounds described herein are administered in pharmaceutical compositions to a subject having a disease or condition to be treated. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions comprising a compound described herein can be manufactured, for example, by mixing, dissolving, emulsifying, encapsulating, entrapping, or compression processes. Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, elixir, nanosuspension, aqueous or oily suspensions, drops, syrups, and any combination thereof.

Non-limiting examples of pharmaceutically-acceptable excipients suitable for use include binding agents, disintegrating agents, anti-adherents, anti-static agents, surfactants, anti-oxidants, coating agents, coloring agents, plasticizers, preservatives, suspending agents, emulsifying agents, antimicrobial agents, spheronization agents, granulating agents, lubricating agents, sweetening agents, glidants, gums, flavoring agents, plant cellulosic material, and any combination thereof.

A pharmaceutical composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some embodiments, a controlled release formulation is a delayed release formulation. A delayed release formulation can be formulated to delay a compound's action for an extended period of time. A delayed release form can be formulated to delay the release of an effective dose of one or more compounds, for example, for about 4, about 8, about 12, about 16, or about 24 hours.

In some embodiments, a controlled release formulation can be a sustained release formulation. A sustained release formulation can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

A pharmaceutical composition can have a pH adjusted to from about 7 and to about 11.5. In some embodiments, the pH of a pharmaceutical composition of the disclosure can be adjusted using an agent that does not expose the formulation to high local acidity. In some embodiments, the pH of a pharmaceutical composition of the disclosure can be adjusted using, for example, monosodium phosphate, disodium phosphate, dibasic sodium phosphate, or acetic acid.

In some embodiments, a pharmaceutical composition of the disclosure can have a pH of from about 7 to about 7.5, from about 7.5 to about 8, from about 8 to about 8.5, from about 8.5 to about 9, from about 9 to about 9.5, from about 9.5 to about 10, from about 10 to about 10.5, from about 10.5 to about 11, from about 11 to about 11.5, or from about 11.5 to about 12. In some embodiments, a pharmaceutical composition of the disclosure can have a pH of from about 7 to about 7.5. In some embodiments, a pharmaceutical composition of the disclosure can have a pH of from about 7.5 to about 8. In some embodiments, a pharmaceutical composition of the disclosure can have a pH of from about 8 to about 8.5. In some embodiments, a pharmaceutical composition of the disclosure can have a pH of from about 7.5 to about 9.5.

In some embodiments, a pharmaceutical composition of the disclosure can have a pH of less than about 12. In some embodiments, a pharmaceutical composition of the disclosure can have a pH of less than about 11.5, less than about 11, less than about 10.5, less than about 10, less than about 9.5, less than about 9, less than about 8.5, less than about 8, less than about 7.5, less than about 7, less than about 6.5, or less than about 6. In some embodiments, the pH of a pharmaceutical composition of the disclosure can have a pH of less than about 11.5. In some embodiments, a pharmaceutical composition of the disclosure can have a pH of less than about 10.5. In some embodiments, a pharmaceutical composition of the disclosure can have a pH of less than about 8.5. In some embodiments, a pharmaceutical composition of the disclosure can have a pH of less than about 7.5. In some embodiments, a pharmaceutical composition of the disclosure has a pH of about 7.4. In some embodiments, a pharmaceutical composition of the disclosure has a pH that is at a physiological level.

In some embodiments, a pharmaceutical composition of the disclosure can comprise a solvent. In some embodiments, a pharmaceutical composition of the disclosure can comprise water as a solvent. In some embodiments, a pharmaceutical composition of the disclosure is at least about 50%, at least about 55%, at least about 60%, at least about 65%, at least about 70%, at least about 75%, at least about 80%, at least about 85%, at least about 90%, or at least about 95% (v/v) water. In some embodiments, a pharmaceutical composition of the disclosure is at least about 80% (v/v) water. In some embodiments, a pharmaceutical composition of the disclosure is at least about a 90% (v/v) water. In some embodiments, a pharmaceutical composition of the disclosure is at least about a 95% (v/v) water. In some embodiments, a pharmaceutical composition of the disclosure is at least about a 98% (v/v) water.

In some embodiments, a pharmaceutical composition of the disclosure is from about 50% to about 60%, from about 60% to about 70%, from about 70% to about 80%, from about 80% to about 90%, or from about 90% to about 98% (v/v) water. In some embodiments, a pharmaceutical composition of the disclosure is from about 80% to about 90% (v/v) water. In some embodiments, a pharmaceutical composition of the disclosure is from about 90% to about 95% (v/v) water. In some embodiments, a pharmaceutical composition of the disclosure is from about 90% to about 98% (v/v) water.

In some embodiments, a pharmaceutical composition comprises from about 1 μM to about 1.5 M of a compound of the disclosure. In some embodiments, a pharmaceutical composition comprises from about 1 μM to about 10 μM, from about 10 μM to about 50 μM, from about 50 μM to about 100 μM, from about 0.1 mM to about 0.5 mM, from about 0.5 mM to about 1 mM, from about 1 mM to about 25 mM, from about 25 mM to about 100 mM, from about 100 mM to about 250 mM, from about 250 mM to about 500 mM, from about 500 mM to about 750 mM, or from about 750 mM to about 1000 mM of a compound of the disclosure. In some embodiments, a pharmaceutical composition comprises from about 1 μM to about 10 μM of a compound of the disclosure. In some embodiments, a pharmaceutical composition comprises from about 10 μM to about 50 μM of a compound of the disclosure. In some embodiments, a pharmaceutical composition comprises from about 50 μM to about 100 μM of a compound of the disclosure. In some embodiments, a pharmaceutical composition comprises from about 100 μM to about 250 μM of a compound of the disclosure. In some embodiments, a pharmaceutical composition comprises from about 250 μM to about 500 μM of a compound of the disclosure. In some embodiments, a pharmaceutical composition comprises from about 1 mM to about 5 mM of a compound of the disclosure.

In some embodiments, a pharmaceutical composition comprises at least about 1 μM of a compound of the disclosure. In some embodiments, a pharmaceutical composition comprises at least about 1 μM, at least about 10 μM, at least about 50 μM, at least about 100 μM, at least about 250 μM, at least about 500 μM, at least about 750 μM, at least about 1 mM, at least about mM, at least about 50 mM, at least about 75 mM, at least about 100 mM, at least about 250 mM, at least about 500 mM, at least about 750 mM, or at least about 1000 mM of a compound of the disclosure. In some embodiments, a pharmaceutical composition comprises at least about 1 μM of a compound of the disclosure. In some embodiments, a pharmaceutical composition comprises at least about 10 μM of a compound of the disclosure. In some embodiments, a pharmaceutical composition comprises at least about 25 μM of a compound of the disclosure. In some embodiments, a pharmaceutical composition comprises at least about 50 μM of a compound of the disclosure. In some embodiments, a pharmaceutical composition comprises at least about 60 μM of a compound of the disclosure. In some embodiments, a pharmaceutical composition comprises at least about 65 μM of a compound of the disclosure. In some embodiments, a pharmaceutical composition comprises at least about 100 μM of a compound of the disclosure. In some embodiments, a pharmaceutical composition comprises at least about 250 μM of a compound of the disclosure. In some embodiments, a pharmaceutical composition comprises at least about 500 μM of a compound of the disclosure.

In some embodiments, a pharmaceutical composition comprises about 1 μM of a compound of the disclosure. In some embodiments, a pharmaceutical composition comprises about 1 μM, about 10 μM, about 50 μM, about 100 μM, about 250 μM, about 500 μM, about 750 μM, about 1 mM, about 25 mM, about 50 mM, about 75 mM, about 100 mM, about 250 mM, about 500 mM, about 750 mM, or about 1000 mM of a compound of the disclosure. In some embodiments, a pharmaceutical composition comprises about 1 μM of a compound of the disclosure. In some embodiments, a pharmaceutical composition comprises about 10 μM of a compound of the disclosure. In some embodiments, a pharmaceutical composition comprises about 25 µM of a compound of the disclosure. In some embodiments, a pharmaceutical composition comprises about 50 µM of a compound of the disclosure. In some embodiments, a pharmaceutical composition comprises about 100 µM of a compound of the disclosure. In some embodiments, a pharmaceutical composition comprises about 250 µM of a compound of the disclosure. In some embodiments, a pharmaceutical composition comprises about 500 µM of a compound of the disclosure.

In some embodiments, a pharmaceutical composition of the disclosure comprises at least about 0.5 mg/mL of a compound of the disclosure. In some embodiments, a pharmaceutical composition of the disclosure comprises at least about 0.5 mg/mL, at least about 1 mg/mL, at least about 1.5 mg/mL, at least about 2 mg/mL, at least about 2.5 mg/mL, at least about 3 mg/mL, at least about 3.5 mg/mL, at least about 4 mg/mL, at least about 4.5 mg/mL, at least about 5 mg/mL, at least about 5.5 mg/mL, at least about 6 mg/mL, at least about 6.5 mg/mL, at least about 7 mg/mL, at least about 7.5 mg/mL, at least about 8 mg/mL, at least about 8.5 mg/mL, at least about 9 mg/mL, at least about 9.5 mg/mL, or at least about 10 mg/mL of a compound of the disclosure. In some embodiments, a pharmaceutical composition of the disclosure comprises at least about 2 mg/mL of a compound of the disclosure. In some embodiments, a pharmaceutical composition of the disclosure comprises at least about 4 mg/mL of a compound of the disclosure. In some embodiments, a pharmaceutical composition of the disclosure comprises at least about 5 mg/mL of a compound of the disclosure. In some embodiments, a pharmaceutical composition of the disclosure comprises at least about 5.6 mg/mL of a compound of the disclosure. In some embodiments, a pharmaceutical composition of the disclosure comprises at least about 5.5 mg/mL of sodium chlorite. In some embodiments, a pharmaceutical composition of the disclosure comprises at least about 4 mg/mL of chlorite.

In some embodiments, a pharmaceutical composition of the disclosure comprises from about 0.5 mg/mL to about 10 mg/mL of a compound of the disclosure. In some embodiments, a pharmaceutical composition of the disclosure comprises from about 0.5 mg/mL to about 1 mg/mL, from about 1 mg/mL to about 2 mg/mL, from about 2 mg/mL to about 3 mg/mL, from about 3 mg/mL to about 4 mg/mL, from about 4 mg/mL to about 5 mg/mL, from about 5 mg/mL to about 6 mg/mL, from about 6 mg/mL to about 7 mg/mL, from about 7 mg/mL to about 8 mg/mL, from about 8 mg/mL to about 9 mg/mL, or from about 9 mg/mL to about 10 mg/mL of a compound of the disclosure. In some embodiments, a pharmaceutical composition of the disclosure comprises from about 4 mg/mL to about 5 mg/mL of a compound of the disclosure. In some embodiments, a pharmaceutical composition of the disclosure comprises from about 5 mg/mL to about 6 mg/mL of a compound of the disclosure. In some embodiments, a pharmaceutical composition of the disclosure comprises from about 4 mg/mL to about 5 mg/mL of chlorite. In some embodiments, a pharmaceutical composition of the disclosure comprises from about 5 mg/mL to about 6 mg/mL of sodium chlorite.

In some embodiments, a pharmaceutical composition of the disclosure comprises about mg/mL of a compound of the disclosure. In some embodiments, a pharmaceutical composition of the disclosure comprises about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about mg/mL of a compound of the disclosure. In some embodiments, a pharmaceutical composition of the disclosure comprises about 2 mg/mL of a compound of the disclosure. In some embodiments, a pharmaceutical composition of the disclosure comprises about 4 mg/mL of a compound of the disclosure. In some embodiments, a pharmaceutical composition of the disclosure comprises about 5 mg/mL of a compound of the disclosure. In some embodiments, a pharmaceutical composition of the disclosure comprises about 5.6 mg/mL of a compound of the disclosure. In some embodiments, a pharmaceutical composition of the disclosure comprises about 5.5 mg/mL of sodium chlorite. In some embodiments, a pharmaceutical composition of the disclosure comprises about 4 mg/mL of chlorite.

In some embodiments, a pharmaceutical composition of the disclosure is formulated for intravenous administration. In some embodiments, a pharmaceutical composition of the disclosure comprises dibasic sodium phosphate. In some embodiments, a pharmaceutical composition of the disclosure has a pH of from about 7.5 to about 9.5. In some embodiments, the pharmaceutical composition of the disclosure does not comprise any preservatives. In some embodiments, the pharmaceutical composition of the disclosure comprises about 4 mg/mL of chlorite. In some embodiments, the pharmaceutical composition of the disclosure comprises about 5.5 mg/mL of sodium chlorite.

EXAMPLES

The following examples are provided for illustrative purposes only and not to limit the scope of the claims provided herein.

Abbreviations

A2M: alpha-2-macroglobulin;
ALSFRS-R: Amytrophic Lateral Sclerosis Functional Rating Scale score
CNS: central nervous system;
CRP: C-reactive protein;
DP: disease progression;
LPS: lipopolysaccharide;
EGF: epidermal growth factor;
IL-10: interleukin 10;
IL-18, interleukin 18;
HGF: hepatocyte growth factor;
HLA-DR: human leukocyte antigen—DR isotope;
LBP: LPS-binding protein;
MT: microbial translocation;
NFkB; nuclear factor kappa B;
SAA: serum amyloid A;
SOD1: superoxide dismutase 1
sCD163: soluble CD163;
TauCl: taurine chloramine;
TDP43: transactive response DNA-binding protein 43;
TGFB1: transforming growth factor beta 1;
VC: vital capacity.

Example 1: Microbial Translocation in ALS

Study Objectives

The goal of the present study was to test whether ALS patients in a phase 2 study of sodium chlorite, a regulator of innate immune function, would show changes in microbial translocation (MT) associated plasma biomarkers over a six-month placebo-controlled trial.

MT is a dynamic process leading to a chronic inflammatory state implicated in most neurodegenerative diseases. A recent post hoc evaluation of phase 2 studies showed that compared to placebo, sodium chlorite treatment of ALS patients with plasma CRP levels greater than 1.13 mg/L slowed disease progression. Rates of ALSFRS-R and vital capacity decline were slowed as compared to placebo.

Methods

Plasma specimens taken at baseline and at 6 months from a sodium chlorite phase 2A study were evaluated by ELISA for biomarker levels related to MT. Results of MT marker quantitation were compared between treated and placebo.

Results

From the sodium chlorite 2A study, 14 sodium chlorite and 16 placebos with CRP>1.13 mg/L completed the trial. Declines over 6 months in ALSFRS-R (p=0.02) and VC (p=0.03) were significantly slowed by sodium chlorite vs. placebo. Baseline markers of MT including liposaccharide (LPS), LPS binding protein (LBP), monocyte trafficking molecule soluble CD163, and inflammasome associated interleukin 18 (IL-18) were all decreased relative to placebo values. The level of wound healing epidermal growth factor (EGF) increased in patients treated with sodium chlorite.

MT is a biological process wherein persistent macrophage activation leads to both progressive ND activity and continued gut epithelial cell dysfunction. Factors produced by LPS activated macrophages continuously drive this process. Sodium chlorite is a regulator of macrophage activation and in the current study the coupling of anti-MT activity with induction of EGF is associated with slowing ALS disease progression.

Figure 3:
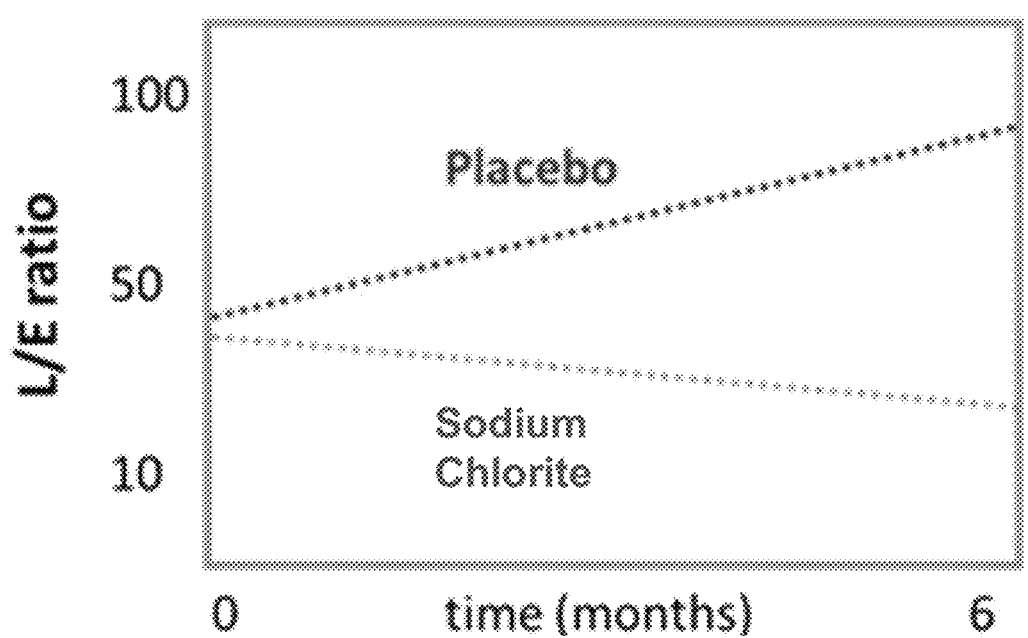
FIG. 3 shows the ratio of LPS:EGF in study patients.

FIG. 3 displays the ratio of LPS to EGF in study patients. The trend shows that the ratio decreased over time in patients treated with sodium chlorite. In contrast, the ratio increased over time in patients who received placebo.

FIG. 4 shows the innate immune cycle activation cycle. The innate inflammatory response is associated with oxidative burst and the production of HClO. HClO is converted to taurine chloramine, which regulates NFkB and inflammation.

Figure 5:
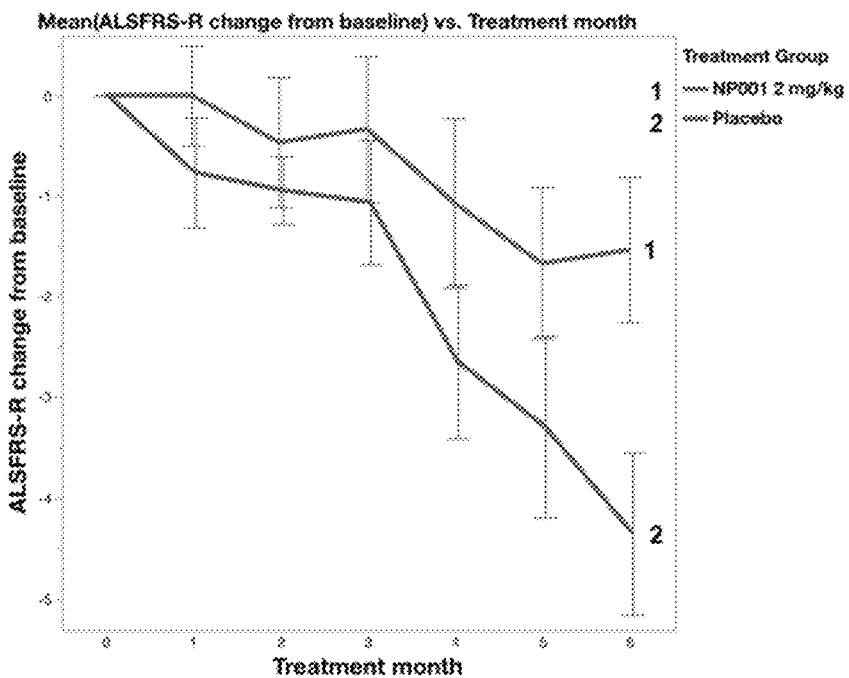
FIG. 5 shows the mean ALSFRS-R change from baseline and mean % vital capacity change from baseline in NP001-treated and placebo groups for subjects ages 40-65 with CRP>1.13 mg/L over six months. Data is represented as mean±standard error of mean.
Figure 5:
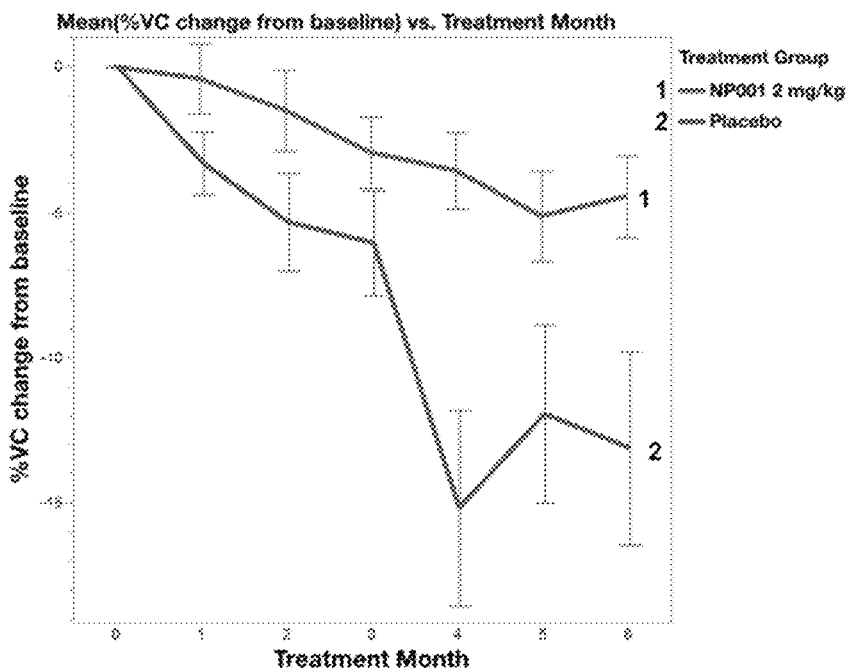

FIG. 5 shows the ALSFRS-R change from baseline and the % VC change from baseline over time for NP001 and placebo subject groups.

Figure 6:
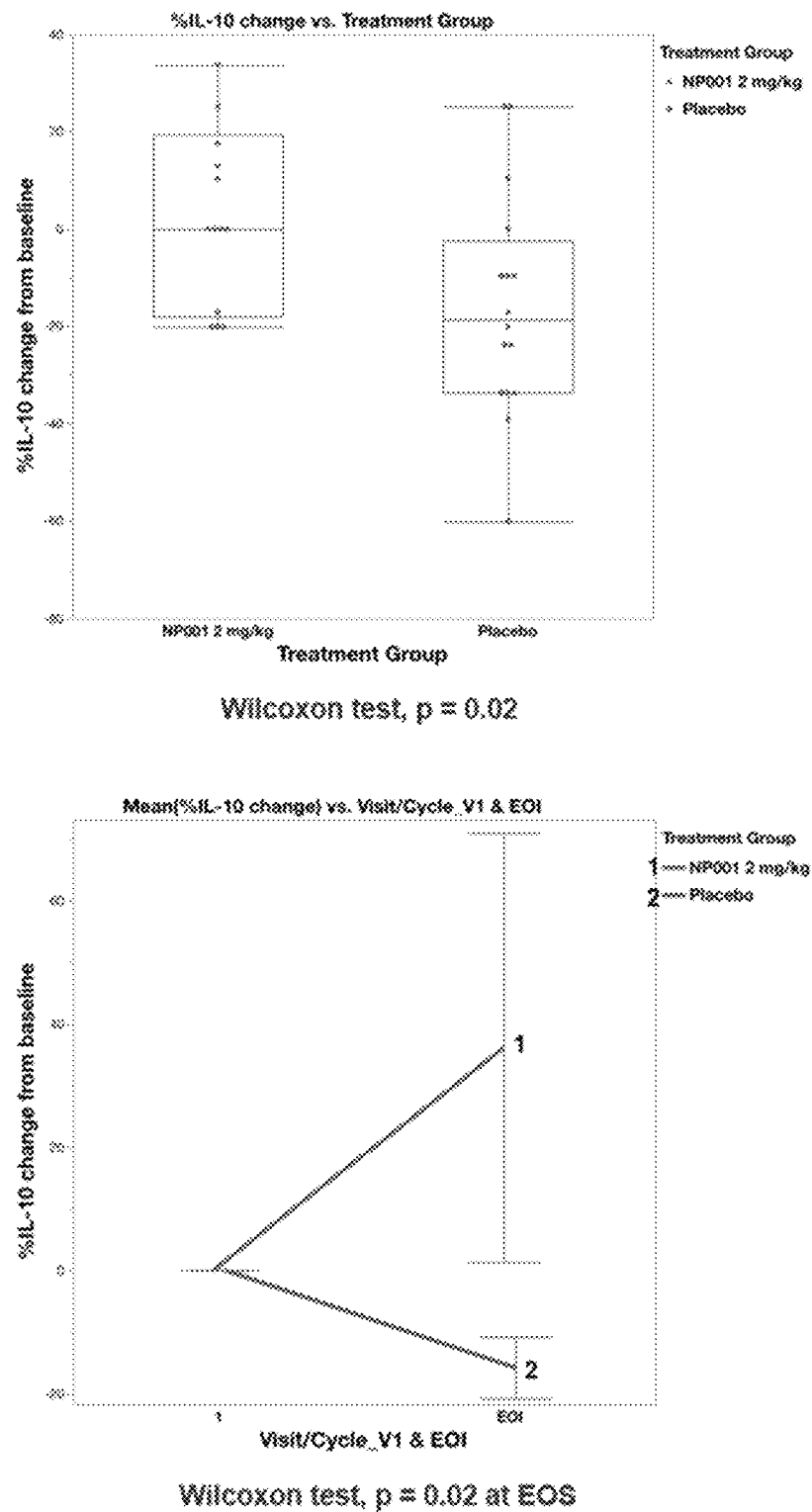
FIG. 6 shows the NP001-associated increase in biomarker IL-10 after 6 months for subjects with CRP>1.13 mg/L.
Figure 8:
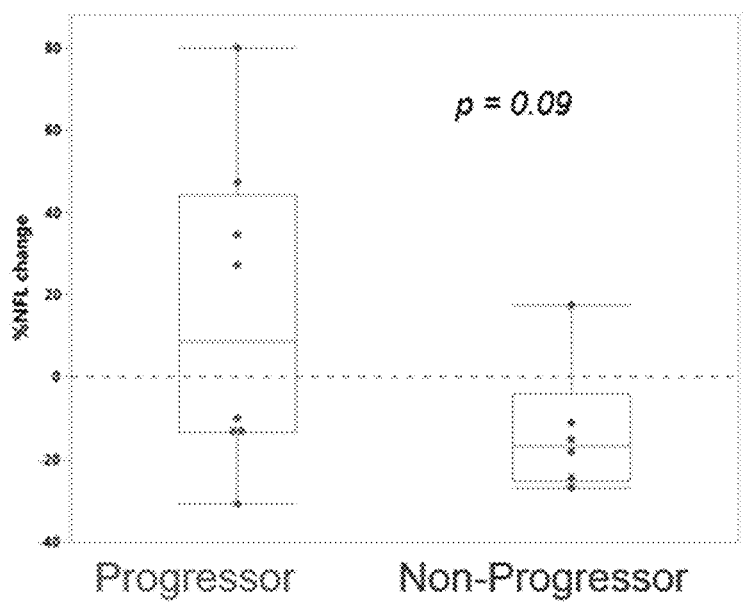
FIG. 8 shows the % change in plasma neurofilament light chain levels over 6 months in NP001-treated subjects (progressor and non-progressor) and placebo subjects.
Figure 8:
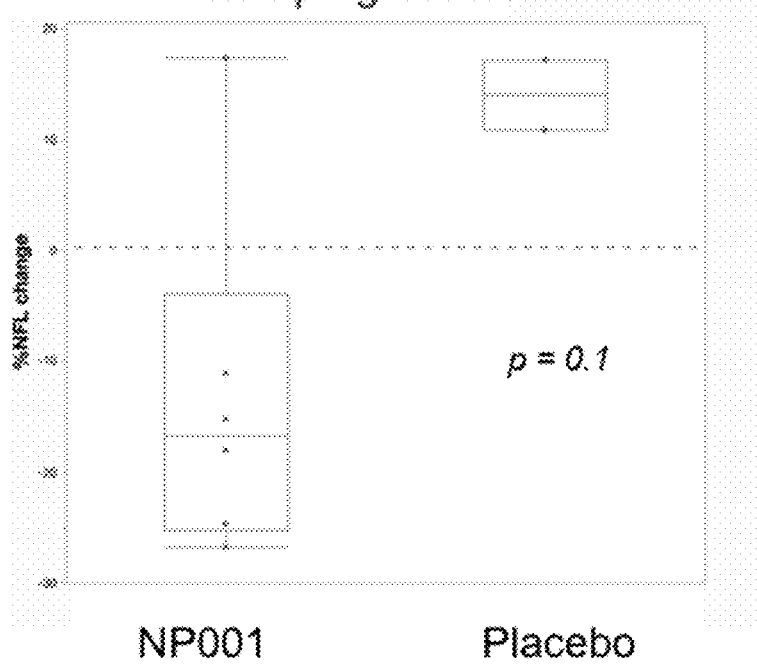

FIG. 6 shows the increase change in IL-10 from NP001. FIG. 8 shows the change in plasma neurofilament light chain levels in NP001 treated progressors, NP001 treated non-progressors, and the placebo treatment group.

Figure 7:
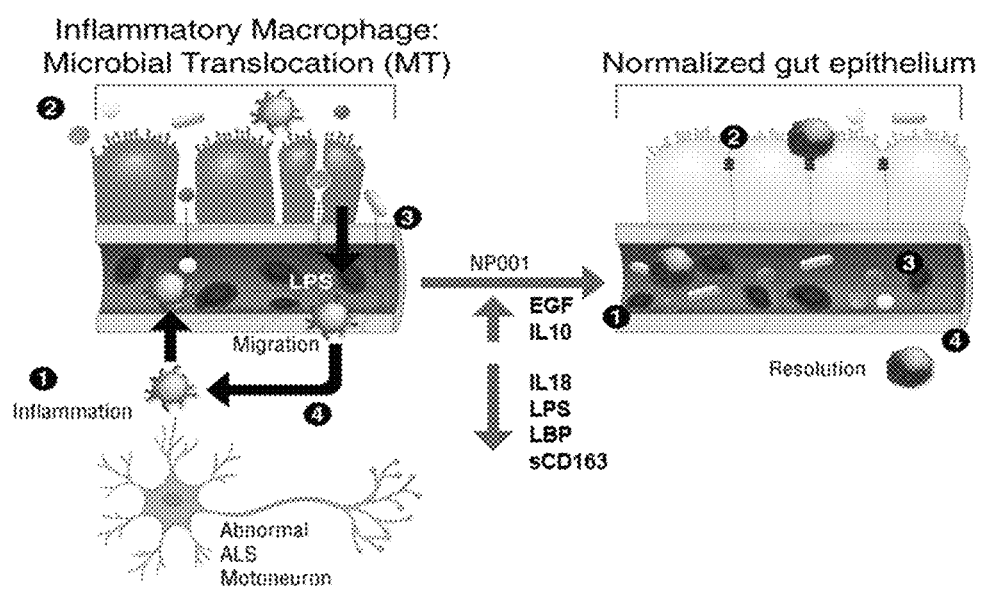
FIG. 7 shows a mechanism for microbial translocation in ALS patients and the change in levels of EGF, IL10, IL18, LPS, LBP, and sCD163 associated with the microbial translocation process in NP001 treatment.
Figure 9:
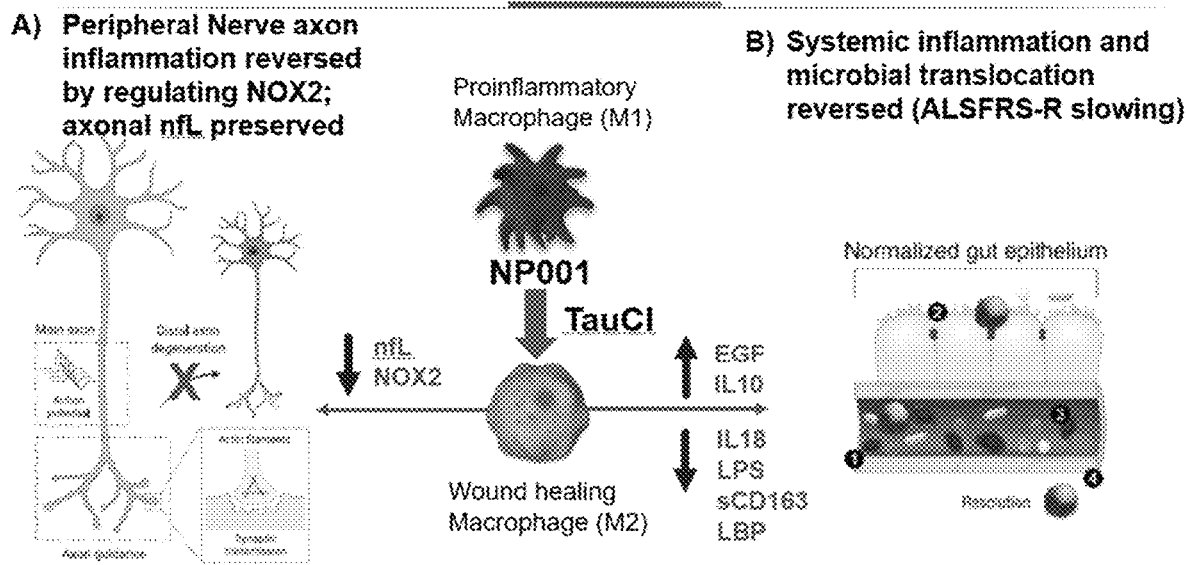
FIG. 9 shows the effect of NP001 on macrophage activation in early and advanced systemic stages of ALS.
Figure 10:
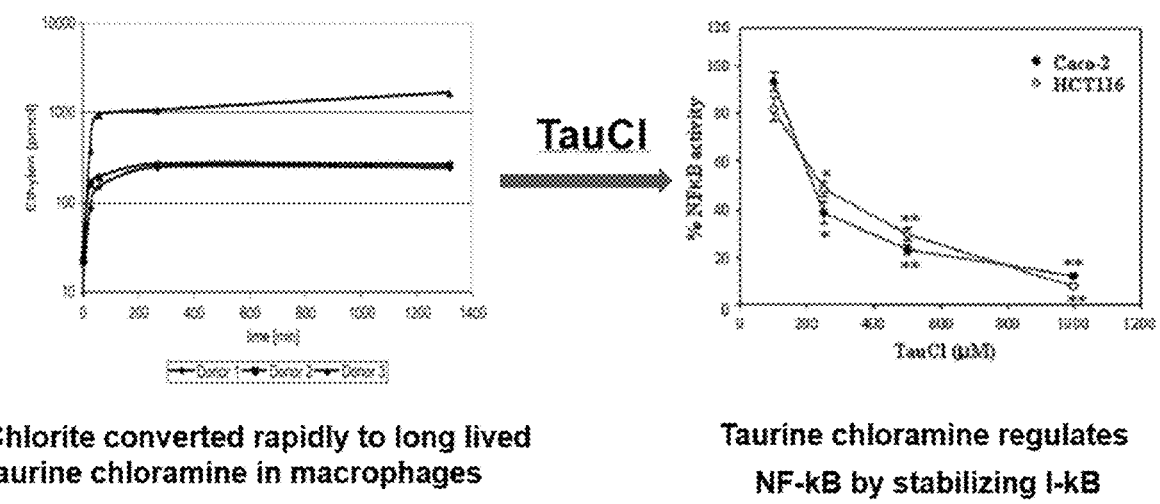
FIG. 10 shows the effect of taurine chloramine (TauCl) on regulation of NFkB.

FIG. 7 shows a mechanism for microbial translocation in ALS patients and the change in levels of EGF, IL10, IL18, LPS, LBP, and sCD163 associated with the microbial translocation process in NP001 treatment. FIG. 9 shows the effect of NP001 on macrophage activation in (a) early and (b) advanced systemic stages of ALS. FIG. 10 shows the effect of taurine chloramine (TauCl) on regulation of NFkB.

Figure 11:
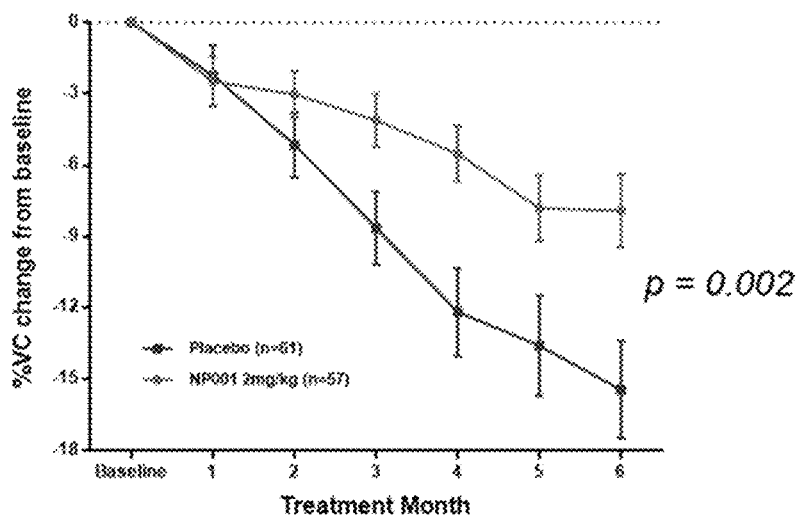
FIG. 11 shows the % change in VC from baseline in NP001-treated and placebo groups for subjects ages 40-65 with CRP>1.13 mg/L over six months and response rate of NP001-treated and placebo groups for subjects ages 40-65 with CRP>3 mg/L over six months.
Figure 11:
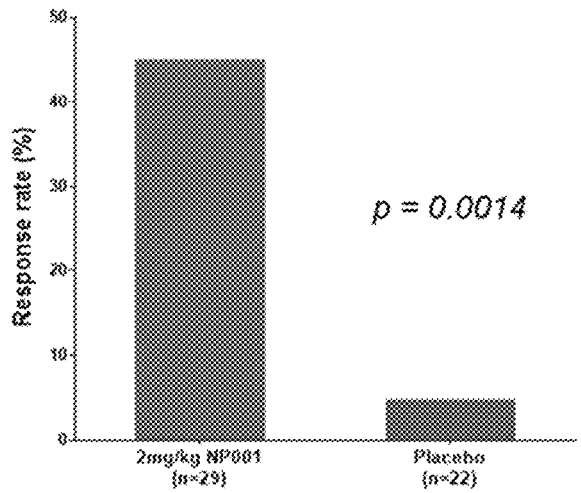

FIG. 11 shows the disease modifying activity of NP001 in early and advanced systemic stages of ALS.

Figure 12:
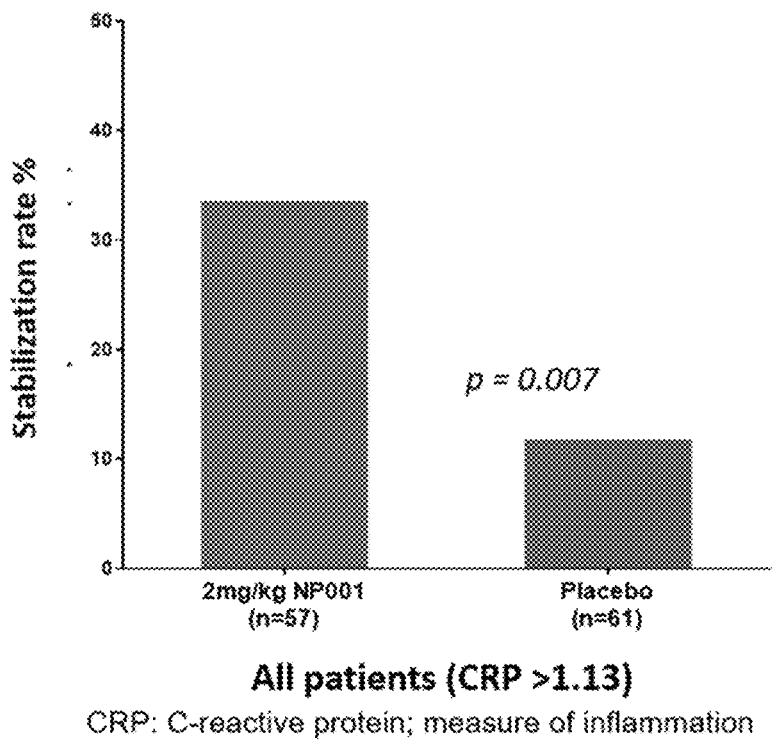
FIG. 12 shows the stabilization rate in NP001-treated and placebo groups for subjects ages 40-65 with CRP>1.13 mg/L and CRP>3 mg/L over six months.
Figure 12:
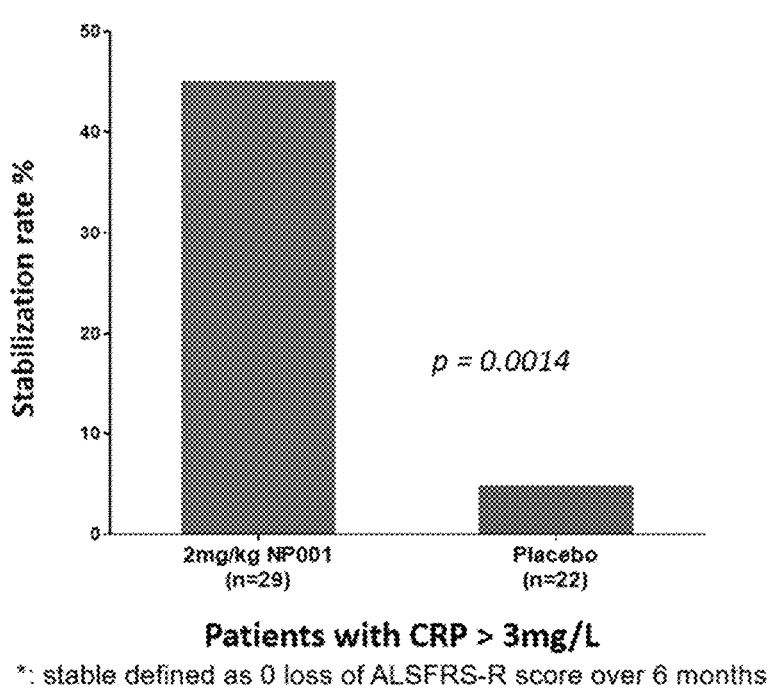

FIG. 12 shows the NP001 treatment associated ALS disease stability in relation to the level of baseline CRP.

TABLE 2 shows the analysis of biomarkers as % median change from baseline over six months for placebo and NP001-treated subject groups having CRP>1.13 mg/L aged 40-65.

TABLE 2

| Biomarker | % difference between NP001-treated and placebo at 6 months | Wilcoxon p value |
|---|---|---|
| IL-18 | −58.3 | 0.02 |
| sCD163 | −19.6 | 0.02 |
| LPS | −51.8 | 0.04 |
| LBP | −25.9 | 0.006 |
| HGF | −31.4 | 0.02 |
| EGF | 32.4 | 0.04 |
| Neopterin | 18.1 | 0.04 |
| IL-10 | 18.6 | 0.02 |

TABLE 3 shows the % change in plasma biomarkers in ALS patients with average CRP>1.13 mg/L 20 months after symptom onset.

TABLE 3

| | ALS CRP > 1.13, age 40-65 (N = 29) | ALS CRP < 1.13, age 40-65 (N = 23) |
|---|---|---|
| ALSFRS-R | p = 0.03 | p = 0.69 |
| Vital Capacity | p = 0.03 | p = 0.98 |
| IL-18 | p = 0.02 | p = 0.48 |
| sCD163 | p = 0.02 | p = 0.51 |
| EGF | p = 0.04 | p = 0.11 |
| LPS | p = 0.04 | p = 0.68 |
| LBP | p = 0.006 | p = 0.23 |
| Neopterin | p = 0.04 | p = 0.48 |
| HGF | p = 0.02 | |
| IL-10 | p = 0.02 | |

TABLE 4 shows the mean % predicted vital capacity change from baseline over 6 months in population with age≤65 and CRP>1.13 mg/L.

TABLE 4

| Treatment month of % VC change from baseline | NP001 2 mg/kg | Placebo | Wilcoxon p Value |
|---|---|---|---|
| Baseline VC | N: 74<br>Mean: 93.8<br>Std. Dev.: 19.6<br>Median: 90.5<br>Min: 56.0<br>Max: 136.7 | N: 73<br>Mean: 89.6<br>Std. Dev.: 18.3<br>Median: 87.0<br>Min: 51.0<br>Max: 135.0 | 0.27 |
| Month 1 | N: 74<br>Mean: −2.5<br>Std. Dev.: 8.2<br>Median: −0.9<br>Min: −29.1<br>Max: 10.7 | N: 73<br>Mean: −2.5<br>Std. Dev.: 9.4<br>Median: −2.2<br>Min: −35.9<br>Max: 18.3 | 0.76 |
| Month 2 | N: 72<br>Mean: −4.6<br>Std. Dev.: 10.0<br>Median: −2.6<br>Min: −51.2<br>Max: 17.3 | N: 72<br>Mean: −5.6<br>Std. Dev.: 11.1<br>Median: −3.3<br>Min: −53.8<br>Max: 21.8 | 0.61 |
| Month 3 | N: 69<br>Mean: −6.5<br>Std. Dev.: 12.4<br>Median: −3.8<br>Min: −53.7<br>Max: 13.6 | N: 70<br>Mean: −9.5<br>Std. Dev.: 13.1<br>Median: −6.0<br>Min: −46.4<br>Max: 22.5 | 0.10 |
| Month 4 | N: 68<br>Mean: −8.1<br>Std. Dev.: 13.0<br>Median: −5.4<br>Min: −60.7<br>Max: 12.3 | N: 70<br>Mean: −12.8<br>Std. Dev.: 15.4<br>Median: −9.7<br>Min: −59.5<br>Max: 14.1 | 0.02 |

TABLE 4-continued

| Treatment month of % VC change from baseline | NP001 2 mg/kg | Placebo | Wilcoxon p Value |
|---|---|---|---|
| Month 5 | N: 64<br>Mean: −9.4<br>Std. Dev.: 13.6<br>Median: −6.4<br>Min: −65.6<br>Max: 8.1 | N: 65<br>Mean: −13.1<br>Std. Dev.: 15.5<br>Median: −11.1<br>Min: −58.1<br>Max: 26.9 | 0.04 |
| Month 6 | N: 59<br>Mean: −9.1<br>Std. Dev.: 14.1<br>Median: −5.4<br>Min: −72.1<br>Max: 5.3 | N: 64<br>Mean: −14.7<br>Std. Dev.: 15.0<br>Median: −10.9<br>Min: −62.9<br>Max: 12.6 | 0.005 |

Example 2: Regulation of Macrophage Activation in ALS

Study Objectives

Amyotrophic lateral sclerosis (ALS) is a fatal disease with motor neuron degeneration leading to paralysis and death within as little as 2-5 years after disease onset. Approximately 10-15% of ALS patients have a familial form of disease associated with genetic abnormalities whereas the majority of individuals have a sporadic form of disease.

A possible approach to therapy is to focus on subsets of patients most responsive to a therapy. Non-limiting examples of therapeutic targets include ALS associated genetic mutations, reactive oxygen species, misfolded proteins, dysfunctional mitochondria, blood derived macrophage function, growth factor deficiencies, and neuroinflammation.

An intravenous formulation of sodium chlorite has been under development for ALS. An example of a mechanism of action is the regulation of macrophage activation though modulation of the respiratory burst function. Sodium chlorite is a regulator of innate immune function. In a phase 1 dose ascending study in ALS patients, sodium chlorite administration was associated with a dose dependent down regulation of monocyte activation markers CD16 and HLA-DR. Normally, phagocytes undergo an oxidative burst, producing hypochlorous acid (HOCl) when activated by infectious agents. This toxic byproduct is rapidly converted to taurine chloramine (TauCl) which delivers an anti-inflammatory signal to macrophages, turning off NFkB and upregulating phagocytic/wound healing function. Sodium chlorite, as a prodrug, is converted to TauCl when in contact with heme-associated iron causing macrophages to become anti-inflammatory, phagocytic and wound healing.

A post hoc analysis of data from a combined, six-month phase 2A and phase 2B trial of sodium chlorite in ALS patients defined a large subset of patients who responded clinically. This subset was between 40-65 years old and had baseline plasma C-reactive protein (CRP) levels>1.13 mg/L. The goal of the current study was to test plasma biomarker levels in treated as compared to control patients to determine whether the clinical response would be related to some form of macrophage-targeted immune regulation.

Methods

Description of ALS Phase 2A trial and participants: Participants received a total of infusions administered intravenously over 6 cycles during a 25-week double-blind treatment period. There were 4 weeks between the start of each cycle. Cycle 1 consisted of 5 consecutive daily infusions. Cycles 2, 3, 4, 5, and 6 each consisted of 3 consecutive daily infusions. Plasma specimens for biomarker analysis were obtained at the beginning and end of study.

Analysis of clinical outcome data: The predefined endpoints from the phase 2A study were not achieved, however participants with >the median plasma CRP (of all participants) of 1.13 mg/L when used as a cut point for outcome analysis suggested that patients with a higher level of CRP showed a trend towards slowing disease progression as measured by evaluating change from baseline level of the ALS functional rating scale-revised (ALS/FRS-R) over the six-month trial. ALS patients with less than 1.13 mg/L at baseline were also evaluated monthly for ALSFRS-R score loss. In addition to observing ALS patient slowing progression over time, a subset stopped progressing over the six months and these non-progressors were all within a 40-age range.

Source of patient specimens: The plasma specimens had been stored at −80° C. since the trial ended and were all evaluated for biomarker levels. All patients with CRP>1.13 mg/L within the 2 mg/kg and placebo arms who completed the 6-month study and had plasma available from baseline and end of study were included in the current analysis (14 NP001, 15 placebo).

Plasma factors evaluated: Phase 2A data showed that plasma IL-18 and LPS were elevated at baseline in patients treated with drug (2 mg/kg) and as compared to placebo were significantly reduced towards normal by six months. Based on these results, markers were evaluated for: 1) microbial translocation/LPS activation: (LPS binding protein), HGF (hepatocyte growth factor), LPS; 2) Classical proinflammatory factors produced by activated macrophages IL-6, IL-8, TNF-a; 3) Immunoregulatory and wound healing: IL-10, neopterin and EGF (epidermal growth factor); and 4) monocyte trafficking factor, soluble CD163.

Results

Figure 13:
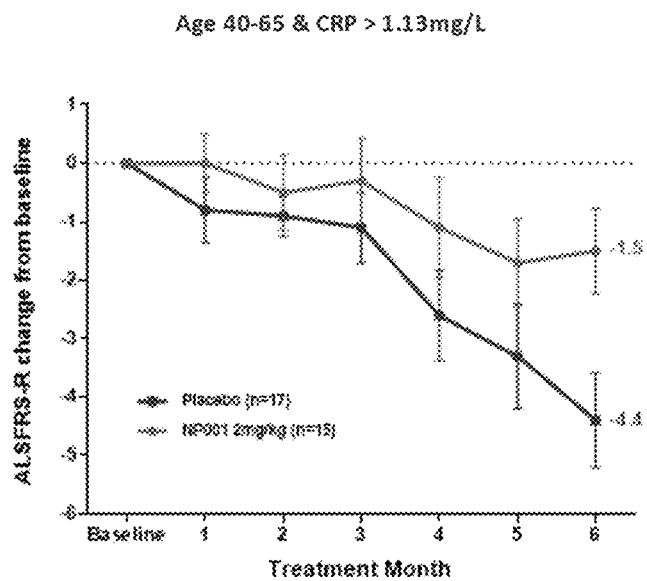
FIG. 13 shows the ALSFRS-R change from baseline in NP001-treated and placebo groups for subjects ages 40-65 with CRP>1.13 mg/L or CRP<1.13 mg/L over six months. Data are represented as mean±standard error of mean.
Figure 13:
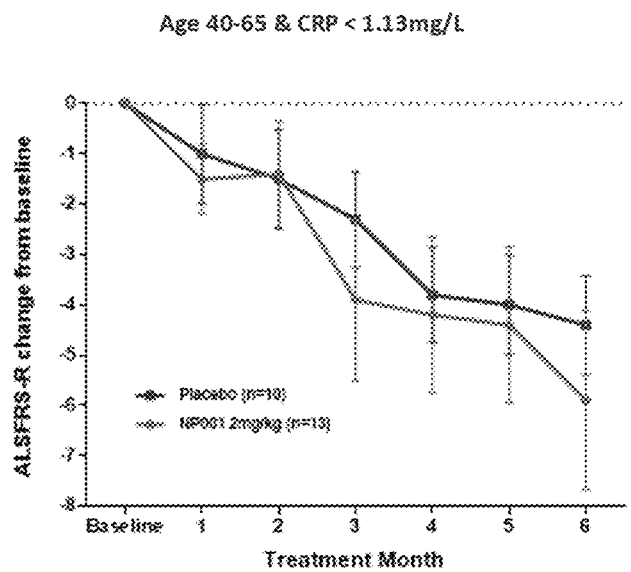
Figure 14:
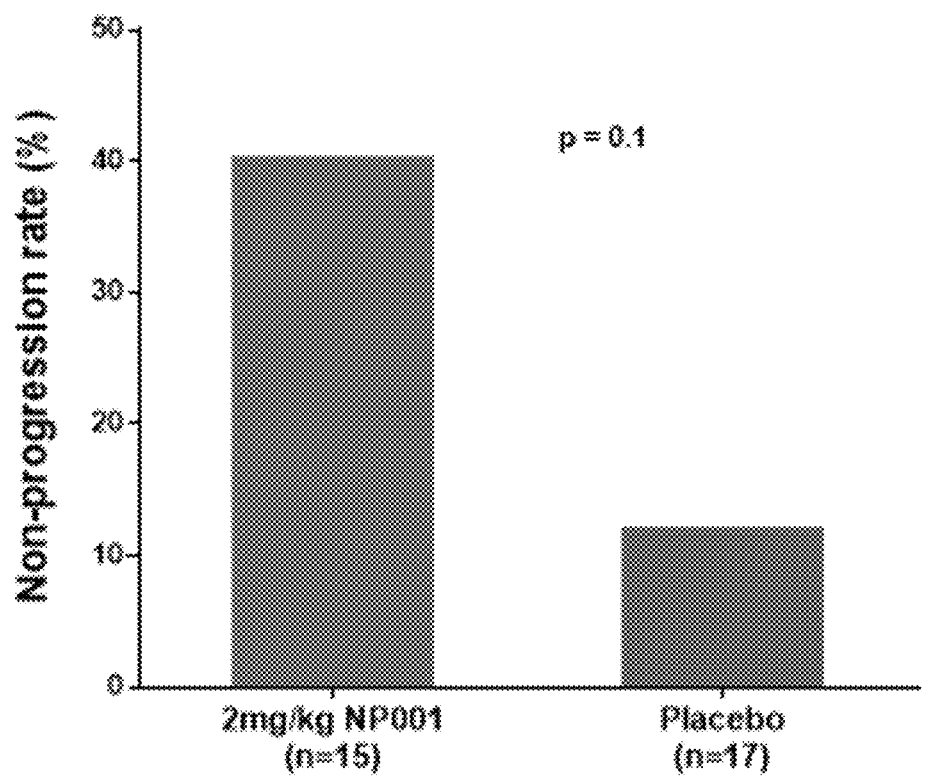
FIG. 14 shows the non-progression rate in NP001-treated and placebo groups for subjects ages 40-65 with CRP>1.13 mg/L. Non-progressors were defined as having no decrease in ALSFRS-R score at 6 months. The proportion of non-progressors (non-progression rate) in 2 mg/kg NP001 treatment (6 out of 15 subjects) was higher than in the placebo group (2 out of 17 subjects).

NP001 slows loss of ALSFRS-R: There were no significant demographic differences between the two patient groups at baseline. The number of 2 mg/kg NP001 and placebo recipients that qualified for the current biomarker analysis were 14 and 15, respectively. All were within the same CRP and age range and had baseline and end of study plasma specimens available for analysis. The mean plasma CRP value for this subgroup was 3.2 mg/L. The treated arm lost 1.2 units of ALSFRS-R score over six months whereas the placebos lost 4.6 units (p=0.03)(FIG. 13). ALS patients in the CRP<1.13 mg/L were also followed over 6 months (FIG. 13) and no significant differences were observed in clinical outcome (p=0.69). The mean CRP value for this group was 0.71 mg/L. No biomarker analyses were performed on this group. FIG. 14 shows that ALS patients treated with drug had a non-progression rate of 35% whereas the placebos were less than 10% (p=0.08).

Plasma Biomarkers from the Phase 2A

Figure 15:
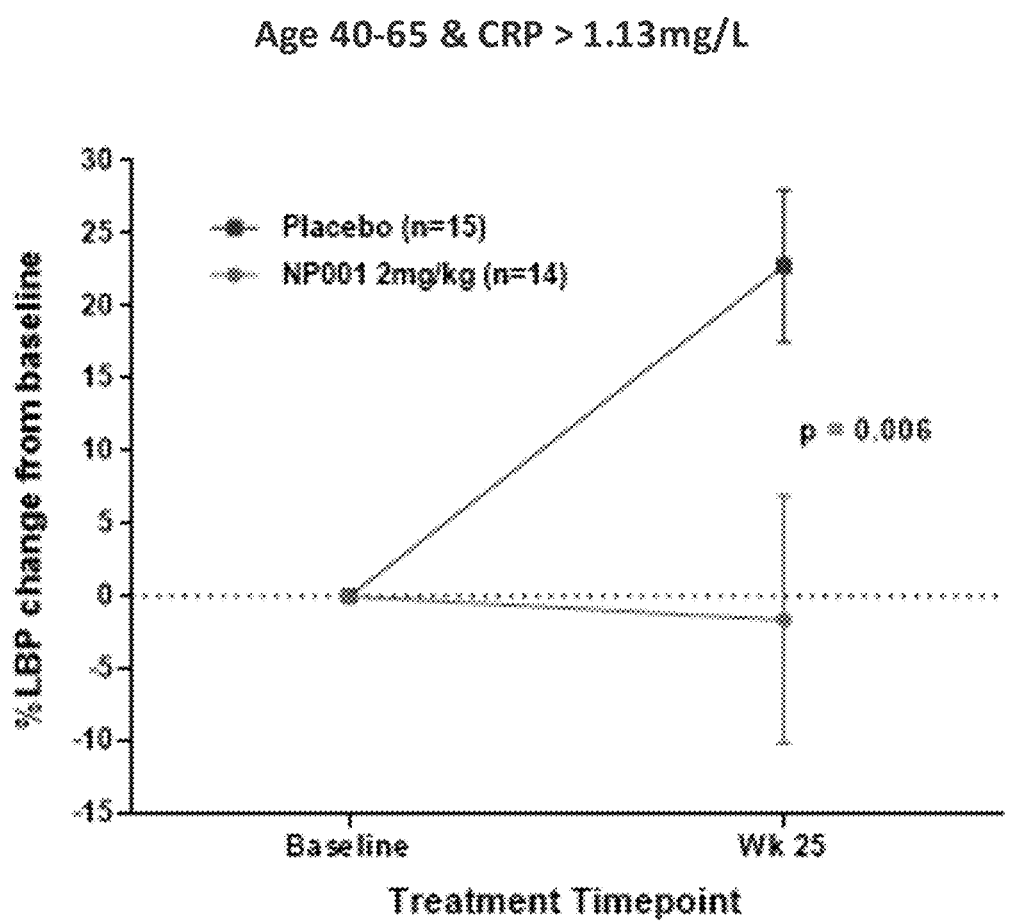
FIG. 15 shows the % LBP change from baseline in NP001-treated and placebo groups for subjects aged 40-65 with CRP>1.13 mg/L over 25 weeks. Data are represented as mean±standard error of mean.
Figure 16:
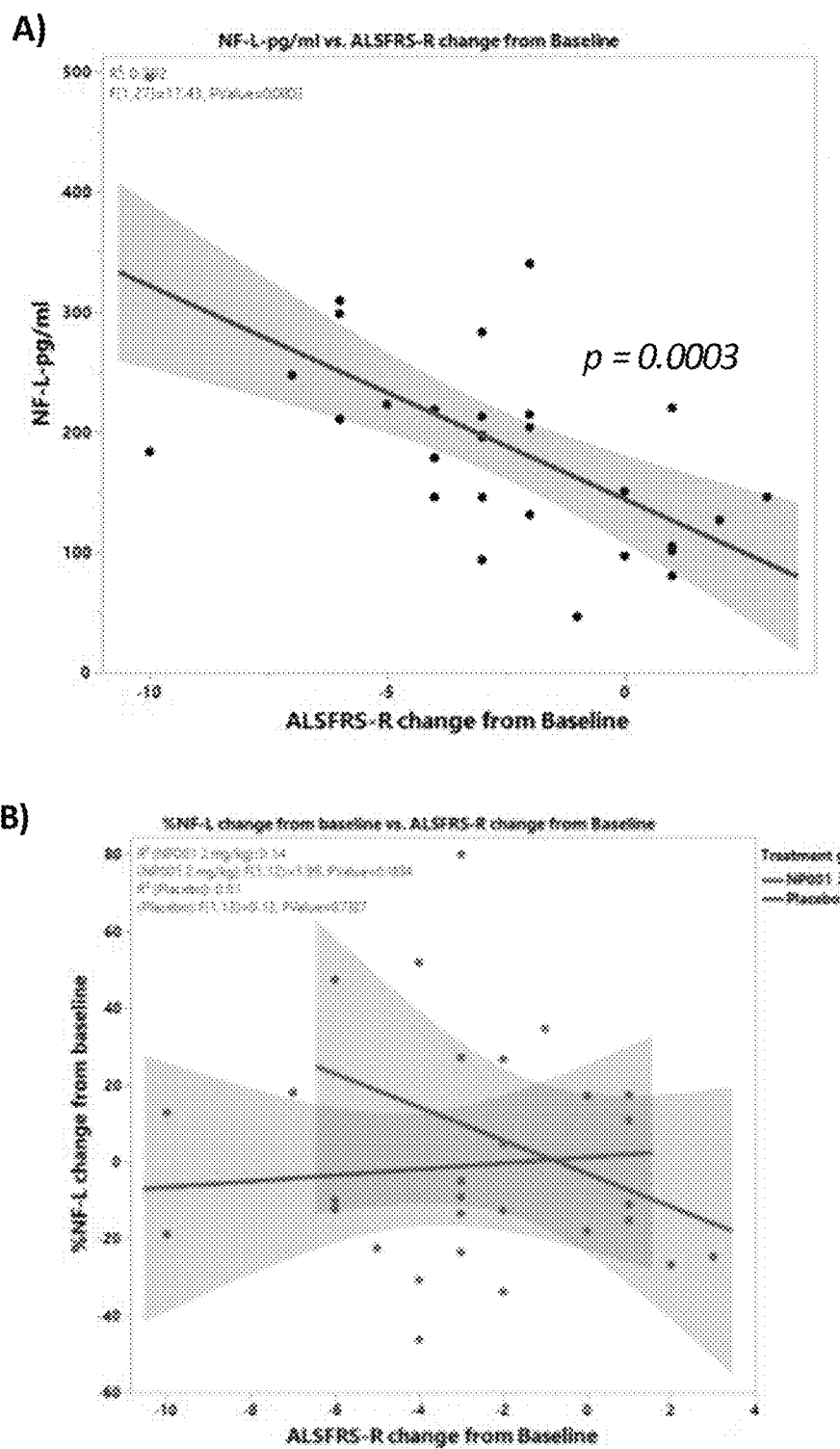
FIG. 16 shows plasma neurofilament light chain (NfL) levels vs. ALSFRS-R change from baseline compared to % NfL change from baseline vs. ALSFRS-R change from baseline in NP001-treated and placebo patients over six months.
Figure 17:
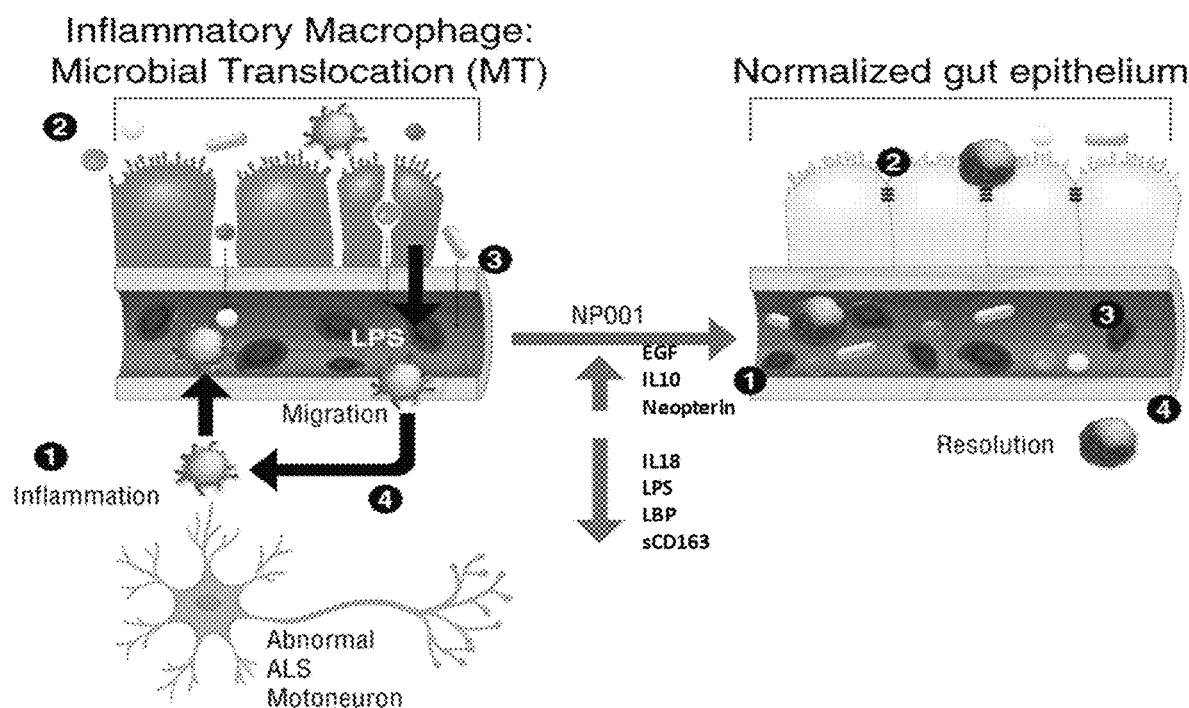
FIG. 17 shows a mechanism for microbial translocation in ALS patients and the change in EGF, IL10, Neopterin, IL18, LPS, LBP, and sCD163 associated with the microbial translocation process in NP001 treatment.

Plasma specimens were evaluated at baseline and the % change from baseline for the 10 biomarkers analyzed. TABLE 5 shows the baseline values for all biomarkers analyzed. No statistically significant differences were observed between the drug and placebo groups at baseline. An example of change from baseline values over the six-month study is shown in FIG. 15 for LBP. TABLE 6 shows the results broken into two categories based on whether the values in treated vs. placebo A) decreased or B) Increased. Values for IL-6, IL-8 and TNF-a were within the normal range and did not change over the six-month study. Factors that decreased in relationship to placebo over 6 months were those associated with microbial translocation (LPS, LBP, HGF), monocyte trafficking (sCD163) and inflammasome activation (IL-18). Values that increased were those associated with either inflammation suppression (IL-10, neopterin) or wound healing (EGF). A schematic that describes the changes in various functions that lead to microbial translocation and the resolution with the drug is shown in FIG. 17.
NfL (Neurofilament Light Chain) Levels Change Most in Non-Progressors NP001 Treated Patients The biomarkers that were measured and recorded in TABLES 5 and 6 were to test whether the drug might regulate microbial translocation. To test whether the drug would have a measurable effect on CNS markers of disease activity, plasma NfL levels were evaluated. FIG. 16 shows a direct relationship between change in NfL levels and change in ALSFRS-R scores in drug treated subjects but not in the placebo subjects. Treated patients who showed the greatest loss of NfL were the patients who stopped progressing during the course of the 6-month study. FIG. 17 shows that treated non-progressors had a trend towards a loss of plasma NfL as compared to progressors (loss of at least 1 ALSFRS-R Unit over 6 months, p=0.09). Similarly, non-progressors showed a decline in NfL levels as compared to placebo non progressors.

ALS patients show evidence for microbial translocation having detectible levels of LPS in plasma. A non-limiting example of a mechanism for this process is outlined in FIG. 17, left: 1) ALS progression advances to the point wherein abnormal neurons stimulate local microglia leading to production of proinflammatory factors that activate blood monocytes to become proinflammatory. 2) Inflammatory macrophages do not phagocytose microorganisms or participate in wound healing. The epithelial cells of the colon turn over every 5 days making the wound healing function critical to maintaining colonic epithelium integrity. Leakage of bacteria/bacterial products occurs into the blood. 3) Bacterial endotoxin (LPS) activates blood monocytes and tissue macrophages leading to a systemic proinflammatory state. 4) Monocytes are recruited from the blood into damaged tissues to initiate repair. However, LPS activation leads to trafficking of non-wound healing, non-phagocytic proinflammatory cells into the damaged tissues leading to persistence of disease.

Treatment led to resolution of biomarker levels associated with microbial translocation process. A non-limiting example of a mechanism for this process is outlined in FIG. 17, right: 1) Drug induced TauCL down regulates NFkB and proinflammatory factors. 2) Increased EGF augments gut epithelium repair. Bacterial translocation resolves. 3) Macrophages converted to phagocytic and wound healing. 4) Drop in sCD163 signifies that blood monocyte traffic to CNS is decreased Discussion The phase 2A study evaluated drug activity in all ALS patients with symptom onset with the past three years. This study did not show significant clinical activity. However, patients who had plasma CRP levels above the median value (1.13 mg/L) for the entire study showed a dose responsive relationship between drug and change in ALSFRS-R score over the six months. The initial study was underpowered to confirm that this level of CRP would be required to observe disease specific activity of NP001. The goal of the study was to test whether clinical outcome would be related to biomarker changes that reflected the drug's mechanism of action. Plasma specimens evaluated were those from all participants in this trial who received 2 mg/kg drug or placebo and fell within the age range of 40-65.

Included in the phase 2A analysis were biomarker evaluation results from patients (drug treated vs. placebo) who showed no loss of ALSFRS score over the 6-month study. In the original description of the phase 2A trial, drug treatment led to normalization of plasma IL-18 and reduction in plasma LPS levels, both significant findings as compared to placebo. Based on these changes, the biomarkers evaluated in the current study were those related to macrophage activation in relationship to microbial translocation.

A significant clinical finding upon reanalysis of the phase 2A study is shown in FIG. 13. Using the age cutoff, clinical outcome was evaluated in ALS patients above and below the CRP 1.13 mg/L cutoff for change in ALSFRS-R over time. Note the highly significant difference between the >1.13 CRP NP001 vs. placebo (p=0.03) as compared to no observable difference in patients with CRP<1.13 mg/L. These two groups had median CRP values of 3.2 vs. 0.7 mg/L, respectively. In addition to evaluation of rate of ALSFRS-R score loss in the >1.13 mg/L CRP, a significant subset of patients stopped progressing as defined by no loss in ALSFRS-R score over six months. Based on these results, plasma specimens from the age restricted patients with >CRP 1.13 mg/L were evaluated to test whether clinical outcome would be related to NP001-associated biomarker changes.

Rather than test a broad spectrum of inflammatory markers, the study focused on those that might reflect a drug associated mechanism of action related to microbial translocation. One of the goals of this study was to confirm whether sodium chlorite therapy could regulate microbial translocation thereby acting as a general neuroinflammatory disease modifier.

The biomarker evaluation approach for in this study had several features. The first was to identify a cohort of patients treated with sodium chlorite that had a significant benefit in terms of slowing their disease progression. The second was the selection of biomarkers that would reflect the activity of drug induction of macrophage regulation. The schematic shown in FIG. 17 maps those responses in the context of microbial translocation regulation. The third was to identify biomarkers that could be utilized to test this clinical approach in other neuroinflammatory diseases.

The first marker that tracked with clinical outcome is CRP. CRP (C-Reactive Protein) has been thought of mostly as a nonspecific protein marker of inflammation made by the liver in response to infection or inflammatory disease. However, two pathways exist for CRP activation in response to inflammatory stimuli. Pathogen-associated molecular patterns (PAMPs) drive NFKB activation and other inflammatory pathways by surface expressed toll-like receptors (TLR) and induce the release of inflammatory cytokines (such as IL-6, IL-8, TNF-a) from macrophages. The PAMP pathway is most active in upregulating CRP release from the liver in response to bacteria or other infectious agents. In a parallel activation pathway, major tissue injury activates the sterile inflammation pathway by the release of damage (or danger) associated molecular patterns (DAMPs) to activate the inflammasome-mediated processing of IL-1ß and IL-18 after binding to endosomal receptors. This pathway induces CRP not through the liver but in part through activation of anti-inflammatory molecules from adipose tissue. Both pathways lead to the production of CRP, a pentameric protein that as a biologically active molecule down regulates proinflammatory processes while facilitating the clearance of the body of infected material and damaged tissues. The absence of proinflammatory factor elevation of IL-6, IL-8 and TNFa from this subset coupled with the regulation of elevated IL-18 suggests that the CRP observed in the blood of drug responsive patients is induced in response to tissue injury. In this respect, CRP elevation would be providing an effector molecule, the CRP pentamer, to augment the innate response to tissue injury.

The factors down regulated in drug-responsive patients generally tracked with the effects on macrophage activation induced by the drug's TauCl induction activity. TauCl exposed macrophages shut down NFkB related genes, and wound healing in the gut allows for the halting of microbial translocation and reconstruction of effective innate immunity. Once LPS is removed as a perpetual driver of MT signaling, LPS reactive factors such as hepatocyte growth factor (HGF), neopterin, LPS binding protein (LBP), IL-18 and epidermal growth factor are up and down regulated relatively quickly. This final point is important given that ALS patients whose disease stopped while on drug would have to have the disease driving factors quickly reversed in order to maintain ALSFRS-R score stability.

Many of the biomarkers regulated by the drug in the study presented here are abnormal in patients with AD, PD, and other neuroinflammatory diseases. In a cyclic activation and self-regulation cycle that occurs with innate immune function any measurable unregulated factor suggests a potential use for sodium chlorite. For example, both AD and PD patients have lower than normal EGF, a growth factor known to promote wound healing in the gut and restore function in animal models.

Another factor that best defines the phenomenon of a cyclic self-regulating pathway is related to neopterin levels. Disease activity that involves macrophage activation is associated with upregulation of neopterin. Based on the evaluation of specimens from drug responsive patients, biomarker changes reflect a constructive and diseased regulatory activity of the marker. Neopterin is induced by LPS and acts to regulate the degree of innate immune activation through induction of alternative activation type factors in macrophages such as heme-oxygenase 1 and nrf-2.

In conclusion, the current study utilized a patient population clinically responsive to sodium chlorite, a macrophage activation regulator. Biomarker analysis confirmed the drug activities at regulating MT in those patients who already had responded to a tissue damage signal by upregulating CRP. The regulation must have occurred in these patients as a significant subset halted disease progression over the 6-week study.

TABLE 5. Baseline plasma biomarker levels in NP001-treated and placebo subject groups in ALS patients age 40-65 and CRP>1.13 mg/L

TABLE 5

| Baseline plasma biomarker levels | NP001 2 mg/kg | | | | | | Placebo | | | | | | Wilcoxon p Value |
|---|---|---|---|---|---|---|---|---|---|---|---|---|---|
| | N | Mean | Std Dev | Median | Min | Max | N | Mean | Std Dev | Median | Min | Max | |
| IL-18 (pg/ml) | 14 | 68.3 | 45.4 | 52.1 | 18.4 | 159.5 | 15 | 45.7 | 25.1 | 44.9 | 16.5 | 118.2 | 0.18 |
| CD163 (ng/ml) | 14 | 288.3 | 96.9 | 267.6 | 143.8 | 473.5 | 15 | 258.8 | 98.3 | 219.6 | 163.7 | 495.3 | 0.42 |
| LPS (EU/ml) | 14 | 0.58 | 1.30 | 0.12 | 0.03 | 4.74 | 15 | 0.16 | 0.21 | 0.03 | 0.03 | 0.60 | 0.11 |
| LBP (ng/ml) | 14 | 3660.9 | 1945.6 | 3900.5 | 37.8 | 6377.6 | 15 | 3328.1 | 1535.0 | 3411.9 | 511.1 | 6062.4 | 0.71 |
| HGF (pg/ml) | 14 | 488.7 | 116.8 | 452.5 | 335.55 | 820.6 | 15 | 406.2 | 140.7 | 354.2 | 175.3 | 650.1 | 0.11 |
| EGF (pg/ml) | 14 | 89.5 | 73.6 | 49.5 | 22.3 | 250.6 | 15 | 62.9 | 24.5 | 55.3 | 26.7 | 114.6 | 0.91 |
| Neopterin (nM) | 14 | 8.6 | 1.8 | 8.0 | 5.6 | 11.2 | 15 | 7.18 | 1.7 | 7.1 | 4.1 | 11.1 | 0.06 |
| IL-10 (pg/ml) | 14 | 1.86 | 0.24 | 1.84 | 1.47 | 2.22 | 15 | 1.86 | 0.29 | 1.84 | 1.47 | 2.22 | 0.94 |

TABLE 6. Plasma biomarker change from baseline in NP001-treated and placebo subject groups in ALS patients age 40-65 and CRP>1.13 mg/L

TABLE 6

| % Biomarker change from baseline | NP001 2 mg/kg | | | | | | Placebo | | | | | | Wilcoxon p Value |
|---|---|---|---|---|---|---|---|---|---|---|---|---|---|
| | N | Mean | Std Dev | Median | Min | Max | N | Mean | Std Dev | Median | Min | Max | |
| % IL-18 change | 14 | 25.8 | 85.7 | -2.1 | -73.8 | 231.5 | 15 | 74.2 | 78.0 | 56.19 | -5.30 | 272.60 | 0.02 |
| % CD163 change | 14 | -3.5 | 17.9 | -5.9 | -31.5 | 41.4 | 15 | 37.9 | 76.7 | 13.69 | -25.80 | 288.40 | 0.02 |
| % LPS change | 14 | -22.0 | 65.2 | -30.4 | -94.7 | 140.0 | 15 | 535.7 | 1476.5 | 21.43 | -82.90 | 5780.00 | 0.04 |
| % LBP change | 14 | -1.6 | 31.9 | -5.4 | -50 | 73.4 | 15 | 22.8 | 20.2 | 20.48 | -9.00 | 75.90 | 0.006 |
| % HGF change | 14 | -7.6 | 26.5 | -14.3 | -36.9 | 58.4 | 15 | 15.6 | 28.5 | 15.02 | -27.72 | 74.46 | 0.03 |

TABLE 6-continued

| % Biomarker change from baseline | NP001 2 mg/kg | | | | | | Placebo | | | | | Wilcoxon p Value |
|---|---|---|---|---|---|---|---|---|---|---|---|---|
| | N | Mean | Std Dev | Median | Min | Max | N | Mean | Std Dev | Median | Min | Max | |
| % EGF change | 14 | 64.3 | 135.2 | 6.5 | −39.1 | 382.5 | 15 | −1.7 | 67.2 | −25.9 | −98.2 | 148.8 | 0.04 |
| % Neopterin change | 14 | 13.9 | 20.4 | 10.8 | −7.9 | 73.4 | 15 | −3.5 | 17.7 | −7.3 | −34.4 | 23.0 | 0.04 |
| % IL-10 change | 14 | 38.8 | 139.6 | 0.0 | −20.11 | 520.3 | 15 | −12.9 | 20.6 | −17.1 | −39.1 | 25.2 | 0.03 |

Example 3: Regulation of the Innate Immune System in ALS

Study Objectives

The goal of the current study was to test whether the pathogenesis of ALS involved dysfunction of the innate immune system by using data generated from ALS clinical trials that involved a regulator of the innate immune system, NP001.

The following study investigates relationships between innate immune function and disease activity as defined by quantitative assessment of VC functional measures in NP001-treated as compared to control ALS patients.

Methods

Participants received a total of 20 infusions administered intravenously monthly over 6 cycles during a 6-month double-blind treatment period. Three groups including placebo, 1 mg/kg NP001, and 2 mg/kg NP001 were enrolled. The start of each cycle was separated by four weeks. Cycle 1 consisted of 30 min infusions over 5 consecutive days. Cycles 2, 3, 4, 5, and 6 each consisted of 3 consecutive daily infusions. ALSFRS-R and vital capacity measurements were performed monthly. The average rate of ALS disease progression (Average DP Rate) at baseline was defined as ALSFRS-R score change per month [(48−ALSFRS-R score at baseline)/months since ALS symptom onset from baseline]]. Baseline high-sensitivity CRP (hs-CRP) measurements for all participants were evaluated and baseline plasma hs-CRP of 1.13 mg/L was used as a cutoff point for evaluating the role of inflammation in VC changes over the 6-month study. Plasma specimens for biomarker analysis were obtained at the beginning and end of the study (month 6, one month after last dose). All patients had to have completed the study to provide end of study plasma. The units expressed in this Example are hs-CRP units, abbreviated as CRP.

The clinical outcome data evaluated for the current study were the forced vital capacity measurements performed on all patients at baseline and every month until the end of study. Using the patient's age and height with the actual respiratory volume measured, the % predicted vital capacity (VC) was calculated as described. Patients receiving 1 mg/kg NP001 were excluded from the current efficacy analysis, leaving 31 placebos (18 above CRP 1.13 mg/L, 13 below) and 30 NP001 2 mg/kg-treated (16 above CRP 1.13 mg/L, 14 below) patients who qualified for the VC efficacy analysis.

The phase 2A clinical trial plasma specimens at baseline and at the end of the study were obtained. All patients within the 2 mg/kg NP001-treated and placebo arms who completed the 6-month study and had plasma available from baseline and at the end of the study (6-month completers) were included in the current biomarker study.

Acute phase reactant molecules, CRP and serum amyloid A (SAA) were measured directly and TGFB1 was measured as a surrogate marker for alpha 2 macroglobulin (A2M) activation into a dimeric form that releases preformed TGFB1 when stimulated by hypochlorite. Biomarker levels of baseline and end of study plasma specimens were evaluated at the same time.

Statistical analysis was performed using JMP Pro 16 (SAS Institute, Cary, NC, USA). In general, data were summarized using counts and percentages for categorical data and using standard univariate descriptive statistics (number of participants, mean, standard deviation, median) for continuous data. Analysis of covariance models was used to compare the placebo to each NP001 group for continuous data. The Napierian logarithm (Ln) converted data was used in the data analysis of the non-Gaussian distribution data sets. For all analyses, a two-sided p-value<0.05 was considered statistically significant.

Results

Figure 18:
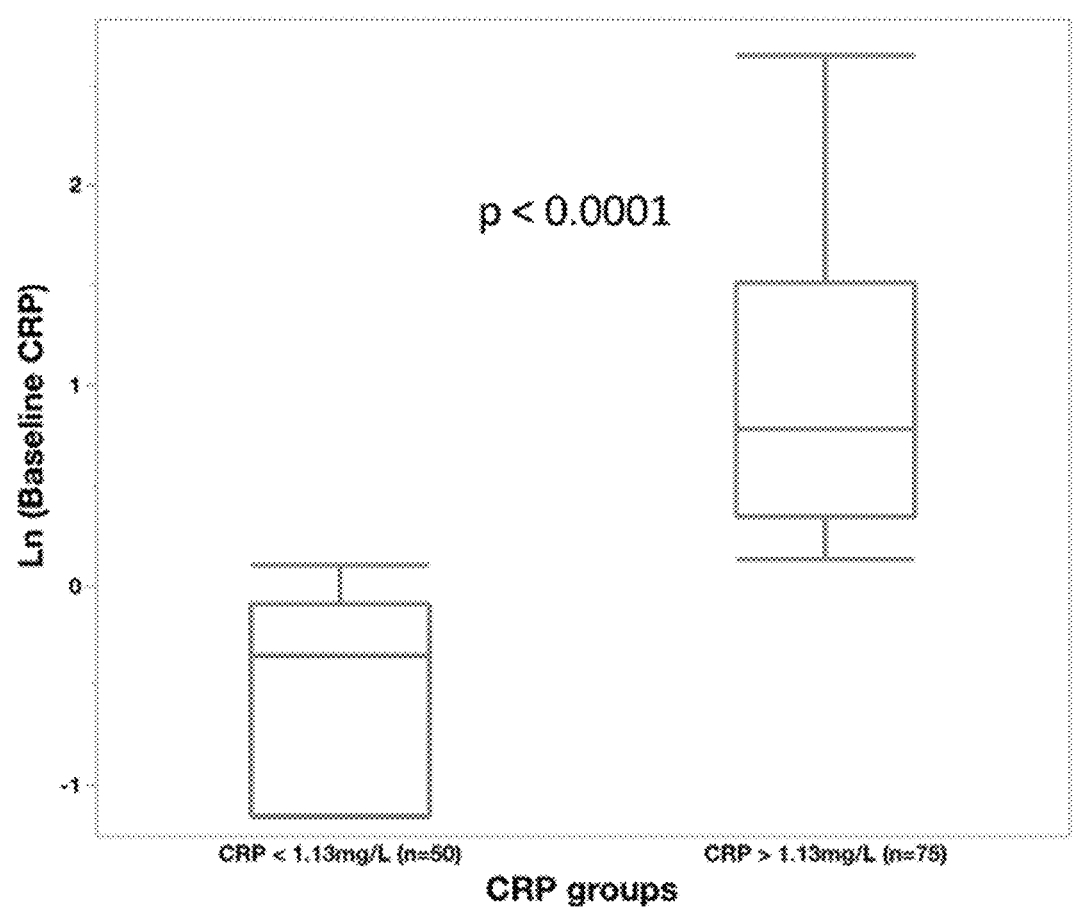
FIG. 18 shows distribution of plasma CRP values from those with baseline CRP<1.13 mg/L vs. baseline CRP>1.13 mg/L. Compared to the group with baseline CRP<1.13 mg/L (n=50), significantly higher levels of baseline CRP were seen in those with CRP>1.13 mg/L at baseline (n=75) (Wilcoxon test, $p<0.0001$). The bottom of each box depicts the first quartile of data, the solid line through each box represents the median, and the top of each box depicts the third quartile of data.

The baseline plasma CRP value of 1.13 mg/L was used to differentiate high from low level patient sets in clinical outcomes in previous studies. FIG. 18 shows that the application of that cutoff point to the NP001 Phase 2A clinical trial participants divided the participant into two CRP level groups. The two groups above and below that cut point had significantly different median CRP values (0.70 mg/L vs 2.17 mg/L in low vs. high groups respectively; p<0.0001). No relationships were observed between baseline values of CRP and ALSFRS-R scores or ages in the NP001 phase 2A studies.

Figure 19:
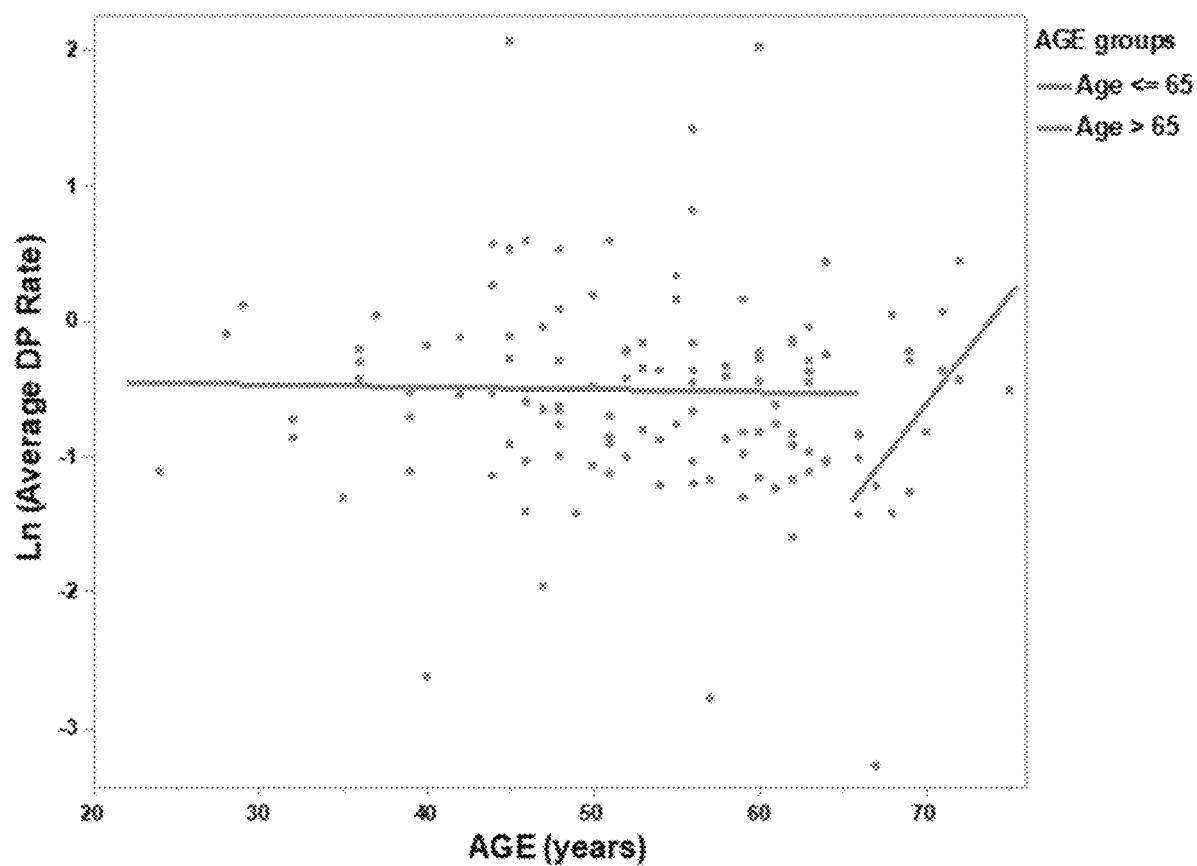
FIG. 19 shows that ALS patients age>65 years exhibited baseline average rates of disease progression (Average DP Rate) different from those patients≤the age of 65 in the phase 2A trial. Positive correlation of Ln (Average DP Rate) and age was observed in the participants with age>65 ($R^2$: 0.25, p=0.04, n=17). No relationship was found in those with age≤65 ($R^2$=0.00, p=0.81, n=108).
Figure 20:
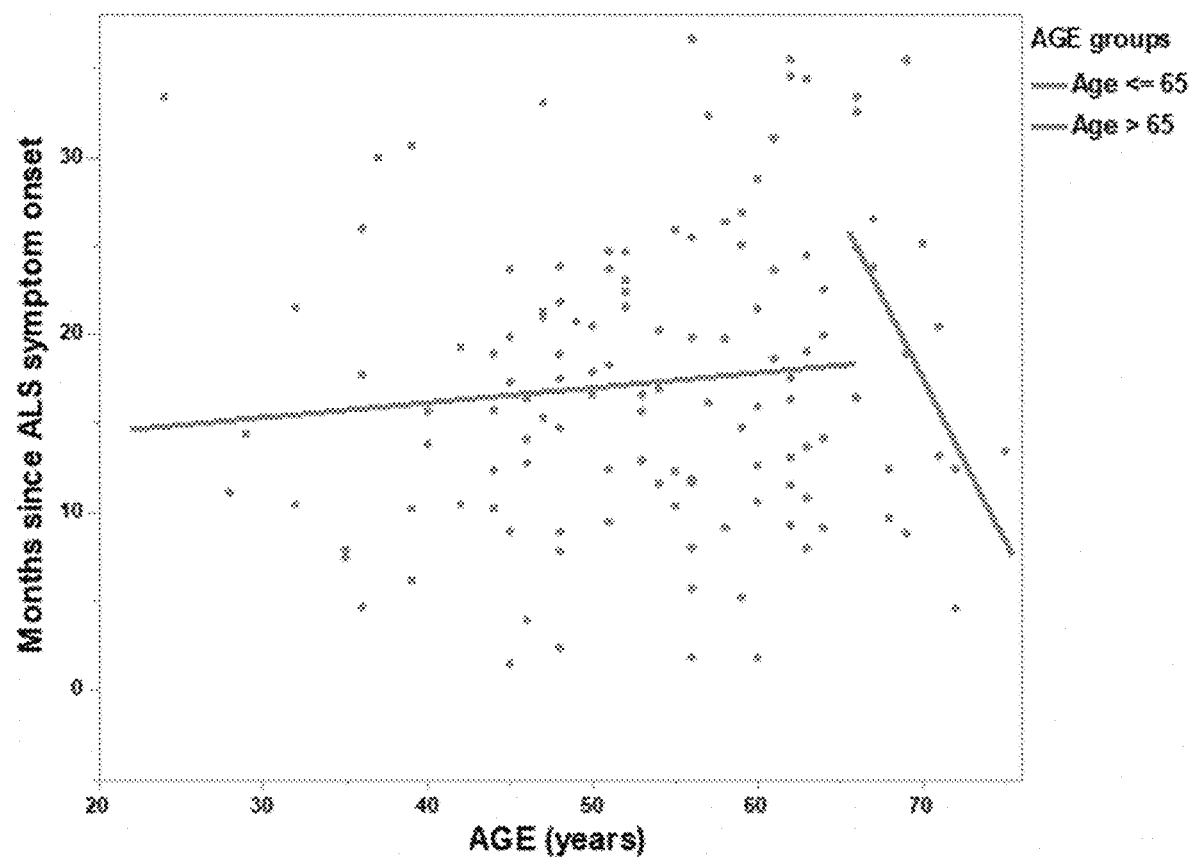
FIG. 20 shows differences in duration of ALS symptom onset from baseline in ALS patients age>65 years of age and patients≤the age of 65. Negative correlation of months since ALS symptom onset and age was observed in the participants with age>65 ($R^2$: 0.27, p=0.03, n=17). No strong correlation was found in those with age≤65 ($R^2$=0.01, p=0.32, n=108).

Although CRP values were unrelated to age, participants over the age of 65 differed significantly in disease activity variables of A) the rate of ALS disease progression (positively correlated with baseline values of CRP, FIG. 19, $R^2=0.25$, p=0.04, n=17), and B) duration of ALS symptom onset (negatively correlated with baseline CRP values, FIG. 20, $R^2=0.27$, p=n=17). Because of the baseline disease activity variability in patients>65, these patients were excluded from further analysis.

Figure 21:
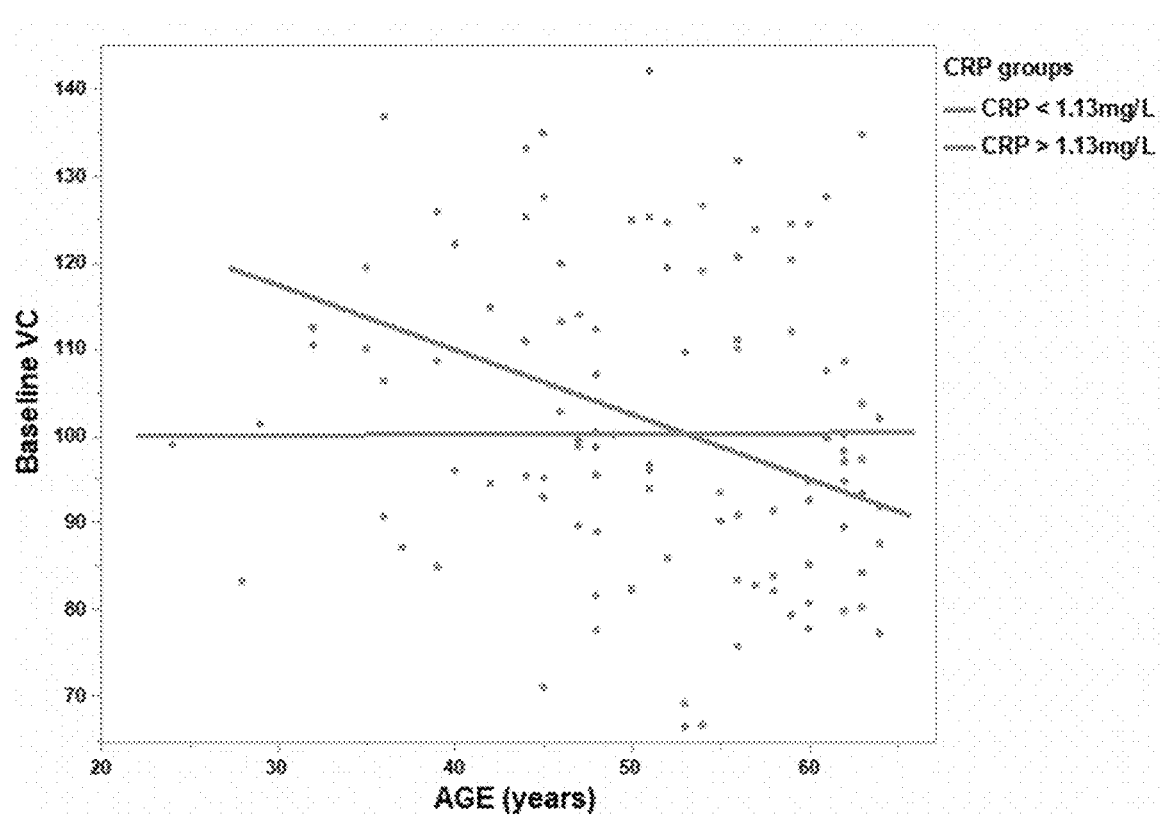
FIG. 21 shows that baseline vital capacity (VC) values worsened with age in ALS patients with low baseline plasma CRP as compared to those with plasma CRP>1.13 mg/L in the participants age≤65. Baseline VC was negatively related to age in the participants with age≤65 and baseline CRP<1.13 mg/L ($R^2$=0.16, p=0.007, n=44). No relationship was found in those with age≤65 and baseline CRP>1.13 mg/L ($R^2$=0.00, p=0.98, n=62).

As shown in FIG. 21, the major difference between high and low CRP patients in relationship to age is in patients with low CRP who had a highly significant age-related decline in baseline level of VC ($R^2=0.16$, p=0.007, n=44) vs the high CRP group where baseline VC values were not associated with age ($R^2=0.00$, p=0.98, n=62). This age-related VC variability in the CRP<1.13 mg/L is the major baseline difference between the high and low CRP group.

Figure 22:
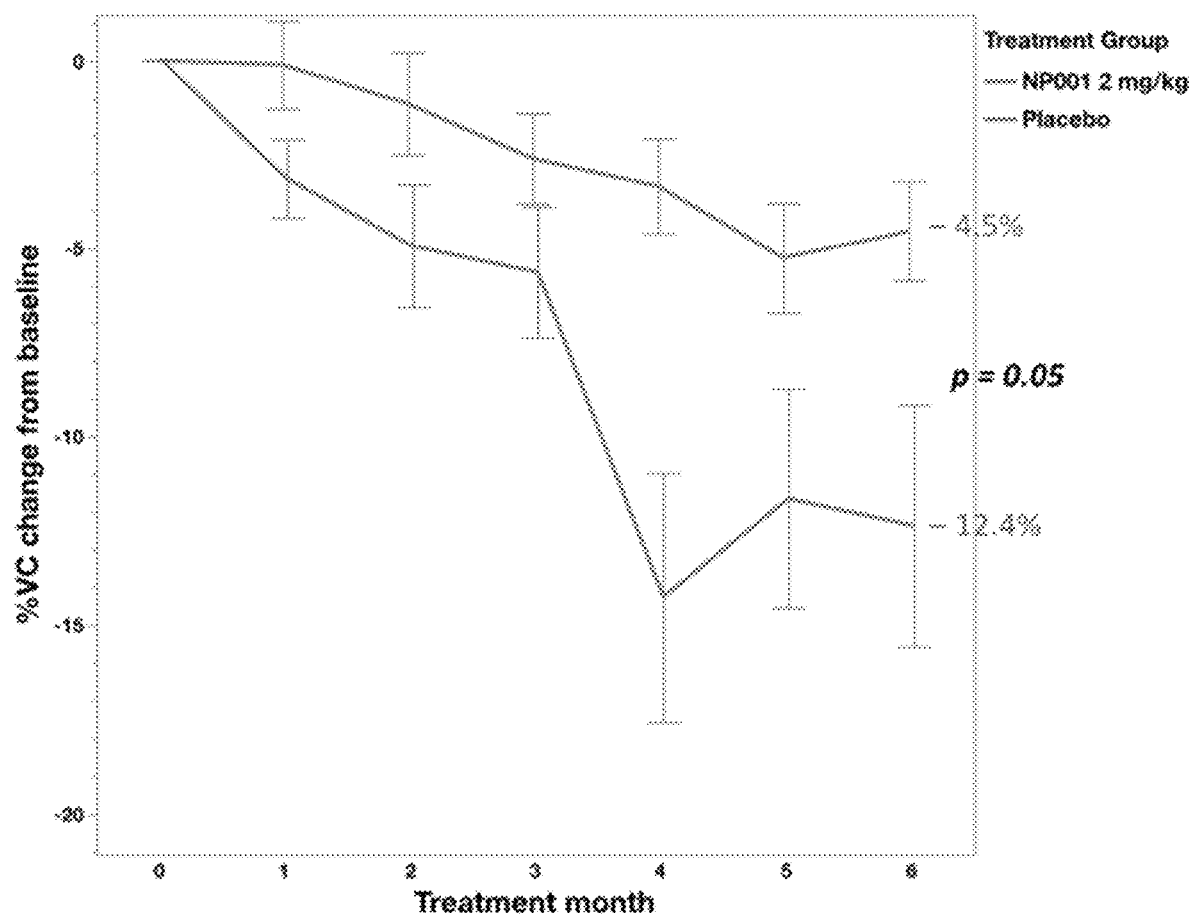
FIG. 22 shows that participants treated with NP001 experienced a slower vital capacity (VC) loss compared to placebo in those age≤65 and plasma CRP>1.13 mg/L at baseline. Bars represent mean of % VC change from baseline±SEM (standard error of the mean). The NP001 treatment group showed a 64% slower VC loss by the end of study (Wilcoxon test, p=0.05).
Figure 23:
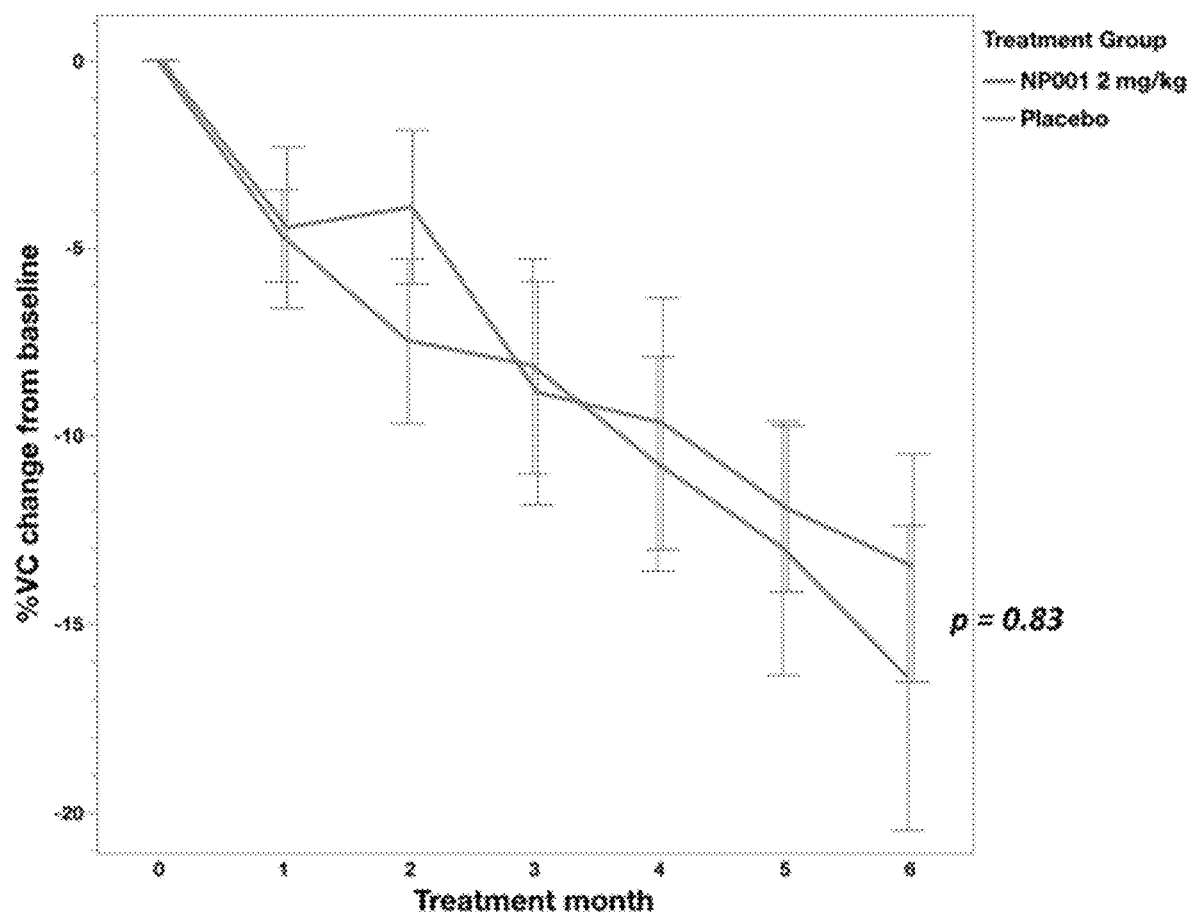
FIG. 23 shows a comparison of vital capacity (VC) change from baseline over the six-month study in participants treated with NP001 compared to placebo in those age≤65 and plasma CRP<1.13 mg/L at baseline. Bars represent mean of % VC change from baseline±SEM (standard error of the mean). No significant differences were seen between NP001 and placebo groups by the end of study (NP001=−16.4% vs. Placebo=−13.5%) (Wilcoxon test, p=0.83).

To test whether the VC disparity is associated with different clinical outcomes in patients treated with NP001, the phase 2A study was evaluated in patients treated with NP001 vs. placebo in the high vs. low baseline CRP groups. FIG. 22 shows that VC was improved in NP001 treated as compared to placebo, whereas in patients in the low baseline CRP group, NP001 treatment showed no effect above placebo (FIG. 23). The high CRP group placebos lost an average of 2.1% VC per month vs. NP001 treated 0.75% VC lost per month, a >64% slower rate of VC loss with NP001 (p=0.05).

These two groups of patient demographics including rates of disease progression, age, and severity of disease at presentation were essentially the same. TABLE 7 shows the comparisons between the NP001 treated vs placebo group that was ≤65 and had baseline CRP>1.13 mg/L. TABLE 8 shows the same age group with baseline CRP<1.13 mg/L.

TABLE 7. Baseline demographics and characteristics of phase 2A completers treated with NP001 vs Placebo in those age≤65 years and plasma CRP>1.13 mg/L.

| Characteristics | NP001 2 mg/kg (n = 16) | Placebo (n = 18) | Overall (n = 34) |
|---|---|---|---|
| Sex, n (%) | | | |
| Female | 5 (31.3%) | 5 (27.8%) | 10 (29.4%) |
| Male | 11 (68.8%) | 13 (72.2%) | 24 (70.6%) |
| Age at baseline, year | 51.9 ± 9.9 | 51.8 ± 5.9 | 51.9 ± 7.9 |
| Type of ALS, n (%) | | | |
| Familial | 0 (0.0%) | 2 (11.1%) | 2 (5.9%) |
| Sporadic | 16 (100.0%) | 16 (88.9%) | 32 (94.1%) |
| Site of ALS onset, n (%) | | | |
| Bulbar | 3 (18.8%) | 3 (16.7%) | 6 (17.6%) |
| Limb | 13 (81.3%) | 15 (83.3%) | 28 (82.4%) |
| El Escorial criteria for ALS, n (%) | | | |
| Definite | 7 (43.8%) | 9 (50.0%) | 16 (47.1%) |
| Probable | 8 (50.0%) | 7 (38.9%) | 15 (44.1%) |
| Possible | 1 (6.3%) | 2 (11.1%) | 3 (8.8%) |
| Concurrent riluzole use, n (%) | | | |
| Yes | 11 (68.8%) | 12 (66.7%) | 23 (67.6%) |
| No | 5 (31.3%) | 6 (33.3%) | 11 (32.4%) |
| ALSFRS-R score at baseline [1], Mean ± SD | 37.7 ± 4.1 | 39.2 ± 3.9 | 38.5 ± 4.0 |
| Vital capacity at baseline, Mean ± SD | 113.5 ± 17.0 | 109.2 ± 15.3 | 111.2 ± 16.0 |
| Months since ALS symptom onset [2], Mean ± SD | 19.29 ± 7.63 | 13.76 ± 6.55 | 16.36 ± 7.52 |
| CRP at Baseline (mg/L) [3], Mean ± SD | 3.48 ± 2.57 | 2.95 ± 2.24 | 3.291 ± 2.38 |

Abbreviation: n, number of participants. SD, Standard Deviation.
[1] ALSFRS-R score: The revised Amyotrophic lateral sclerosis functional rating scale.
[2] Months from ALS symptom onset to baseline.
[3] Baseline plasma levels of C-Reactive Protein.

TABLE 8. Baseline demographics and characteristics of 2A completers treated with NP001 vs Placebo in those age≤65 years and plasma CRP<1.13 mg/L.

| Characteristics | NP001 2 mg/kg (n = 14) | Placebo (n = 13) | Overall (n = 27) |
|---|---|---|---|
| Sex, n (%) | | | |
| Female | 5 (35.7%) | 4 (30.8%) | 9 (33.3%) |
| Male | 9 (64.3%) | 9 (69.2%) | 18 (66.7%) |
| Age at baseline, year | 51.3 ± 8.9 | 51.8 ± 11.6 | 51.6 ± 10.1 |
| Type of ALS, n (%) | | | |
| Familial | 1 (7.1%) | 2 (15.4%) | 3 (11.1%) |
| Sporadic | 13 (92.9%) | 11 (84.6%) | 24 (88.9%) |
| Site of ALS onset, n (%) | | | |
| Bulbar | 2 (14.3%) | 2 (15.4%) | 4 (14.8%) |
| Limb | 12 (85.7%) | 11 (84.6%) | 23 (85.2%) |
| El Escorial criteria for ALS, n (%) | | | |
| Definite | 7 (50.0%) | 7 (53.8%) | 14 (51.9%) |
| Probable | 7 (50.0%) | 6 (46.2%) | 13 (48.1%) |
| Concurrent riluzole use, n (%) | | | |
| Yes | 10 (71.4%) | 9 (69.2%) | 19 (70.4%) |
| No | 4 (28.6%) | 4 (30.8%) | 8 (29.6%) |
| ALSFRS-R score at baseline [1], Mean ± SD | 38.4 ± 6.5 | 40.0 ± 3.2 | 39.2 ± 5.1 |
| Vital capacity at baseline, Mean ± SD | 110.3 ± 15.7 | 110.8 ± 19.0 | 110.6 ± 17.1 |
| Months since ALS symptom onset [2], Mean ± SD | 13.60 ± 7.18 | 16.56 ± 7.68 | 15.02 ± 7.43 |
| CRP at Baseline (mg/L) [3], Mean ± SD | 0.73 ± 0.26 | 0.62 ± 0.30 | 0.68 ± 0.28 |

Abbreviation: n, number of participants. SD, Standard Deviation.
[1] ALSFRS-R score: The revised Amyotrophic lateral sclerosis functional rating scale.
[2] Months from ALS symptom onset to baseline.
[3] Baseline plasma levels of C-Reactive Protein.

Figure 24:
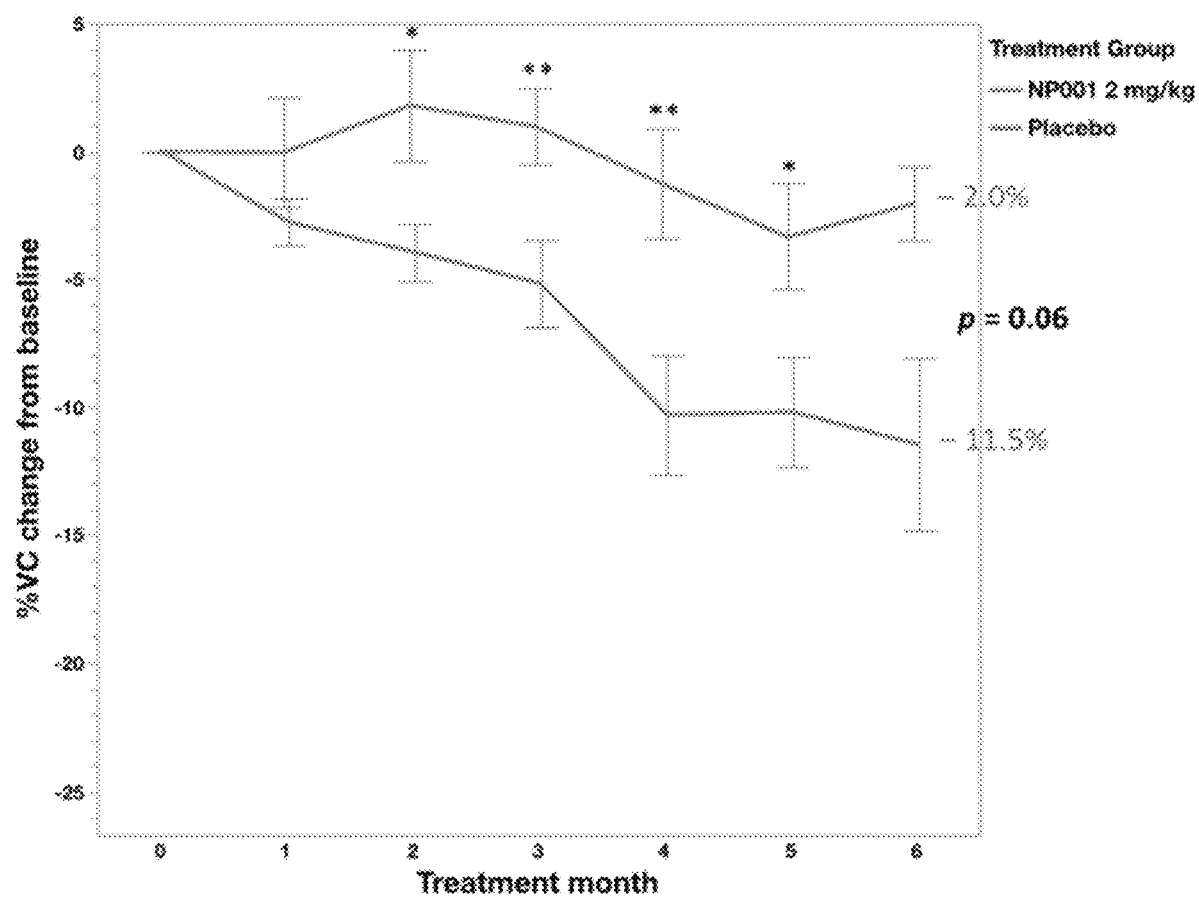
FIG. 24 shows that participants treated with NP001 exhibiting ALS symptoms for less than 16.2 months showed a slower vital capacity (VC) loss compared to placebo subjects. Bars represent mean of % VC change from baseline±SEM (standard error of the mean). The NP001 treatment group showed differences starting from the month 2 (Wilcoxon test, *, p<0.04 & **, p<0.02).
Figure 25:
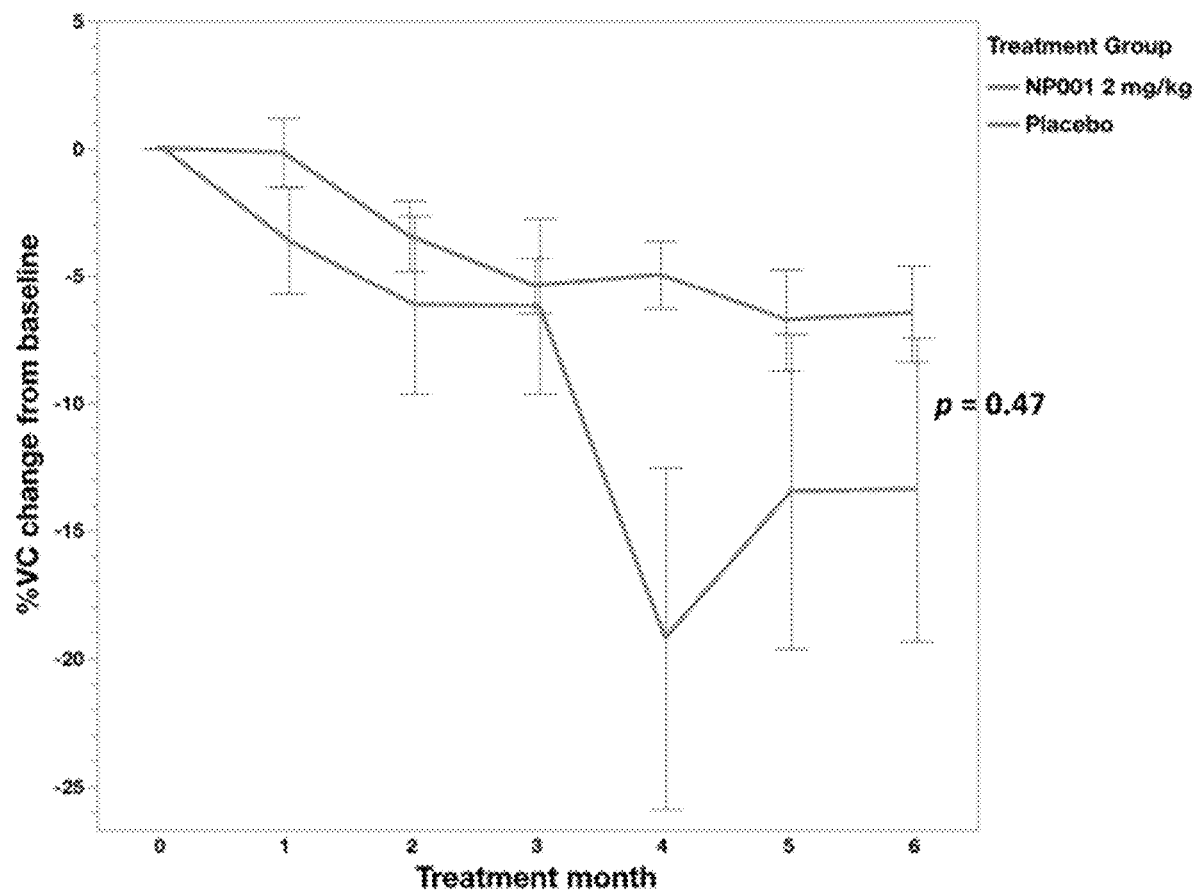
FIG. 25 shows a comparison of vital capacity (VC) change from baseline over the six-month study in participants treated with NP001 exhibiting ALS symptoms for greater than 16.2 months compared to placebo. % VC change from baseline for participants treated with NP001 (n=9) depicted in blue and compared to placebo group (n=8) depicted in red. Bars represent mean of % VC change from baseline±SEM (standard error of the mean).

To test whether the VC sparing activity noted in FIG. 22 would be more pronounced early after symptom onset, the patient groups (placebo and 2 mg/kg NP001) were separated into two, based on the median time since symptom onset of 16.2 months. FIG. 24 shows the VC change from baseline over time in ALS patients below the median in the treated to be significantly different from placebo beginning at 2 months after initiation of therapy. FIG. 25 shows that even though the above median timepoint treated had a slower rate of decline than the placebos did, that difference was not statistically significant.

Figure 26:
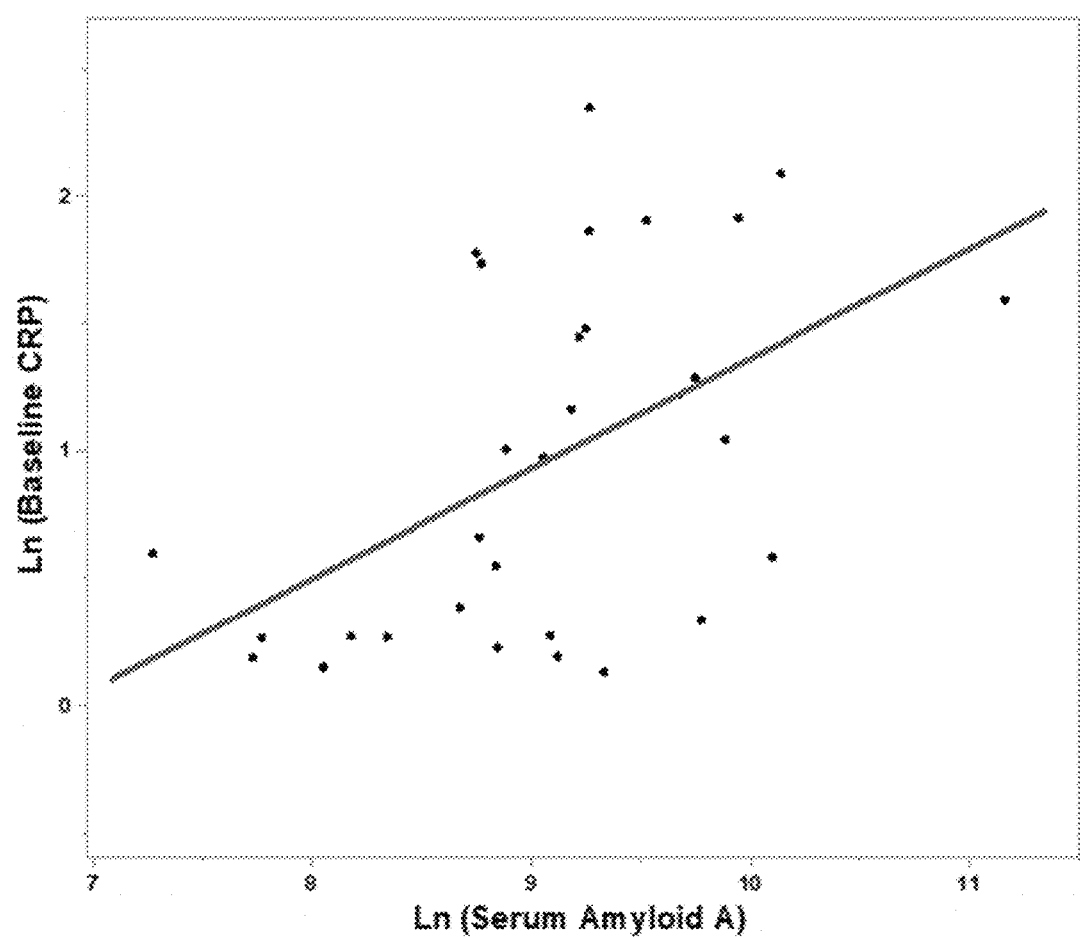
FIG. 26 shows a positive correlation of baseline plasma CRP and the levels of plasma Serum Amyloid A (SAA) in ALS patients age≤65 and plasma CRP>1.13 mg/L at baseline ($R^2$=0.25, p=0.004, n=31).

To test whether NP001 affects the innate immune system function, factors related to innate immune system regulation were measured. FIG. 26 shows the direct relationship between plasma levels of the acute phase reactant serum amyloid A (SAA) and CRP ($R^2$=0.25, p=0.004, n=31) confirming that the immune activation in patients with CRP>1.13 mg/L is not isolated but a component of a generalized acute phase reaction.

Figure 27:
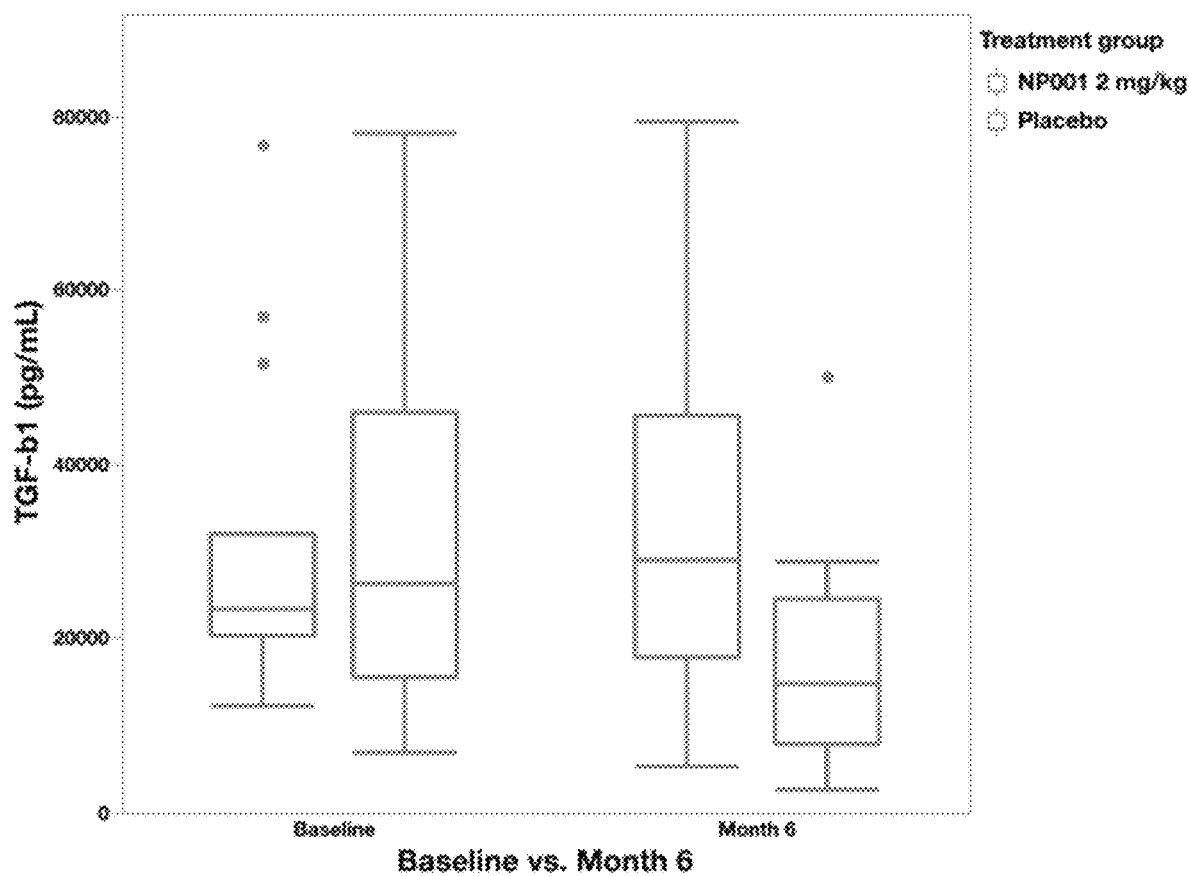
FIG. 27 shows that the levels of TGFB1 significantly increased over the 6-month trial in NP001 treatment compared to placebo controls in those with age≤65 and baseline CRP>1.13 mg/L. NP001 (n=15) vs. Placebo (n=16): Wilcoxon test, p=0.89 for baseline and p=0.02 for month 6.

Plasma TGFB1 was evaluated for evidence for alpha 2 macroglobulin (A2M) activation, another major component of the innate immune system in patients responsive clinically to NP001. FIG. 27 shows that TGFB1 levels increased significantly in patients with baseline CRP>1.13 mg/L who received NP001 over the 6-month trial as compared to placebo controls. A greater than 95% increase in plasma TGFB1 occurred post exposure to NP001 vs. placebo suggests that the NP001 caused an A2M dimerization with release of TGFB1. The elevated level of TGFB1 one month after the last dose of NP001 also suggests that the other function of A2M dimers, the clearance of misfolded proteins, can reset the innate immune activation cycle.

Figure 28:
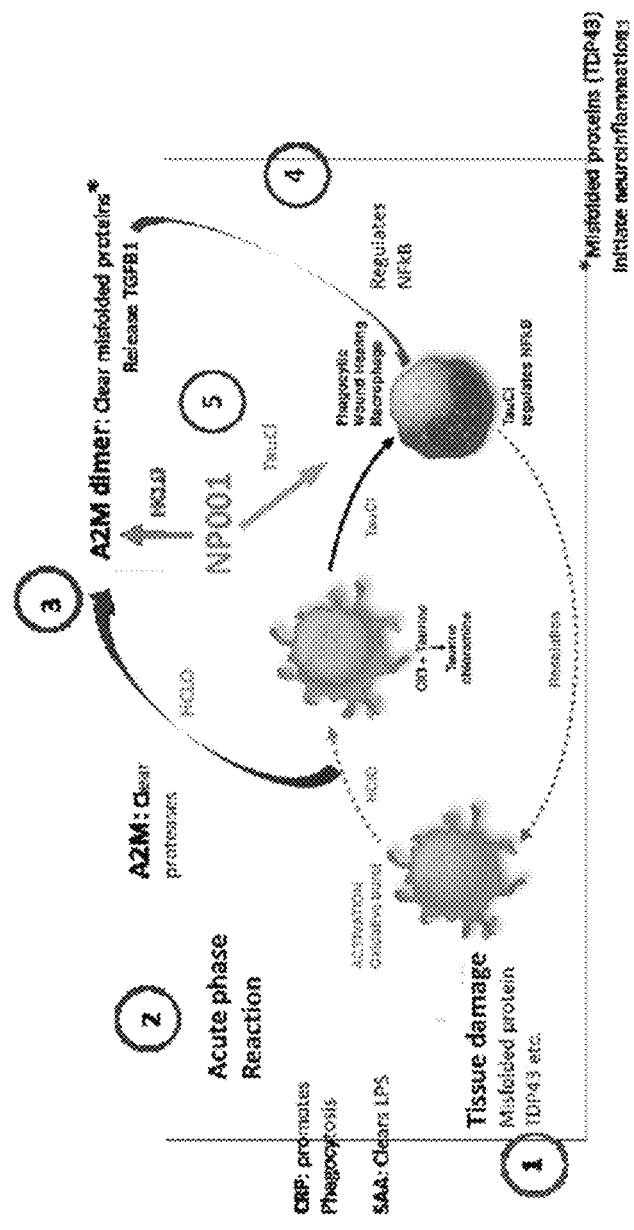
FIG. 28 shows the augmentation of the innate immune activation cycle in ALS patients with elevated baseline plasma CRP with NP001.

FIG. 28 shows a schematic that demonstrates how the innate immune system self regulates normally and can be augmented by the addition of NP001. The acute phase reaction occurs in response to aggregated or misfolded proteins like TDP-43. Both CRP and SAA respond in parallel as in a normal acute phase response, but in a subset of ALS patients, a persistence of these factors is observed in the plasma (step 1). The innate inflammatory response is associated with an oxidative burst and the production of hypochlorous acid (HCLO) which activates alpha 2 macroglobulin (A2M) to bind and clear proteases (step 2). The normal oxidative burst byproduct HClO is converted to taurine chloramine (TauCL) a regulator of NFkB and inflammation. With excess HClO, A2M dimerizes and releases preformed TGFB1 and binds to and clears misfolded proteins (step 3). TGFB1 feeds back on proinflammatory cells and turns off NFkB. (Step 4). NP001 is converted in vivo to HCLO and stimulates step 3 and 4 of the innate immune system regulation cycle (step 5). The greater than 95% increased plasma level of TGFB1 in ALS patients who received NP001 and show a vital capacity clinical response serves to confirm these activities. In the evaluation of CRP plasma level as an independent variable in this trial, no relationship was found between CRP level and age or baseline ALSFRS-R scores. Indirect measures of ALS disease activity, the duration of disease before study and the rate of ALSFRS-R score loss was unrelated to CRP level except in those patients>65 years of age who showed significant differences in both measures in relation to CRP. Subsequent evaluations were performed only on the patients≤65. The only major variable related to baseline CRP level was the age associated loss of VC in patients with low as compared to high plasma CRP, suggesting a link between the innate immune system and respiratory function.

FIG. 28 shows how NP001 augments the innate immune activation cycle in ALS patients who have elevated baseline plasma CRP. The innate immune activation cycle is a rapid and controlled multistep self-regulated process that occurs after exposure of the immune system to infections or tissue damage. In the case of ALS, the most likely initiator of innate immune system activation is the presence of misfolded and or aggregated proteins such as TDP43 or SOD1 in the neuromuscular junction. Step 1: Blood derived macrophages become activated and begin clearance of cells and tissues containing pathogenic proteins and elaborate factors that initiate the acute phase reaction, producing hypochlorous acid as a byproduct of oxidative burst activation. Step 2: Rapid elevation of acute phase reactants including CRP and SAA, both of which amplify>30×; CRP facilitates clearance of damaged tissues and cells, SAA binds to and clears bacterial byproducts such as LPS. Alpha 2 macroglobulin becomes activated to absorb and remove damaged cell products such as proteases. Anti-inflammatory signaling begins. Step 3: Hypochlorous acid stimulates 1) production of the immune activation regulator taurine chloramine (TauCl). TauCl regulates macrophages to become phagocytic and wound healing and 2) A2M to dimerize and change function. A2M dimers clear misfolded proteins and release pre-synthesized TGFB1 to feedback on proinflammatory processes such as those driven by NFkB. Step 4: TGFB1 is a potent regulator of NFkB and inflammation. Macrophages exposed to TGFB1 become regulators of proinflammatory cells and the innate immune activation cycle is completed. Step 5: NP001 is converted by heme iron to hypochlorite which stimulates steps 3 and 4. TauCl regulates macrophages and hypochlorite stimulates further dimerization of A2M and release of TGFB1.

To test whether the observed VC sparing effect associated with NP001 treatment would be more pronounced early in disease, the patients were split into two groups based on the median time from symptom onset of 16.2 months. The below median group showed a significant difference between treated and placebos beginning at the two-month time point that was maintained throughout the 6-month study. The group that was above the median since symptom onset showed less robust activity at VC sparing with borderline significance only occurring at the 4-month time point. The data shown here confirm that respiratory function is measurably failing early the disease, as NP001 augmentation of innate immunity slows VC loss from the earliest time point. Second, even in ALS patients with a later initiation of NP001, the rate of VC loss is still slower than the VC loss in placebos.

CRP levels of at least 1.13 mg/L were required to show baseline stability of VC in ALS patients stratified by age. The finding of a significant loss of VC related to age in patients with low CRP suggests that CRP plays a role in stabilizing the innate immune system in relation to respiratory function. In addition, NP001 can augment components of the immune activation cycle through the production of immunoregulatory molecules TauCL and TGFB1.

Another critical component of the humoral innate immune system is Alpha-2-macroglobulin (A2M). A2M is a large plasma protein that binds and remove proteases that are byproducts of the oxidate burst process. A2M forms a dimer when in contact with excess HOCl, a product of the oxidative burst process. This dimer binds to and clears misfolded and aggregated proteins thought to be initiators of the inflammatory processes associated with neurodegenerative diseases. The dimer also releases preformed TGFB1, thereby sending a signal to the immune system to suppress proinflammatory signals such those driven by NFkB. The steps in a successful innate immune system regulatory cycle described in this study include: 1) CRP facilitation and initiation of a feedback loop; 2) the oxidative burst byproduct HOCL converted to immune regulator taurine chloramine (TauCl); and 3) release of TGFB1 from A2M dimers to suppress inflammation further. NP001 when converted to HOCL has an amplifier effect on this self-regulatory cycle. In the data presented, the level of plasma TGFB1 was 95% greater in NP001-treated as compared to placebos after 6 months. Given the 2-minute plasma half-life of TGFB1 and the fact that NP001 was last administered a month before testing the plasma specimens, the results suggest re-establishment of control of the innate immune system that in the context of disease has become ineffective.

In the current study, ALS patient VC was measured over time after initiation. High CRP patients showed a >64% improvement of VC function as compared to high CRP placebos; low CRP patients showed no response to NP001. These results suggest that disease activity and response to innate immune system-directed therapy could be followed by monitoring VC in conjunction with tracking of plasma TGFB1 levels.

EMBODIMENTS

Embodiment 1. A method comprising:
a) identifying that a subject has a ratio of LPS:EGF associated with ALS; and
b) based on the identifying that the subject has the ratio of LPS:EGF associated with ALS, determining that the subject is eligible for sodium chlorite therapy for the ALS.

Embodiment 2. The method of embodiment 1, wherein the ratio of LPS:EGF associated with ALS is no greater than 50.

Embodiment 3. The method of embodiment 1 or 2, wherein the subject has ALS.

Embodiment 4. The method of any one of embodiments 1-3, wherein the subject is at least age 40.

Embodiment 5. The method of any one of embodiments 1-4, wherein the subject possesses a CRP level greater than 1.13 mg/L as determined by a blood assay.

Embodiment 6. The method of any one of embodiments 1-5, wherein the sodium chlorite therapy is about 0.2 mg/kg/day to about 3.5 mg/kg/day.

Embodiment 7. The method of any one of embodiments 1-6, further comprising recommending that the subject undergo the sodium chlorite therapy for the ALS based on the determining that the subject is eligible for sodium chlorite therapy for the ALS.

Embodiment 8. The method of any one of embodiments 1-7, further comprising administering to the subject the sodium chlorite therapy.

Embodiment 9. The method of any one of embodiments 1-8, further comprising orally administering to the subject the sodium chlorite therapy.

Embodiment 10. The method of any one of embodiments 1-8, further comprising parenterally administering to the subject the sodium chlorite therapy.

Embodiment 11. The method of any one of embodiments 1-10, wherein the identifying that the subject has the ratio of LPS:EGF associated with ALS is done by obtaining a result from an assay of the subject.

Embodiment 12. The method of embodiment 11, further comprising performing the assay of the subject to obtain the result.

Embodiment 13. The method of embodiment 11 or 12, wherein the assay is a blood assay.

Embodiment 14. The method of any one of embodiments 11-13, wherein the assay is a quantification of LPS and EGF in blood of the subject by high performance liquid chromatography.

Embodiment 15. A method of treating ALS in a subject in need thereof, the method comprising:
 a) identifying that a subject has a ratio of LPS:EGF associated with ALS; and
 b) based on the identifying that the subject has the ratio of LPS:EGF associated with ALS, administering to the subject an amount of sodium chlorite that is therapeutically-effective for ALS.

Embodiment 16. The method of embodiment 15, wherein the ratio of LPS:EGF associated with ALS is no greater than 50.

Embodiment 17. The method of embodiment 15 or 16, wherein the subject is at least age 40.

Embodiment 18. The method of any one of embodiments 15-17, wherein the amount is about 0.2 mg/kg/day to about 3.5 mg/kg/day.

Embodiment 19. The method of any one of embodiments 15-18, wherein the administering is oral.

Embodiment 20. The method of any one of embodiments 15-18, wherein the administering is parenteral.

Embodiment 21. The method of any one of embodiments 15-20, wherein the identifying that the subject has the ratio of LPS:EGF associated with ALS is done by obtaining a result from an assay of the subject.

Embodiment 22. The method of embodiment 21, further comprising performing the assay of the subject to obtain the result.

Embodiment 23. The method of embodiment 21 or 22, wherein the assay is a blood assay.

Embodiment 24. The method of any one of embodiments 21-23, wherein the assay is a quantification of LPS and EGF in blood of the subject by high performance liquid chromatography.

Embodiment 25. A method comprising:
 a) determining a ratio of LPS:EGF in a subject that has ALS, wherein the subject is undergoing a treatment for the ALS, wherein the treatment is a therapeutic regimen of sodium chlorite; and
 b) determining based on the ratio of LPS:EGF whether to continue the therapeutic regimen of sodium chlorite.

Embodiment 26. The method of embodiment 25, wherein the ratio of LPS:EGF in the subject is no greater than 50.

Embodiment 27. The method of embodiment 25 or 26, wherein the subject is at least age 40.

Embodiment 28. The method of any one of embodiments 25-27, wherein the therapeutic regimen of sodium chlorite is about 0.2 mg/kg/day to about 3.5 mg/kg/day.

Embodiment 29. The method of any one of embodiments 25-28, wherein the therapeutic regimen of sodium chlorite is administered orally.

Embodiment 30. The method of any one of embodiments 25-28, wherein the therapeutic regimen of sodium chlorite is administered parenterally.

Embodiment 31. The method of any one of embodiments 25-30, further comprising determining to continue the therapeutic regimen of sodium chlorite.

Embodiment 32. The method of any one of embodiments 25-30, further comprising determining to discontinue the therapeutic regimen of sodium chlorite.

Embodiment 33. The method of any one of embodiments 25-32, wherein the determining the ratio of LPS:EGF in the subject is done by obtaining a result from an assay of the subject.

Embodiment 34. The method of embodiment 33, further comprising performing the assay of the subject to obtain the result.

Embodiment 35. The method of embodiment 33 or 34, wherein the assay is a blood assay.

Embodiment 36. The method of any one of embodiments 33-35, wherein the assay is a quantification of LPS and EGF in blood of the subject by high performance liquid chromatography.

Embodiment 37. A method comprising:
 a) obtaining a first level of inflammatory macrophages in a gut epithelium of a subject who has ALS, wherein the first level of inflammatory macrophages in the gut epithelium of the subject who has ALS is based on a blood assay;
 b) based at least in part on the first level of inflammatory macrophages in the gut epithelium of the subject, starting the subject on a regimen of sodium chlorite administration for a time period of about six months;
 c) after the time period, obtaining a second level of inflammatory macrophages in the gut epithelium of the subject;
 d) determining that the second level of inflammatory macrophages in the gut epithelium of the subject is lower than the first level of inflammatory macrophages in the gut epithelium of the subject by a predetermined threshold amount; and
 e) based at least in part on the determining that the second level of inflammatory macrophages in the gut epithelium of the subject is lower than the first level of inflammatory macrophages in the gut epithelium of the subject by the predetermined threshold amount, recommending that the subject continue the regimen of sodium chlorite administration.

Embodiment 38. The method of embodiment 37, wherein the subject is at least age 40.

Embodiment 39. The method of embodiment 37 or 38, wherein the subject possesses a CRP level greater than 1.13 mg/L as determined by a blood assay.

Embodiment 40. The method of any one of embodiments 37-39, wherein the regimen of sodium chlorite is about 0.2 mg/kg/day to about 3.5 mg/kg/day.

Embodiment 41. The method of any one of embodiments 37-40, wherein the regimen of sodium chlorite is administered orally.

Embodiment 42. The method of any one of embodiments 37-40, wherein the regimen of sodium chlorite is administered parenterally.

Embodiment 43. The method of any one of embodiments 37-42, further comprising determining to continue the regimen of sodium chlorite.

Embodiment 44. The method of any one of embodiments 37-42, further comprising determining to discontinue the regimen of sodium chlorite.

Embodiment 45. The method of any one of embodiments 37-44, wherein the blood assay is a quantification of inflammatory macrophages in blood of the subject by high performance liquid chromatography.

Embodiment 46. A method comprising:
  a) obtaining a first plasma neurofilament light chain level of a subject who has ALS, wherein the first plasma neurofilament light chain level of the subject who has ALS is based on a blood assay;
  b) based at least in part on the first plasma neurofilament light chain level of the subject, starting the subject on a regimen of sodium chlorite administration for a time period of about six months;
  c) after the time period, obtaining a second plasma neurofilament light chain level of the subject;
  d) determining that the second plasma neurofilament light chain level of the subject is a decrease of at least a predetermined threshold amount in comparison to the first plasma neurofilament light chain level of the subject; and
  e) based at least in part on the determining that the second plasma neurofilament light chain level of the subject is a decrease of at least the predetermined threshold amount in comparison to the first plasma neurofilament light chain level of the subject, recommending that the subject continue the regimen of sodium chlorite administration.

Embodiment 47. The method of embodiment 46, wherein the subject is at least age 40.

Embodiment 48. The method of embodiment 46 or 47, wherein the subject possesses a CRP level greater than 1.13 mg/L as determined by a blood assay.

Embodiment 49. The method of any one of embodiments 46-48, wherein the regimen of sodium chlorite is about 0.2 mg/kg/day to about 3.5 mg/kg/day.

Embodiment 50. The method of any one of embodiments 46-49, wherein the regimen of sodium chlorite is administered orally.

Embodiment 51. The method of any one of embodiments 46-49, wherein the regimen of sodium chlorite is administered parenterally.

Embodiment 52. The method of any one of embodiments 46-51, further comprising determining to continue the regimen of sodium chlorite.

Embodiment 53. The method of any one of embodiments 46-51, further comprising determining to discontinue the regimen of sodium chlorite.

Embodiment 54. The method of any one of embodiments 46-53, wherein the blood assay is a quantification of neurofilament light chain levels in blood of the subject by high performance liquid chromatography.

Embodiment 55. A method of treating ALS in a subject in need thereof, the method comprising:
  a) obtaining a first level of a first biomarker in the subject;
  b) obtaining a first level of the second biomarker in the subject;
  c) after obtaining the first level of the first biomarker in the subject and obtaining the first level of the second biomarker in the subject, starting the subject on a regimen of sodium chlorite administration for a time period of at least about six months;
  d) after the time period, obtaining a second level of the first biomarker in the subject;
  e) after the time period, obtaining a second level of the second biomarker in the subject;
  f) determining that the first level of the first biomarker in the subject is greater than the second level of the first biomarker in the subject;
  g) determining that the first level of the second biomarker in the subject is lesser than the second level of the second biomarker in the subject; and
  h) based at least in part on the determining that the first level of the first biomarker in the subject is greater than the second level of the first biomarker in the subject and the determining that the first level of the second biomarker in the subject is lesser than the second level of the second biomarker in the subject, recommending that the subject continue the regimen of sodium chlorite administration.

Embodiment 56. The method of embodiment 55, wherein the subject is at least age 40.

Embodiment 57. The method of embodiment 55 or 56, wherein the first biomarker is LPS.

Embodiment 58. The method of any one of embodiments 55-57, wherein the second biomarker is EGF.

Embodiment 59. The method of any one of embodiments 55-58, wherein the subject possesses a CRP level greater than 1.13 mg/L as determined by a blood assay.

Embodiment 60. The method of any one of embodiments 55-59, wherein the regimen of sodium chlorite is about 0.2 mg/kg/day to about 3.5 mg/kg/day.

Embodiment 61. The method of any one of embodiments 55-60, wherein the regimen of sodium chlorite is administered orally.

Embodiment 62. The method of any one of embodiments 55-60, wherein the regimen of sodium chlorite is administered parenterally.

Embodiment 63. The method of any one of embodiments 55-62, further comprising determining to continue the regimen of sodium chlorite.

Embodiment 64. The method of any one of embodiments 55-62, further comprising determining to discontinue the regimen of sodium chlorite.

Embodiment 65. The method of any one of embodiments 55-64, wherein the determining that the first level of the first biomarker in the subject is greater than the second level of the first biomarker is done by obtaining a result from an assay of the subject.

Embodiment 66. The method of any one of embodiments 55-65, wherein the determining that the first level of the second biomarker in the subject is lesser than the second level of the second biomarker is done by obtaining a result from an assay of the subject.

Embodiment 67. The method of any one of embodiments 55-66, further comprising performing the assay of the subject to obtain the result.

Embodiment 68. The method of embodiment 67, wherein the assay is a blood assay.

Embodiment 69. The method of embodiment 67 or 68, wherein the assay is a quantification of the first biomarker and the second biomarker in blood of the subject by high performance liquid chromatography.

Embodiment 70. A method comprising:
a) identifying that a subject has a level of TGFB1 associated with ALS; and
b) based on the identifying that the subject has the level of TGFB1 associated with ALS, determining that the subject is eligible for sodium chlorite therapy for the ALS.

Embodiment 71. The method of embodiment 70, wherein the subject has ALS.

Embodiment 72. The method of embodiment 70 or 71, wherein the subject is at least age 40.

Embodiment 73. The method of any one of embodiments 70-72, wherein the subject possesses a CRP level greater than 1.13 mg/L as determined by a blood assay.

Embodiment 74. The method of any one of embodiments 70-73, wherein the sodium chlorite therapy is about 0.2 mg/kg/day to about 3.5 mg/kg/day.

Embodiment 75. The method of any one of embodiments 70-74, further comprising recommending that the subject undergo the sodium chlorite therapy for the ALS based on the determining that the subject is eligible for sodium chlorite therapy for the ALS.

Embodiment 76. The method of any one of embodiments 70-75, further comprising administering to the subject the sodium chlorite therapy.

Embodiment 77. The method of any one of embodiments 70-76, further comprising orally administering to the subject the sodium chlorite therapy.

Embodiment 78. The method of any one of embodiments 70-76, further comprising parenterally administering to the subject the sodium chlorite therapy.

Embodiment 79. The method of any one of embodiments 70-78, wherein the identifying that the subject has the level of TGFB1 associated with ALS is done by obtaining a result from an assay of the subject.

Embodiment 80. The method of embodiment 79, further comprising performing the assay of the subject to obtain the result.

Embodiment 81. The method of embodiment 79 or 80, wherein the assay is a blood assay.

Embodiment 82. The method of any one of embodiments 79-81, wherein the assay is a quantification of TGFB1 in blood of the subject by high performance liquid chromatography.

Embodiment 83. A method of treating ALS in a subject in need thereof, the method comprising:
a) identifying that a subject has a level of TGFB1 associated with ALS; and
b) based on the identifying that the subject has the level of TGFB1 associated with ALS, administering to the subject an amount of sodium chlorite that is therapeutically-effective for ALS.

Embodiment 84. The method of embodiment 83, wherein the subject is at least age 40.

Embodiment 85. The method of embodiment 83 or 84, wherein the amount is about 0.2 mg/kg/day to about 3.5 mg/kg/day.

Embodiment 86. The method of any one of embodiments 83-85, wherein the administering is oral.

Embodiment 87. The method of any one of embodiments 83-85, wherein the administering is parenteral.

Embodiment 88. The method of claim any one of embodiments 83-87, wherein the identifying that the subject has the level of TGFB1 associated with ALS is done by obtaining a result from an assay of the subject.

Embodiment 89. The method of embodiment 88, further comprising performing the assay of the subject to obtain the result.

Embodiment 90. The method of embodiment 88 or 89, wherein the assay is a blood assay.

Embodiment 91. The method of any one of embodiments 88-90, wherein the assay is a quantification of TGFB1 in blood of the subject by high performance liquid chromatography.

Embodiment 92. A method comprising:
a) determining a level of TGFB1 in a subject that has ALS, wherein the subject is undergoing a treatment for the ALS, wherein the treatment is a therapeutic regimen of sodium chlorite; and
b) determining based on the level of TGFB1 whether to continue the therapeutic regimen of sodium chlorite.

Embodiment 93. The method of embodiment 92, wherein the subject is at least age 40.

Embodiment 94. The method of embodiment 92 or 93, wherein the therapeutic regimen of sodium chlorite is about 0.2 mg/kg/day to about 3.5 mg/kg/day.

Embodiment 95. The method of any one of embodiments 92-94, wherein the therapeutic regimen of sodium chlorite is administered orally.

Embodiment 96. The method of any one of embodiments 92-94, wherein the therapeutic regimen of sodium chlorite is administered parenterally.

Embodiment 97. The method of any one of embodiments 92-96, further comprising determining to continue the therapeutic regimen of sodium chlorite.

Embodiment 98. The method of any one of embodiments 92-96, further comprising determining to discontinue the therapeutic regimen of sodium chlorite.

Embodiment 99. The method of any one of embodiments 92-99, wherein the determining the level of TGFB1 in the subject is done by obtaining a result from an assay of the subject.

Embodiment 100. The method of embodiment 99, further comprising performing the assay of the subject to obtain the result.

Embodiment 101. The method of embodiment 99 or 100, wherein the assay is a blood assay.

Embodiment 102. The method of any one of embodiments 99-101, wherein the assay is a quantification of TGFB1 in blood of the subject by high performance liquid chromatography.

Embodiment 103. A method comprising:
a) obtaining a first level of TGFB1 of a subject who has ALS, wherein the first level of TGFB1 of the subject who has ALS is based on a blood assay;
b) based at least in part on the first level of TGFB1 of the subject, starting the subject on a regimen of sodium chlorite administration for a time period of at least about six months;
c) after the time period, obtaining a second level of TGFB1 of the subject;
d) determining that the second level of TGFB1 is higher than the first level of TGFB1 of the subject by a predetermined threshold amount; and e) based at least in part on the determining that the second level TGFB1 of the subject is higher than the first level of TGFB1 of the subject by the predetermined threshold amount, recommending that the subject continue the regimen of sodium chlorite administration.

Embodiment 104. The method of embodiment 103, wherein the subject is at least age 40.

Embodiment 105. The method of embodiment 103 or 104, wherein the subject possesses a CRP level greater than 1.13 mg/L as determined by a blood assay.

Embodiment 106. The method of any one of embodiments 103-105, wherein the regimen of sodium chlorite is about 0.2 mg/kg/day to about 3.5 mg/kg/day.

Embodiment 107. The method of any one of embodiments 103-106, wherein the regimen of sodium chlorite is administered orally.

Embodiment 108. The method of any one of embodiments 103-106, wherein the regimen of sodium chlorite is administered parenterally.

Embodiment 109. The method of any one of embodiments 103-108, further comprising determining to continue the regimen of sodium chlorite.

Embodiment 110. The method of any one of embodiments 103-108, further comprising determining to discontinue the regimen of sodium chlorite.

Embodiment 111. The method of any one of embodiments 103-110, wherein the assay is a quantification of TGFB1 in blood of the subject by high performance liquid chromatography.

Embodiment 112. A method comprising:
a) identifying that a subject has a level of LBP associated with ALS; and
b) based on the identifying that the subject has the level of LBP associated with ALS, determining that the subject is eligible for sodium chlorite therapy for the ALS.

Embodiment 113. The method of embodiment 112, wherein the subject has ALS.

Embodiment 114. The method of embodiment 112 or 113, wherein the subject is at least age 40.

Embodiment 115. The method of any one of embodiments 112-114, wherein the subject possesses a CRP level greater than 1.13 mg/L as determined by a blood assay.

Embodiment 116. The method of any one of embodiments 112-115, wherein the sodium chlorite therapy is about 0.2 mg/kg/day to about 3.5 mg/kg/day.

Embodiment 117. The method of any one of embodiments 112-116, further comprising recommending that the subject undergo the sodium chlorite therapy for the ALS based on the determining that the subject is eligible for sodium chlorite therapy for the ALS.

Embodiment 118. The method of any one of embodiments 112-117, further comprising administering to the subject the sodium chlorite therapy.

Embodiment 119. The method of any one of embodiments 112-118, further comprising orally administering to the subject the sodium chlorite therapy.

Embodiment 120. The method of any one of embodiments 112-118, further comprising parenterally administering to the subject the sodium chlorite therapy.

Embodiment 121. The method of any one of embodiments 112-120, wherein the identifying that the subject has the level of LBP associated with ALS is done by obtaining a result from an assay of the subject.

Embodiment 122. The method of embodiment 121, further comprising performing the assay of the subject to obtain the result.

Embodiment 123. The method of embodiment 121 or 122, wherein the assay is a blood assay.

Embodiment 124. The method of any one of embodiments 121-123, wherein the assay is a quantification of LBP in blood of the subject by high performance liquid chromatography.

Embodiment 125. A method of treating ALS in a subject in need thereof, the method comprising:
a) identifying that a subject has a level of LBP associated with ALS; and
b) based on the identifying that the subject has the level of LBP associated with ALS, administering to the subject an amount of sodium chlorite that is therapeutically-effective for ALS.

Embodiment 126. The method of embodiment 125, wherein the subject is at least age 40.

Embodiment 127. The method of embodiment 125 or 126, wherein the amount is about 0.2 mg/kg/day to about 3.5 mg/kg/day.

Embodiment 128. The method of any one of embodiments 125-127, wherein the administering is oral.

Embodiment 129. The method of any one of embodiments 125-128, wherein the administering is parenteral.

Embodiment 130. The method of any one of embodiments 125-129, wherein the identifying that the subject has the level of LBP associated with ALS is done by obtaining a result from an assay of the subject.

Embodiment 131. The method of embodiment 130, further comprising performing the assay of the subject to obtain the result.

Embodiment 132. The method of embodiment 130 or 131, wherein the assay is a blood assay.

Embodiment 133. The method of any one of embodiments 130-132, wherein the assay is a quantification of LBP in blood of the subject by high performance liquid chromatography.

Embodiment 134. A method comprising:
a) determining a level of LBP in a subject that has ALS, wherein the subject is undergoing a treatment for the ALS, wherein the treatment is a therapeutic regimen of sodium chlorite; and
b) determining based on the level of LBP whether to continue the therapeutic regimen of sodium chlorite.

Embodiment 135. The method of embodiment 134, wherein the subject is at least age 40.

Embodiment 136. The method of embodiment 134 or 135, wherein the therapeutic regimen of sodium chlorite is about 0.2 mg/kg/day to about 3.5 mg/kg/day.

Embodiment 137. The method of any one of embodiments 134-136, wherein the therapeutic regimen of sodium chlorite is administered orally.

Embodiment 138. The method of any one of embodiments 134-136, wherein the therapeutic regimen of sodium chlorite is administered parenterally.

Embodiment 139. The method of any one of embodiments 134-138, further comprising determining to continue the therapeutic regimen of sodium chlorite.

Embodiment 140. The method of any one of embodiments 134-138, further comprising determining to discontinue the therapeutic regimen of sodium chlorite.

Embodiment 141. The method of any one of embodiments 134-140, wherein the determining the level of LBP in the subject is done by obtaining a result from an assay of the subject.

Embodiment 142. The method of embodiment 141, further comprising performing the assay of the subject to obtain the result.

Embodiment 143. The method of embodiment 141 or 142, wherein the assay is a blood assay.

Embodiment 144. The method of any one of embodiments 140-143, wherein the assay is a quantification of LBP in blood of the subject by high performance liquid chromatography.

Embodiment 145. A method comprising:
a) obtaining a first level of LBP of a subject who has ALS, wherein the first level of TGFB1 of the subject who has ALS is based on a blood assay;
b) based at least in part on the first level of LBP of the subject, starting the subject on a regimen of sodium chlorite administration for a time period of at least about six months;
c) after the time period, obtaining a second level of LBP of the subject;
d) determining that the second level of LBP is lower than the first level of TGFB1 of the subject by a predetermined threshold amount; and
e) based at least in part on the determining that the second level of LBP of the subject is lower than the first level of LBP of the subject by the predetermined threshold amount, recommending that the subject continue the regimen of sodium chlorite administration.

Embodiment 146. The method of embodiment 145, wherein the subject is at least age 40.

Embodiment 147. The method of embodiment 145 or 146, wherein the subject possesses a CRP level greater than 1.13 mg/L as determined by a blood assay.

Embodiment 148. The method of any one of embodiments 145-147, wherein the regimen of sodium chlorite is about 0.2 mg/kg/day to about 3.5 mg/kg/day.

Embodiment 149. The method of any one of embodiments 145-148, wherein the regimen of sodium chlorite is administered orally.

Embodiment 150. The method of any one of embodiments 145-148, wherein the regimen of sodium chlorite is administered parenterally.

Embodiment 151. The method of any one of embodiments 145-150, further comprising determining to continue the regimen of sodium chlorite.

Embodiment 152. The method of any one of embodiments 145-150, further comprising determining to discontinue the regimen of sodium chlorite.

Embodiment 153. The method of any one of embodiments 145-152, wherein the assay is a quantification of LBP in blood of the subject by high performance liquid chromatography.

What is claimed is:

1. A method of treating a neurodegenerative disease in a subject in need thereof, the method comprising:
a) obtaining a first level of a biomarker in the subject;
b) subsequent to obtaining the first level of the biomarker in the subject, administering to the subject a therapeutic regimen of sodium chlorite;
c) subsequent to the administering to the subject the therapeutic regimen of sodium chlorite, obtaining a second level of the biomarker in the subject;
d) subsequent to obtaining the second level of the biomarker in the subject, comparing the first level of the biomarker in the subject to the second level of the biomarker in the subject to identify a change from the first level of the biomarker in the subject to the second level of the biomarker in the subject; and
e) based at least in part on the change from the first level of the biomarker in the subject to the second level of the biomarker in the subject, recommending that the subject continue the therapeutic regimen of sodium chlorite, wherein the change from the first level of the biomarker in the subject to the second level of the biomarker in the subject is an increase,
wherein the biomarker is TGFB1.

2. The method of claim 1, wherein the subject is a human.

3. The method of claim 1, wherein the neurodegenerative disease is amyotrophic lateral sclerosis (ALS).

4. The method of claim 1, wherein the therapeutic regimen of sodium chlorite is about 0.1 mg/kg to about 10 mg/kg by body mass of the subject.

5. The method of claim 1, wherein the therapeutic regimen of sodium chlorite is about 0.2 mg/kg to about 3.5 mg/kg by body mass of the subject.

6. The method of claim 1, wherein the administering is oral.

7. The method of claim 1, wherein the administering is parenteral.

8. The method of claim 1, wherein the administering is for 5 consecutive days in a first month and 3 consecutive days in subsequent months.

9. The method of claim 1, wherein the administering slows loss of vital capacity in the subject.

10. A method of treating amyotrophic lateral sclerosis (ALS) in a human subject in need thereof, the method comprising:
a) obtaining a first level of a biomarker in the human subject from a first assay;
b) subsequent to obtaining the first level of the biomarker in the human subject, parenterally administering to the subject a therapeutic regimen of sodium chlorite;
c) subsequent to the administering to the subject the therapeutic regimen of sodium chlorite, obtaining a second level of the biomarker in the human subject from a second assay;
d) subsequent to obtaining the second level of the biomarker in the human subject, comparing the first level of the biomarker in the human subject to the second level of the biomarker in the human subject to identify an increase from the first level of the biomarker in the human subject to the second level of the biomarker in the human subject; and
e) based at least in part on the increase from the first level of the biomarker in the human subject to the second level of the biomarker in the subject, recommending that the human subject continue the therapeutic regimen of sodium chlorite,
wherein the biomarker is TGFB1.

11. The method of claim 10, wherein the therapeutic regimen of sodium chlorite is about 0.1 mg/kg to about 10 mg/kg by body mass of the human subject, wherein the administering is for 5 consecutive days in a first month and 3 consecutive days in subsequent months.

12. A method of treating amyotrophic lateral sclerosis (ALS) in a human subject in need thereof, the method comprising:
a) performing a first assay of blood of the human subject to obtain a first level of a biomarker in the human subject;
b) subsequent to obtaining the first level of the biomarker in the human subject, parenterally administering to the subject a therapeutic regimen of sodium chlorite;
c) subsequent to the administering to the subject the therapeutic regimen of sodium chlorite, performing a second assay of blood of the human subject to obtain a second level of the biomarker in the human subject;

d) subsequent to obtaining the second level of the biomarker in the human subject, comparing the first level of the biomarker in the human subject to the second level of the biomarker in the human subject to identify an increase from the first level of the biomarker in the human subject to the second level of the biomarker in the human subject; and e) based at least in part on the increase from the first level of the biomarker in the human subject to the second level of the biomarker in the human subject, continuing the therapeutic regimen of sodium chlorite, wherein the biomarker is TGFB1.

13. The method of claim 12, wherein the therapeutic regimen of sodium chlorite is about 0.1 mg/kg to about 10 mg/kg by body mass of the human subject, wherein the administering is for 5 consecutive days in a first month and 3 consecutive days in subsequent months.

14. The method of claim 1, further comprising obtaining a level of a second biomarker in the subject prior to recommending that the subject continue the therapeutic regimen of sodium chlorite, wherein the second biomarker is selected from SAA, NIL, HGF, A2M, EGF, IL10, neopterin, and a ratio of LPS:EGF.

15. The method of claim 10, further comprising obtaining a level of a second biomarker in the human subject prior to recommending that the human subject continue the therapeutic regimen of sodium chlorite, wherein the second biomarker is selected from SAA, NIL, HGF, A2M, EGF, IL10, neopterin, and a ratio of LPS:EGF.

16. The method of claim 12, further comprising obtaining a level of a second biomarker in the human subject prior to recommending that the human subject continue the therapeutic regimen of sodium chlorite, wherein the second biomarker is selected from SAA, NIL, HGF, A2M, EGF, IL10, neopterin, and a ratio of LPS:EGF.

17. The method of claim 10, wherein the therapeutic regimen of sodium chlorite is about 0.2 mg/kg to about 3.5 mg/kg by body mass of the human subject, wherein the administering is for 5 consecutive days in a first month and 3 consecutive days in subsequent months.

18. The method of claim 12, wherein the therapeutic regimen of sodium chlorite is about 0.2 mg/kg to about 3.5 mg/kg by body mass of the human subject, wherein the administering is for 5 consecutive days in a first month and 3 consecutive days in subsequent months.

* * * * *

UNITED STATES PATENT AND TRADEMARK OFFICE
CERTIFICATE OF CORRECTION

| | | |
|---|---|---|
| PATENT NO. | : 12,233,086 B2 | Page 1 of 1 |
| APPLICATION NO. | : 18/319355 | |
| DATED | : February 25, 2025 | |
| INVENTOR(S) | : Arasteh Azhir, Michael S. McGrath and Bruce D. Forrest | |

It is certified that error appears in the above-identified patent and that said Letters Patent is hereby corrected as shown below:

On the Title Page

Title and in the Specification, Column 1, Lines 1-2 should read: Biomarkers for Neurodegenerative Disease;

In the Claims

Column 57, Claim 14, Line 22, please replace 'NIL' with NfL;
Column 58, Claim 15, Line 5, please replace 'NIL' with NfL; and
Column 58, Claim 16, Line 11, please replace 'NIL' with NfL.

Signed and Sealed this
Seventh Day of October, 2025

John A. Squires
*Director of the United States Patent and Trademark Office*